US012612427B2

(12) United States Patent
Zhang et al.

(10) Patent No.: US 12,612,427 B2
(45) Date of Patent: Apr. 28, 2026

(54) ARYL GLUCOSIDE DERIVATIVE, PREPARATION METHOD THEREFOR AND APPLICATION THEREOF

(71) Applicant: Shanghai Zheye Biotechnology Co. Ltd., Shanghai (CN)

(72) Inventors: Qiang Zhang, Shanghai (CN); Fengtian Du, Shanghai (CN); Haibo Wang, Shanghai (CN); Na Guo, Shanghai (CN)

(73) Assignee: Shanghai Zheye Biotechnology Co. Ltd., Shanghai (CN)

( * ) Notice: Subject to any disclaimer, the term of this patent is extended or adjusted under 35 U.S.C. 154(b) by 707 days.

(21) Appl. No.: 18/023,883

(22) PCT Filed: Nov. 24, 2020

(86) PCT No.: PCT/CN2020/131249

§ 371 (c)(1),
(2) Date: Feb. 28, 2023

(87) PCT Pub. No.: WO2021/227440

PCT Pub. Date: Nov. 18, 2021

(65) Prior Publication Data

US 2023/0331761 A1 Oct. 19, 2023

(30) Foreign Application Priority Data

May 15, 2020 (CN) ......................... 202010411235.5

(51) Int. Cl.
*C07H 15/14* (2006.01)
*A61K 45/06* (2006.01)
*A61P 3/10* (2006.01)

(52) U.S. Cl.
CPC ............. *C07H 15/14* (2013.01); *A61K 45/06* (2013.01); *A61P 3/10* (2018.01)

(58) Field of Classification Search
CPC . C07H 15/14; A61K 45/06; A61P 3/10; A61P 1/00
See application file for complete search history.

(56) References Cited

FOREIGN PATENT DOCUMENTS

| | | | | |
|---|---|---|---|---|
| CN | 106892948 A | | 6/2017 | |
| CN | 108610385 A | | 10/2018 | |
| CN | 110092768 A | * | 8/2019 | ........... C07D 309/10 |
| CN | 110117300 A | | 8/2019 | |
| WO | 2014081660 A1 | | 5/2014 | |

OTHER PUBLICATIONS

Partial Supplementary European Search Report including Written Opinion for Application No. 20935318.4 dated Mar. 4, 2025. 13 pages.

Goodwin, Nicole C et al. "Discovery of LX2761, a Sodium-Dependent Glucose Cotransporter 1 (SGLT1) Inhibitor Restricted to the Intestinal Lumen, for the Treatment of Diabetes." Journal of medicinal chemistry vol. 60,2 (Jan. 2017): pp. 710-721. doi:10.1021/acs.jmedchem.6b01541.

Goodwin, Nicole C. et al. "Discovery of LX2761. a Sodium-Dependent Glucose Cotransporter I(SGLTI) Inhibitor Restricted to the Intestinal Lumen. for the Treatment of Diabetes" J. Med. Chem., vol. 60, Jan. 3, 2017 (Jan. 3, 2017), pp. 710-721, see table 1, table 2.

Sirois, Lauren E. et al. "Process Development for a Locally Acting SGLTI Inhibitor, LX2761, Utilizing sp3-sp2 Suzuki Coupling of a Benzyl Carbonate" Org. Process Res. Dev., vol. 23, Dec. 24, 2018 (Dec. 24, 2018), pp. 45-61, see abstract, and figure 1.

International Search Report for PCT/CN2020/131249 mailed Jan. 22, 2021. 4 pgs.

* cited by examiner

*Primary Examiner* — Kamal A Saeed
*Assistant Examiner* — Meghan C Heasley
(74) *Attorney, Agent, or Firm* — Lerner David LLP

(57) ABSTRACT

Provided are a compound that inhibits sodium-glucose co-transporter 1, and a pharmaceutically acceptable salt and stereoisomer thereof. The compound is used in a pharmaceutical composition and preparation and usage methods, which comprise an application of a drug and composition thereof in the preparation for treating and improving diabetes, cardiovascular and cerebrovascular diseases, weight loss, fatty liver disease, constipation, metabolism-related diseases and tumor treatment.

14 Claims, 4 Drawing Sheets

ARYL GLUCOSIDE DERIVATIVE, PREPARATION METHOD THEREFOR AND APPLICATION THEREOF

CROSS-REFERENCE

The present application is a National Phase entry under 35 U.S.C. § 371 of International Application No. PCT/CN2020/131249, filed Nov. 24, 2020, which claims priority from Chinese Application No. 202010411235.5, filed on May 15, 2020, all of which are hereby incorporated herein by reference.

TECHNICAL FIELD

The present invention relates to a sodium-dependent glucose transporter 1 (SGLT1) inhibitor, a method for synthesizing a drug containing a composition thereof and use thereof in the treatment of metabolic diseases, especially type 2 diabetes.

BACKGROUND

Diabetes is a group of metabolic diseases characterized by hyperglycemia. Hyperglycemia is caused by defective insulin secretion, impaired biological action, or both. Long-term hyperglycemia in diabetes causes chronic damage and dysfunction of various tissues, especially eyes, kidneys, heart, blood vessels, and nerves. In 2012, the World Health Organization reported that the incidence of diabetes in adults over the age of 18 was greater than 9%. With the increase of population, aging and prolongation of life, the incidence of diabetes will increase. The incidence of diabetes is higher in obese people. Diabetes is projected to become the seventh leading cause of death by 2030.

Sodium-dependent glucose transporter (SGLT) inhibitors can inhibit the reabsorption of glucose by the kidneys, allowing excess glucose to be excreted from the urine, lowering blood glucose. It provides a new way for the treatment of diabetes and becomes a hot spot in the research of hypoglycemic drugs. Over the past decades, new targeted drugs have been developed for the treatment of diabetes. The SGLT family consists of several subtypes that play a role of transporting carbohydrates across the cell membrane, during which they bind to sodium ion transporters. SGLT1 is mainly expressed in the gastrointestinal passage and is mainly responsible for the absorption of glucose and galactose in the small intestine. SGLT1 is also present in the proximal straight tubule of the kidney, where it contributes to the reabsorption of blood glucose. By inhibiting SGLT1, blood glucose can be prevented from being absorbed and used back to the blood, thus achieving the goal of lowering blood glucose level. In documents, a compound with SGLT1 inhibitory effect, for example, Mizagliflozin entering clinical research, is used for the treatment of functional constipation, and has a molecular structure as follows:

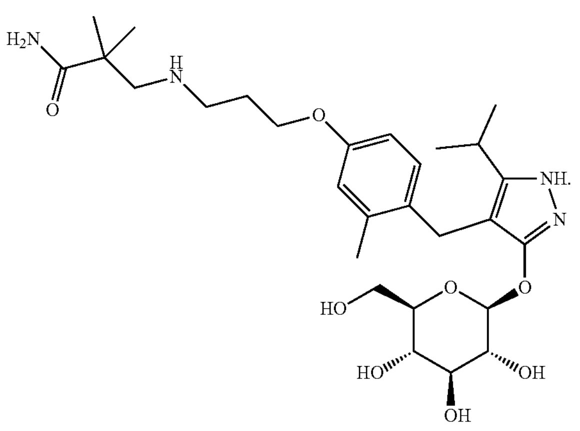

Mizagliflozin

Since SGLT1 inhibition may also provide an alternative therapy for glycemic control, the improvement of glycemic control by SGLT1 inhibition is attractive because it can be independent of renal function. Current SGLT2-selective inhibitors are ineffective in patients with moderate-to-severe renal impairment, which accounts for approximately 30-40% of all diabetic patients. Inhibition of intestinal SGLT1 has potential efficacy in glycemic control. Through this action, the diabetes-related side effects of SGLT2 inhibitors, especially genital infections, can also be avoided.

Despite recent advances in the development of intestinal SGLT1 inhibitors, there is still a need to develop new compounds with better efficacy. Through continuous efforts, the present invention has designed compounds with the structure of general formula (X) and found that compounds with such structure showed excellent effects and functions, and in a larger scope, the relationship between structure and activity efficacy have been revealed and clarified more deeply and comprehensively, which has important application value.

SUMMARY

The present invention provides a compound of formula (X), a stereoisomer, tautomer or pharmaceutically acceptable salt thereof, (X)

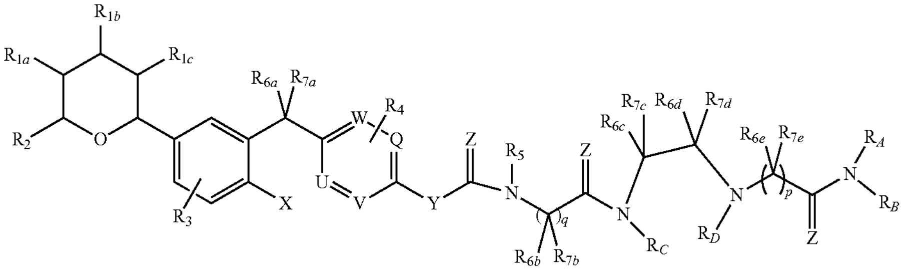

wherein, U, V, W and Q are each independently selected from nitrogen atom or CH;

$R_{1a}$, $R_{1b}$ and $R_{1c}$ are each independently selected from halogen or —$OR_{1A}$, and —$NHR_{1A}$, wherein each $R_{1A}$ is independently hydrogen, C1-C6 alkyl or acyl;

$R_2$ is selected from —$S(O)_m$—$R_{1A}$;

$R_C$ and $R_D$ are each independently selected from hydrogen, deuterium, halogen, C1-C6 alkyl, C3-C6 cycloalkyl, C2-C6 alkenyl and C2-C6 alkynyl;

alternatively, $R_C$ and $R_D$ together with nitrogen atoms attached therewith form a 3- to 8-membered heterocycle, the heterocycle is capable of containing one or more carbon, nitrogen, oxygen or sulfur atoms, and the heterocycle is capable of being further substituted by halogen, alkyl, cycloalkyl, aryl, alkoxy, alkenyl, alkynyl, or oxo;

$R_3$, $R_4$, $R_5$, $R_{6a}$, $R_{7a}$, $R_{6b}$, $R_{7b}$, $R_{6c}$, $R_{7c}$, $R_{6d}$, $R_{7d}$, $R_{6e}$ and $R_{7e}$ are each independently selected from hydrogen, deuterium, halogen, C1-C6 alkyl or acyl; alternatively, $R_{6a}$ and $R_{7a}$, $R_{6b}$ and $R_{7b}$, $R_{6c}$ and $R_{7c}$, $R_{6d}$ and $R_{7d}$, and $R_{6e}$ and $R_{7e}$ together with carbon atoms attached therewith are capable of forming a 3- to 8-membered carbocycle respectively, wherein the carbocycle is capable of being substituted by hydrogen, halogen, C1-C6 alkyl, and halogenated C1-C6 alkyl;

$R_A$ and $R_B$ are each independently selected from hydrogen, deuterium, alkyl, deuterated alkyl, haloalkyl, alkoxy, haloalkoxy, halogen, amino, mercapto, nitro, hydroxyl, cyano, oxo, C2-C8 alkenyl, C2-C8 alkynyl, cycloalkyl, heterocyclyl, aryl, heteroaryl, —$(CH_2)_{n1}R_{aa}$, —$(CH_2)_{n1}OR_{aa}$, —$SR_{aa}$, —$(CH_2)_{n1}C(O)R_{aa}$, —$SR_{aa}$, —$C(O)OR_{aa}$, —$C(O)R_{aa}$, —$S(O)_{m1}R_{aa}$, —$(CH_2)_{n1}S(O)_{m1}R_{aa}$, —$NR_{aa}R_{bb}$, —$C(O)NR_{aa}R_{bb}$, —$NR_{aa}C(O)R_{bb}$, and —$NR_{aa}S(O)_{m1}R_{bb}$;

alternatively, $R_A$ and $R_B$ together with nitrogen atoms attached therewith form a 3- to 8-membered heterocycle, the heterocycle is capable of containing one or more carbon, nitrogen, oxygen or sulfur atoms, and the heterocycle is capable of being further substituted by halogen, alkyl, cycloalkyl, aryl, alkoxy, alkenyl, alkynyl, or oxo;

$R_{aa}$ and $R_{bb}$ are each independently selected from hydrogen, deuterium, alkyl, deuterated alkyl, haloalkyl, alkoxy, hydroxyalkyl, haloalkoxy, halogen, cyano, nitro, hydroxy, amino, alkenyl, alkynyl, deuterated alkenyl, deuterated alkynyl, cycloalkyl, heterocyclyl, aryl and heteroaryl, wherein the alkyl, deuterated alkyl, haloalkyl, alkoxy, hydroxyalkyl, haloalkoxy, alkenyl, alkynyl, deuterated alkenyl, deuterated alkynyl, cycloalkyl, heterocyclyl, aryl and heteroaryl, are optionally further substituted by one or more substituents selected from hydrogen, deuterium, silyl, alkylsilyl, substituted or unsubstituted alkyl, halogen, hydroxy, substituted or unsubstituted amino, oxo, nitro, cyano, substituted or unsubstituted alkenyl, substituted or unsubstituted alkynyl, substituted or unsubstituted alkoxy, substituted or unsubstituted hydroxyalkyl, substituted or unsubstituted cycloalkyl, substituted or unsubstituted heterocyclyl, substituted or unsubstituted aryl and substituted or unsubstituted heteroaryl;

each Z is independently selected from oxygen atom, sulfur atom, and NH;

n1=0, 1, 2, 3, 4;

m1=0, 1, 2, 3, 4;

m=0, 1, 2, 3;

p=0, 1, 2, 3;

q=0, 1, 2, 3;

X is selected from hydrogen, deuterium, halogen, C1-C6 alkyl, C3-C6 cycloalkyl, C2-C6 alkenyl, and C2-C6 alkynyl;

Y is a linking group selected from the following structures:

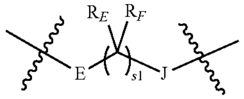
;
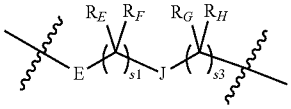
;

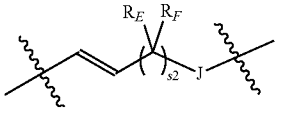

wherein, $R_E$, $R_F$, $R_G$ and $R_H$ are each independently selected from hydrogen, deuterium, halogen, C1-C6 alkyl or acyl;

E and J are each independently selected from chemical bonds, —$CH_2$—, oxygen, and —NH—;

s1=0, 1, 2, 3, 4, 5;

s2=0, 1, 2, 3, 4, 5; and s3=0, 1, 2, 3, 4, 5.

The present invention provides a compound of formula (XA), a stereoisomer, tautomer or pharmaceutically acceptable salt thereof, (XA)

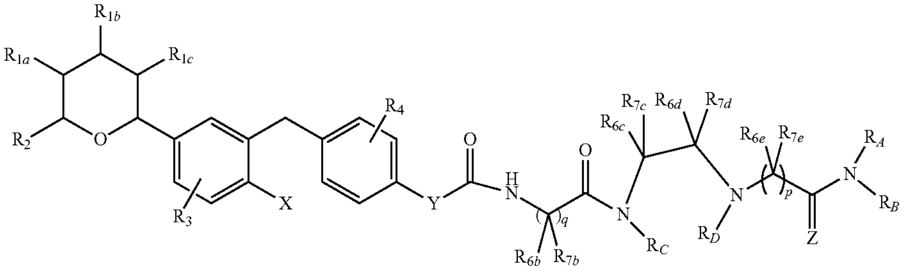

wherein, $R_{1a}$, $R_{1b}$ and $R_{1c}$ are each independently selected from halogen or —$OR_{1A}$, and —$NHR_{1A}$, wherein each $R_{1A}$ is independently hydrogen, C1-C6 alkyl or acyl;

$R_2$ is selected from —$S(O)_m$—$R_{1A}$;

$R_C$ and $R_D$ are each independently selected from hydrogen, deuterium, halogen, C1-C6 alkyl, C3-C6 cycloalkyl, C2-C6 alkenyl and C2-C6 alkynyl;

alternatively, $R_C$ and $R_D$ together with nitrogen atoms attached therewith form a 3- to 8-membered heterocycle, the heterocycle is capable of containing one or more carbon, nitrogen, oxygen or sulfur atoms, and the heterocycle is capable of being further substituted by halogen, alkyl, cycloalkyl, aryl, alkoxy, alkenyl, alkynyl, or oxo;

$R_3$, $R_4$, $R_{6b}$, $R_{7b}$, $R_{6c}$, $R_{7c}$, $R_{6d}$, $R_{7d}$, $R_{6e}$ and $R_{7e}$ are each independently selected from hydrogen, deuterium, halogen, C1-C6 alkyl or acyl; alternatively, $R_{6b}$ and $R_{7b}$, $R_{6c}$ and $R_{7c}$, $R_{6d}$ and $R_{7d}$, and $R_{6e}$ and $R_{7e}$ together with carbon atoms attached therewith are capable of forming a 3- to 8-membered carbocycle respectively, wherein the carbocycle is capable of being substituted by hydrogen, halogen, C1-C6 alkyl, and halogenated C1-C6 alkyl;

$R_A$ and $R_B$ are each independently selected from hydrogen, deuterium, alkyl, deuterated alkyl, haloalkyl, alkoxy, haloalkoxy, halogen, amino, mercapto, nitro, hydroxyl, cyano, oxo, C2-C8 alkenyl, C2-C8 alkynyl, cycloalkyl, heterocyclyl, aryl, heteroaryl, —$(CH_2)_{n1}R_{aa}$, —$(CH_2)_{n1}OR_{aa}$, —$SR_{aa}$, —$(CH_2)_{n1}C(O)R_{aa}$, —$SR_{aa}$, —$C(O)OR_{aa}$, —$C(O)R_{aa}$, —$S(O)_{m1}R_{aa}$, —$(CH_2)_{n1}S(O)_{m1}R_{aa}$, —$NR_{aa}R_{bb}$, —$C(O)NR_{aa}R_{bb}$, —$NR_{aa}C(O)R_{bb}$, and —$NR_{aa}S(O)_{m1}R_{bb}$;

$R_{aa}$ and $R_{bb}$ are each independently selected from hydrogen, deuterium, alkyl, deuterated alkyl, haloalkyl, alkoxy, hydroxyalkyl, haloalkoxy, halogen, cyano, nitro, hydroxy, amino, alkenyl, alkynyl, deuterated alkenyl, deuterated alkynyl, cycloalkyl, heterocyclyl, aryl and heteroaryl, wherein the alkyl, deuterated alkyl, haloalkyl, alkoxy, hydroxyalkyl, haloalkoxy, alkenyl, alkynyl, deuterated alkenyl, deuterated alkynyl, cycloalkyl, heterocyclyl, aryl and heteroaryl, are optionally further substituted by one or more substituents selected from hydrogen, deuterium, silyl, alkylsilyl, substituted or unsubstituted alkyl, halogen, hydroxy, substituted or unsubstituted amino, oxo, nitro, cyano, substituted or unsubstituted alkenyl, substituted or unsubstituted alkynyl, substituted or unsubstituted alkoxy, substituted or unsubstituted hydroxyalkyl, substituted or unsubstituted cycloalkyl, substituted or unsubstituted heterocyclyl, substituted or unsubstituted aryl and substituted or unsubstituted heteroaryl;

alternatively,

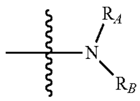

$R_B$ is selected from the following structures:

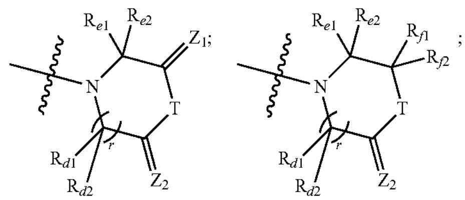

;

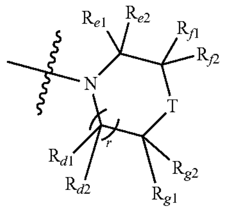

wherein, $Z_1$ and $Z_2$ are selected from oxygen atom or sulfur atom;

T is chemical bond, oxygen atom and —NR7h, substituted or unsubstituted carbon atom, wherein the substituents comprise hydrogen, deuterium, halogen, C1-C6 alkyl or acyl;

$R_{d1}$, $R_{d2}$, $R_{e1}$, $R_{e2}$, $R_{f1}$, $R_{f2}$, $R_{g1}$, $R_{g2}$ and $R_{7h}$ are each independently selected from hydrogen, deuterium, halogen, C1-C6 alkyl or acyl;

r=0, 1, 2, 3;

Z is selected from oxygen and sulfur atoms;

n1=0, 1, 2, 3, 4;

m1=0, 1, 2, 3, 4;

m=0, 1, 2;

p=0, 1, 2, 3;

q=0, 1, 2, 3;

X is selected from hydrogen, deuterium, halogen, C1-C6 alkyl, C3-C6 cycloalkyl, C2-C6 alkenyl, and C2-C6 alkynyl;

Y is a linking group selected from the following structures:

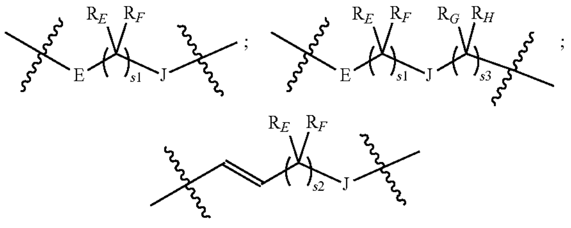

wherein, $R_E$, $R_F$, $R_G$ and $R_H$ are each independently selected from hydrogen, deuterium, halogen, C1-C6 alkyl or acyl;

E and J are each independently selected from chemical bonds, $—CH_2—$, oxygen, and —NH—;

s1=0, 1, 2, 3, 4, 5;

s2=0, 1, 2, 3, 4, 5; and s3=0, 1, 2, 3, 4, 5.

The present invention provides a compound of formula (XA-1), a stereoisomer, tautomer or pharmaceutically acceptable salt thereof, (XA-1)

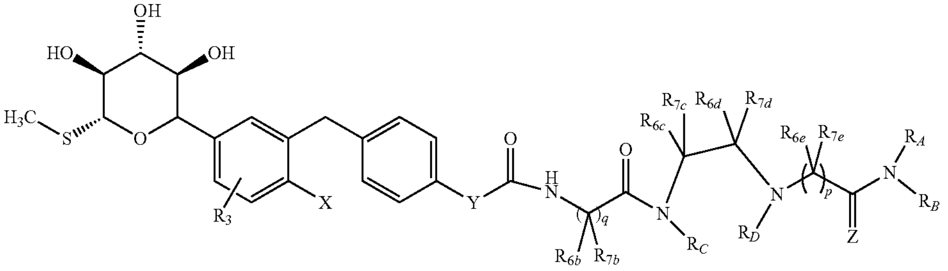

wherein, X, $R_C$ and $R_D$ are each independently selected from hydrogen, deuterium, halogen, C1-C6 alkyl, C3-C6 cycloalkyl, C2-C6 alkenyl and C2-C6 alkynyl;

$R_{6b}$, $R_{7b}$, $R_{6c}$, $R_{7c}$, $R_{6d}$, $R_{7d}$, $R_{6e}$ and $R_{7e}$ are each independently selected from hydrogen, deuterium, halogen, C1-C6 alkyl or acyl; alternatively, $R_{6b}$ and $R_{7b}$, $R_{6c}$ and $R_{7c}$, $R_{6d}$ and $R_{7d}$, and $R_{6e}$ and $R_{7e}$ together with carbon atoms attached therewith are capable of forming a 3- to 8-membered carbocycle respectively, wherein the carbocycle is capable of being substituted by hydrogen, halogen, C1-C6 alkyl, and halogenated C1-C6 alkyl;

$R_A$ and $R_B$ are each independently selected from hydrogen, deuterium, alkyl, deuterated alkyl, haloalkyl, alkoxy, haloalkoxy, halogen, amino, mercapto, nitro, hydroxyl, cyano, oxo, C2-C8 alkenyl, C2-C8 alkynyl, cycloalkyl, heterocyclyl, aryl, heteroaryl, $—(CH_2)_{n1}R_{aa}$, $—(CH_2)_{n1}OR_{aa}$, $—SR_{aa}$, $—(CH_2)_{n1}C(O)R_{aa}$, $—SR_{aa}$, $—C(O)OR_{aa}$, $—C(O)R_{aa}$, $—S(O)_{m1}R_{aa}$, $—(CH_2)_{n1}S(O)_{m1}R_{aa}$, $—NR_{aa}R_{bb}$, $—C(O)NR_{aa}R_{bb}$, $—NR_{aa}C(O)R_{bb}$, and $—NR_{aa}S(O)_{m1}R_{bb}$;

$R_{aa}$ and $R_{bb}$ are each independently selected from hydrogen, deuterium, alkyl, deuterated alkyl, haloalkyl, alkoxy, hydroxyalkyl, haloalkoxy, halogen, cyano, nitro, hydroxy, amino, alkenyl, alkynyl, deuterated alkenyl, deuterated alkynyl, cycloalkyl, heterocyclyl, aryl and heteroaryl, wherein the alkyl, deuterated alkyl, haloalkyl, alkoxy, hydroxyalkyl, haloalkoxy, alkenyl, alkynyl, deuterated alkenyl, deuterated alkynyl, cycloalkyl, heterocyclyl, aryl and heteroaryl, are optionally further substituted by one or more substituents selected from hydrogen, deuterium, silyl, alkylsilyl, substituted or unsubstituted alkyl, halogen, hydroxy, substituted or unsubstituted amino, oxo, nitro, cyano, substituted or unsubstituted alkenyl, substituted or unsubstituted alkynyl, substituted or unsubstituted alkoxy, substituted or unsubstituted hydroxyalkyl, substituted or unsubstituted cycloalkyl, substituted or unsubstituted heterocyclyl, substituted or unsubstituted aryl and substituted or unsubstituted heteroaryl;

$R_3$ is H; Z is O;

n1=0, 1, 2, 3, 4;

m1=0, 1, 2, 3, 4;

p=0, 1, 2, 3;

q=0, 1, 2, 3;

alternatively,

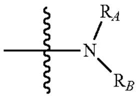

$R_B$ is selected from the following structures:

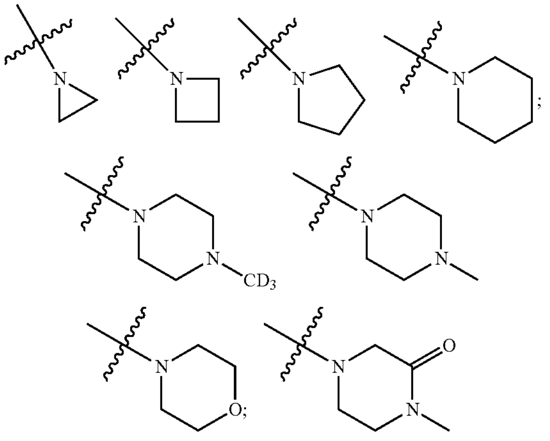

-continued
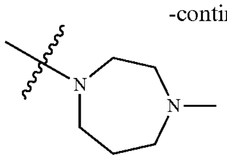
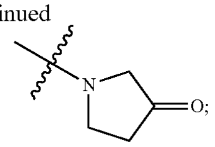
;
X is selected from hydrogen, deuterium, halogen, C1-C6 alkyl, C3-C6 cycloalkyl, C2-C6 alkenyl, and C2-C6 alkynyl;
Y is a linking group selected from the following structures:
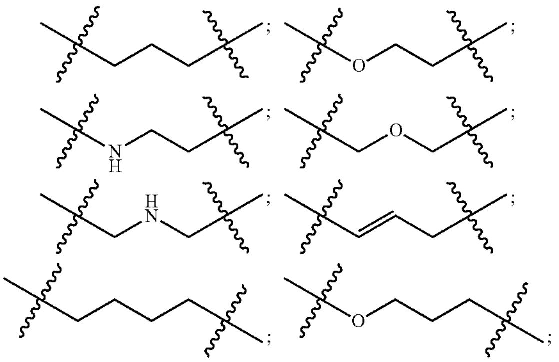
-continued
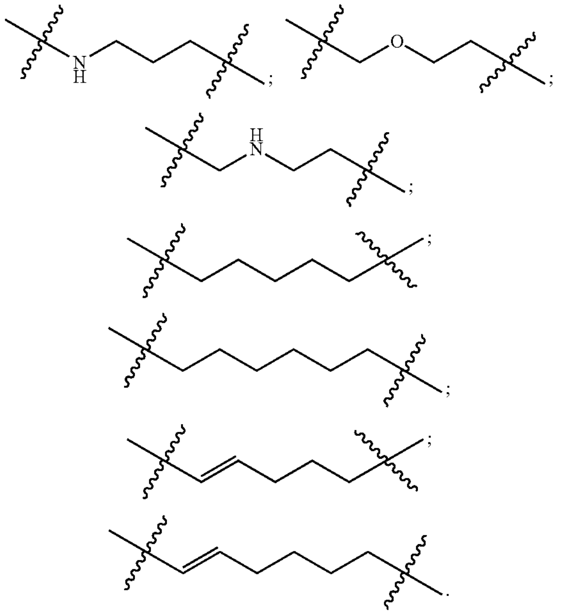
The present invention provides following compounds, stereoisomers, tautomers or pharmaceutically acceptable salts thereof,
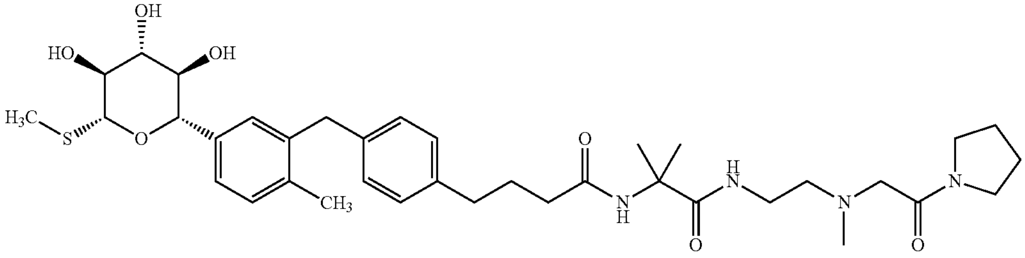
;
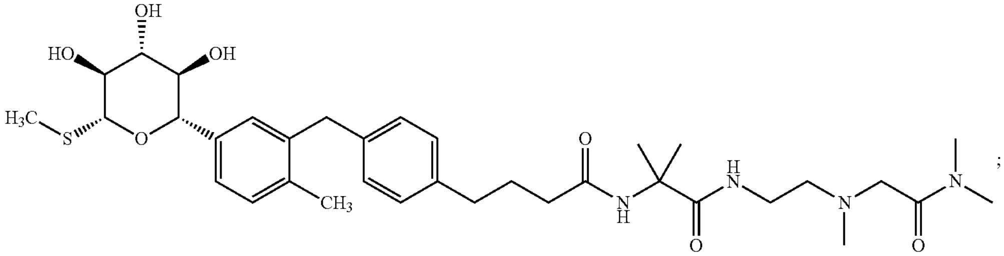
;
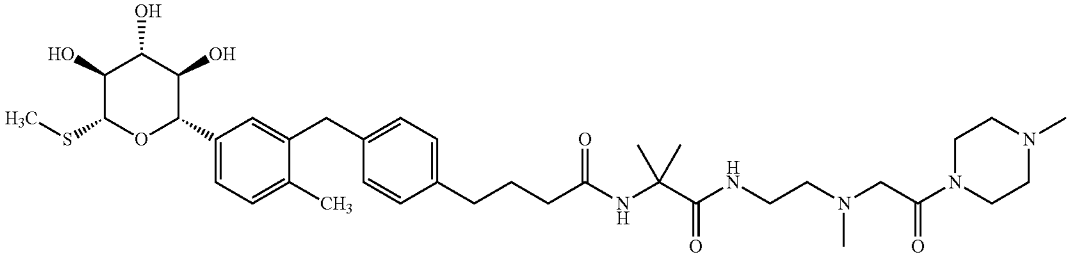
;

-continued
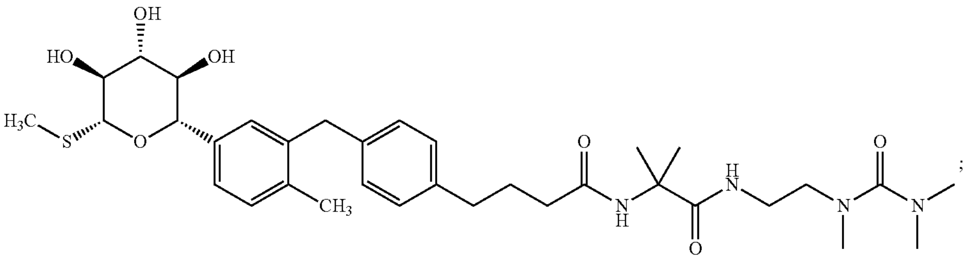
;
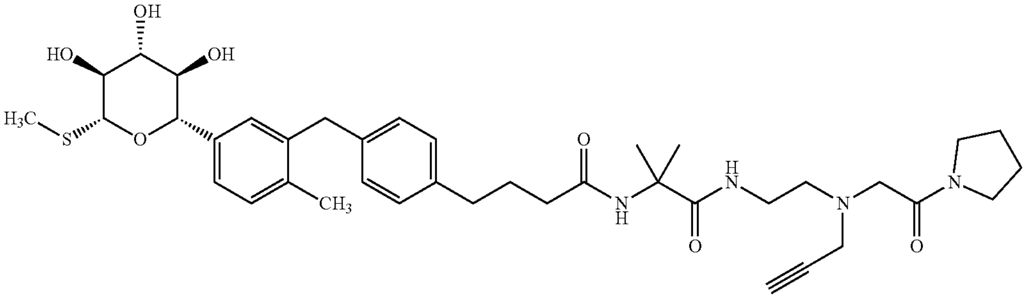
;
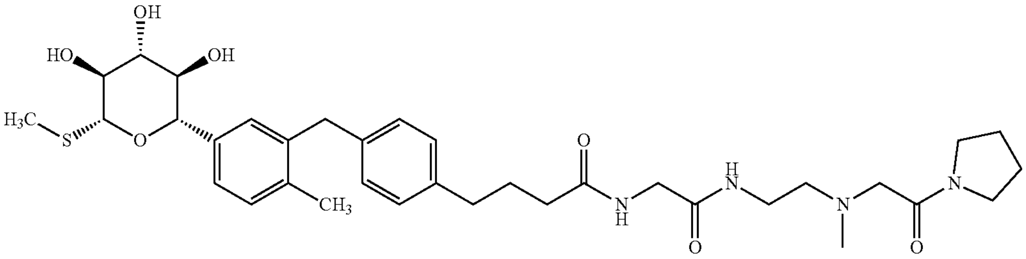
;
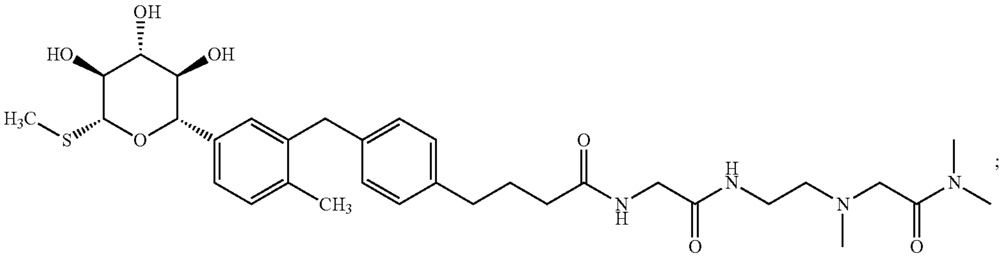
;
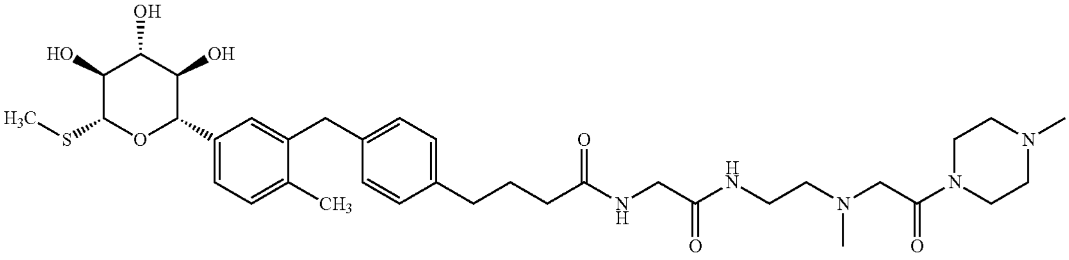
;
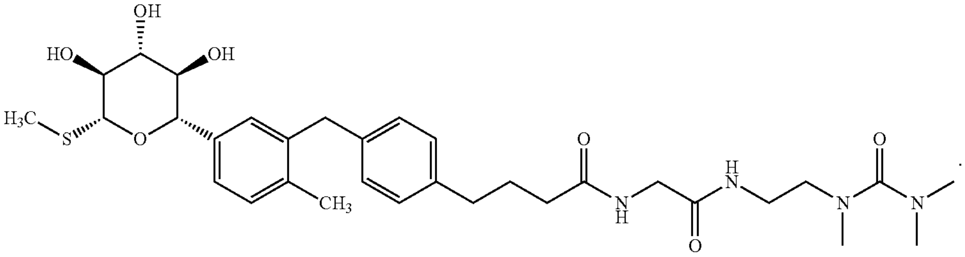
.

The present invention provides a compound of formula (XA-2), a stereoisomer, tautomer or pharmaceutically acceptable salt thereof, (XA-2)

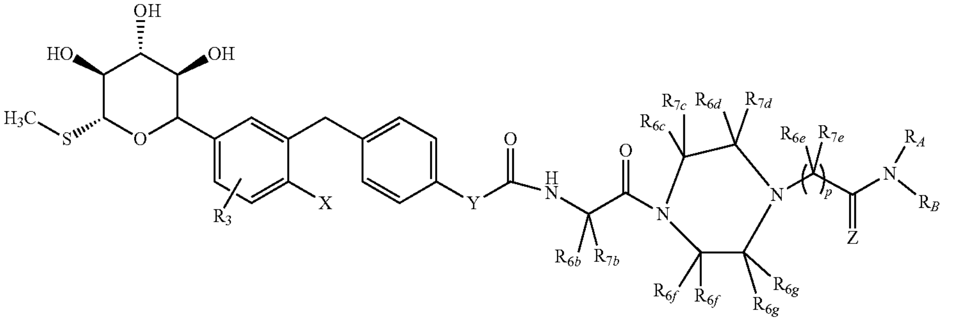

wherein, X is selected from hydrogen, deuterium, halogen, C1-C6 alkyl, C3-C6 cycloalkyl, C2-C6 alkenyl, and C2-C6 alkynyl;

$R_{6b}$, $R_{7b}$, $R_{6c}$, $R_{7c}$, $R_{6d}$, $R_{7d}$, $R_{6e}$, $R_{7e}$, $R_{6f}$, $R_{7f}$, $R_{6g}$ and $R_{7g}$ are each independently selected from hydrogen, deuterium, halogen, C1-C6 alkyl or acyl; alternatively, $R_{6b}$ and $R_{7b}$, $R_{6c}$ and $R_{7c}$, $R_{6a}$ and $R_{7d}$, and $R_{6e}$ and $R_{7e}$ together with carbon atoms attached therewith are capable of forming a 3- to 8-membered carbocycle respectively, wherein the carbocycle is capable of being substituted by hydrogen, halogen, C1-C6 alkyl, and halogenated C1-C6 alkyl;

$R_A$ and $R_B$ are each independently selected from hydrogen, deuterium, alkyl, deuterated alkyl, haloalkyl, alkoxy, haloalkoxy, halogen, amino, mercapto, nitro, hydroxyl, cyano, oxo, C2-C8 alkenyl, C2-C8 alkynyl, cycloalkyl, heterocyclyl, aryl, heteroaryl, $-(CH_2)_{n1}R_{aa}$, $-(CH_2)_{n1}OR_{aa}$, $-SR_{aa}$, $-(CH_2)_{n1}C(O)R_{aa}$, $-SR_{aa}$, $-C(O)OR_{aa}$, $-C(O)R_{aa}$, $-S(O)_{m1}R_{aa}$, $-(CH_2)_{n1}S(O)_{m1}R_{aa}$, $-NR_{aa}R_{bb}$, $-C(O)NR_{aa}R_{bb}$, $-NR_{aa}C(O)R_{bb}$, and $-NR_{aa}S(O)_{m1}R_{bb}$;

$R_{aa}$ and $R_{bb}$ are each independently selected from hydrogen, deuterium, alkyl, deuterated alkyl, haloalkyl, alkoxy, hydroxyalkyl, haloalkoxy, halogen, cyano, nitro, hydroxy, amino, alkenyl, alkynyl, deuterated alkenyl, deuterated alkynyl, cycloalkyl, heterocyclyl, aryl and heteroaryl, wherein the alkyl, deuterated alkyl, haloalkyl, alkoxy, hydroxyalkyl, haloalkoxy, alkenyl, alkynyl, deuterated alkenyl, deuterated alkynyl, cycloalkyl, heterocyclyl, aryl and heteroaryl, are optionally further substituted by one or more substituents selected from hydrogen, deuterium, silyl, alkylsilyl, substituted or unsubstituted alkyl, halogen, hydroxy, substituted or unsubstituted amino, oxo, nitro, cyano, substituted or unsubstituted alkenyl, substituted or unsubstituted alkynyl, substituted or unsubstituted alkoxy, substituted or unsubstituted hydroxyalkyl, substituted or unsubstituted cycloalkyl, substituted or unsubstituted heterocyclyl, substituted or unsubstituted aryl and substituted or unsubstituted heteroaryl;

$R_3$ is H; Z is O;

n1=0, 1, 2, 3, 4;

m1=0, 1, 2, 3, 4;

p=0, 1, 2, 3;

alternatively,

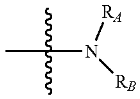

is selected from the following structures:

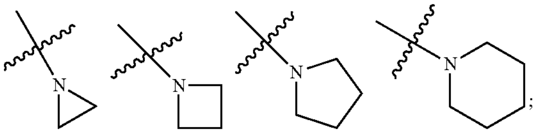
;

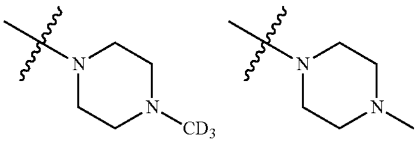

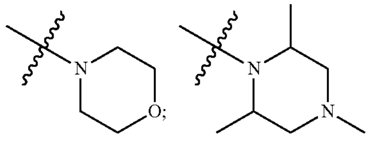

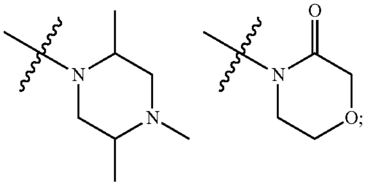

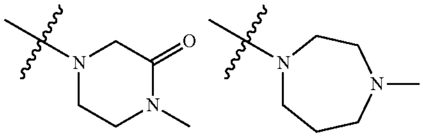

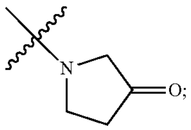

Y is a linking group selected from the following structures:
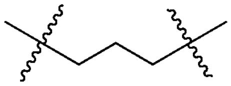;
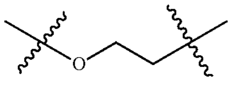;
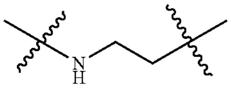;
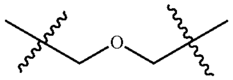;
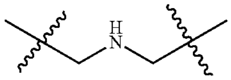;
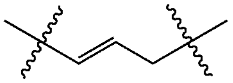;
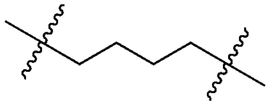;
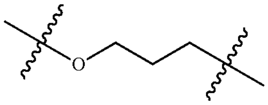;
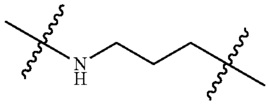;
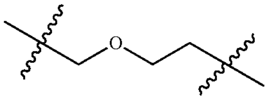;
-continued
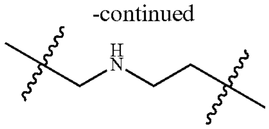;
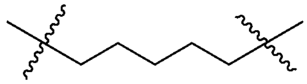;
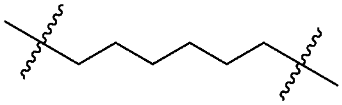;
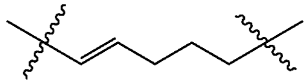;
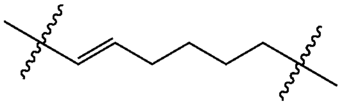.
The present invention provides following compounds, stereoisomers, tautomers or pharmaceutically acceptable salts thereof,
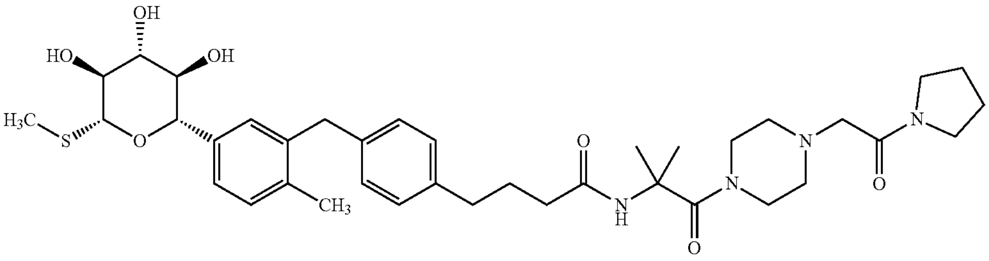;
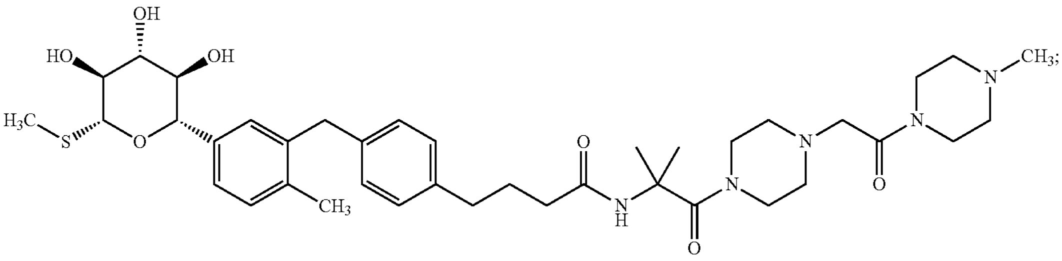
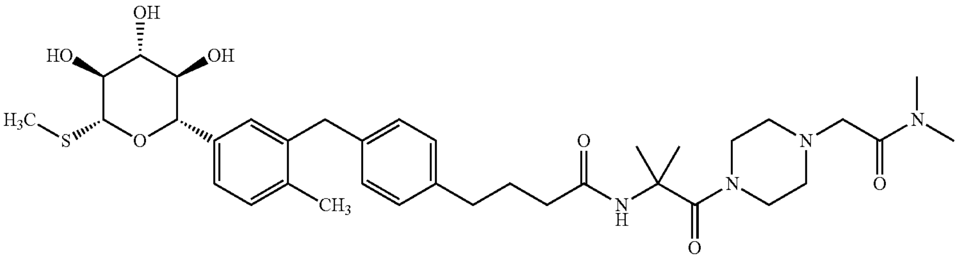;
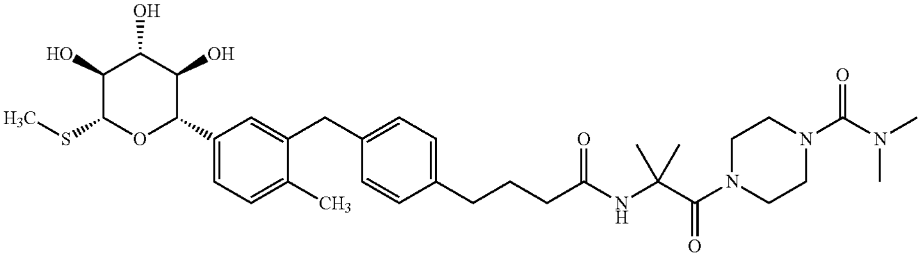;

-continued
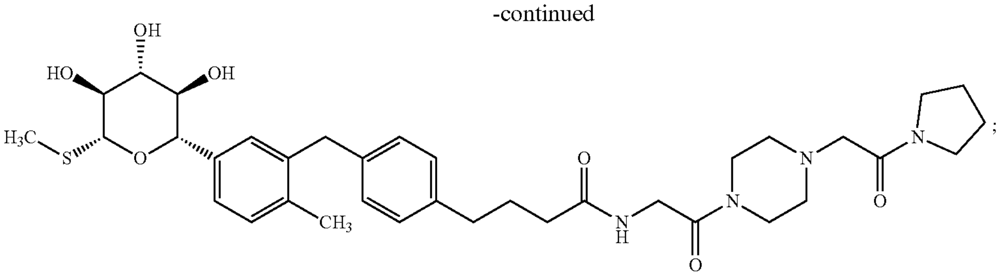
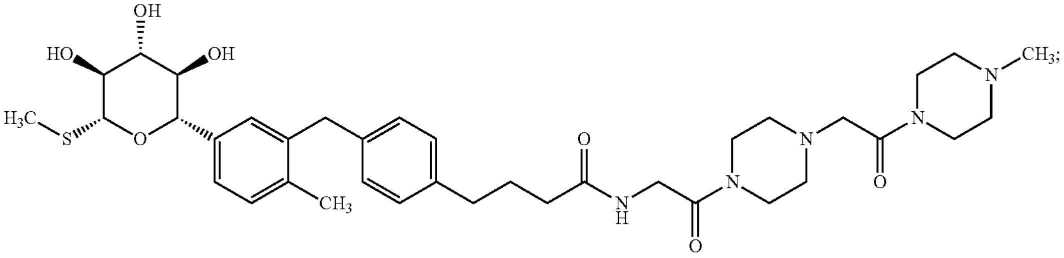
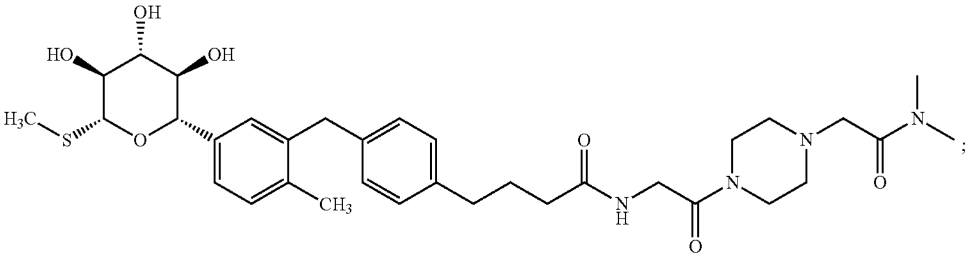
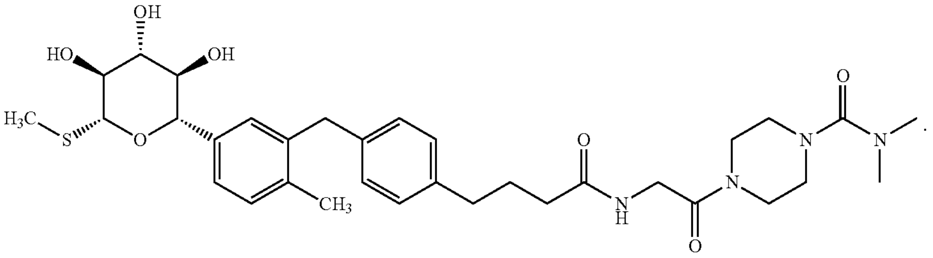
The present invention provides a compound of formula (I), a stereoisomer, tautomer or pharmaceutically acceptable salt thereof,
(I)
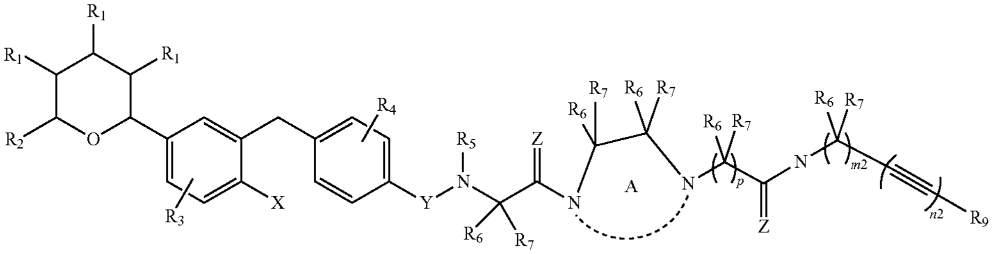

wherein, ring A is a nitrogen-containing heterocycle or an open ring structure;

$R_1$ is selected from F, —$OR_{1A}$, or —$NHR_{1A}$, wherein $R_{1A}$ is independently hydrogen, C1-C6 alkyl or acyl;

$R_2$ is selected from —$S(O)_m$—$R_{1A}$, and m=0, 1, 2;

$R_3$, $R_4$, $R_5$, $R_6$, $R_7$, $R_8$ and $R_9$ are selected from hydrogen, deuterium, halogen, C1-C6 alkyl or acyl, and alkynyl-alkyl;

m2=0, 1, 2, 3;

n2=0, 1, 2, 3;

p=0, 1, 2, 3, 4, 5;

X is selected from hydrogen, deuterium, halogen, C1-C6 alkyl, C3-C6 cycloalkyl, C2-C6 alkenyl, and C2-C6 alkynyl;

Y is a linking group, which is a linking arm composed of 2 to 17 carbon, oxygen and nitrogen atoms; and Z is O or S.

The present invention provides a compound of formula (I-1), a stereoisomer, tautomer or pharmaceutically acceptable salt thereof, (I-1)

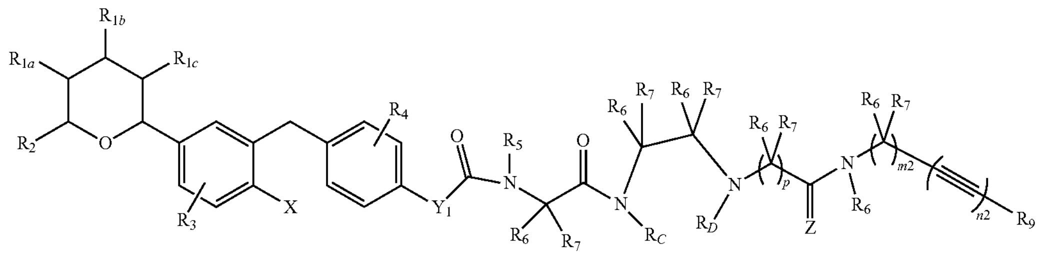

wherein, $R_{1a}$, $R_{1b}$ and $R_{1c}$ are each independently selected from F or —$OR_{1A}$, and —$NHR_{1A}$, wherein each $R_{1A}$ is independently hydrogen, C1-C6 alkyl or acyl;

$R_C$ and $R_D$ are each independently selected from hydrogen, deuterium, halogen, C1-C6 alkyl, C3-C6 cycloalkyl, C2-C6 alkenyl and C2-C6 alkynyl;

alternatively, $R_C$ and $R_D$ together with nitrogen atoms attached therewith form a 3- to 8-membered heterocycle, the heterocycle is capable of containing one or more carbon, nitrogen, oxygen or sulfur atoms, and the heterocycle is capable of being further substituted by halogen, alkyl, cycloalkyl, aryl, alkoxy, alkenyl, alkynyl, or oxo;

$R_2$ is selected from —$S(O)_m$—$R_{1A}$, and m=0, 1, 2;

$R_3$, $R_4$, $R_5$, $R_6$, $R_7$, $R_8$ and $R_9$ are each independently selected from hydrogen, deuterium, halogen, C1-C6 alkyl, cycloalkyl, cycloalkylalkyl or acyl, and C2-C8 alkynyl;

m2=0, 1, 2, 3;

n2=0, 1, 2, 3;

p=0, 1, 2, 3, 4, 5;

X is selected from hydrogen, deuterium, halogen, C1-C6 alkyl, C3-C6 cycloalkyl, C2-C6 alkenyl, and C2-C6 alkynyl;

Z is selected from oxygen and sulfur atoms;

$Y_1$ is a linking group selected from the following structures:

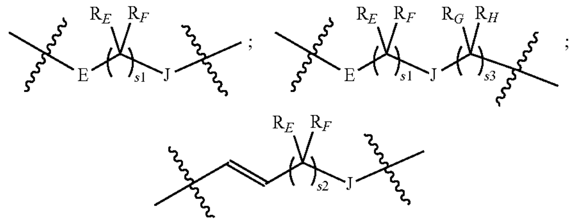

wherein, $R_E$, $R_F$, $R_G$ and $R_H$ are each independently selected from hydrogen, deuterium, halogen, C1-C6 alkyl or acyl;

E and J are independently selected from chemical bonds, —$CH_2$—, oxygen, and —NH—;

s1=0, 1, 2, 3, 4, 5;

s2=0, 1, 2, 3, 4, 5; and s3=0, 1, 2, 3, 4, 5.

The present invention provides the compound of formula (I), comprising compounds of the following general structural formula structures (II) and (III), stereoisomers, tautomers or pharmaceutically acceptable salts thereof, (II)

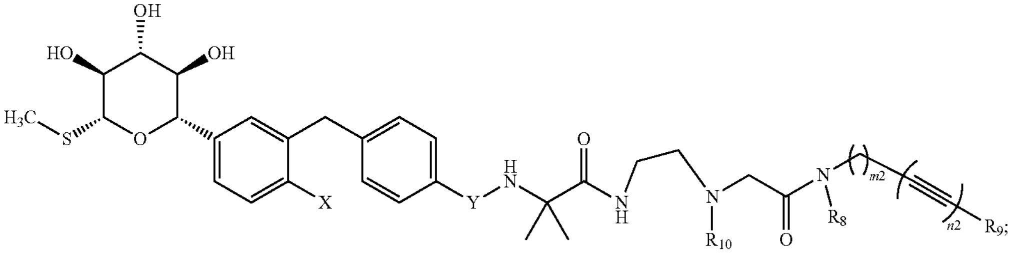

(III)

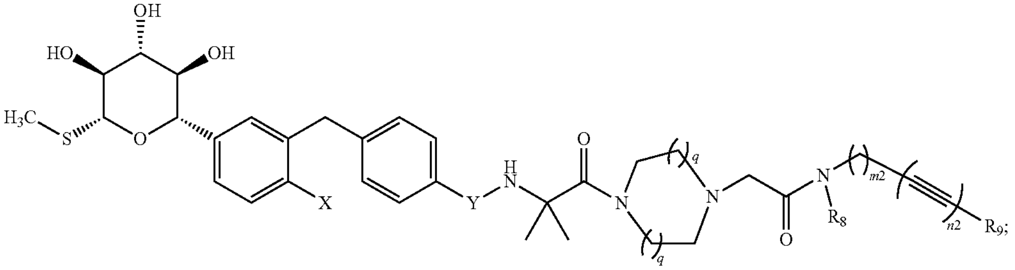

wherein, X is selected from hydrogen, deuterium, halogen, C1-C6 alkyl, C3-C6 cycloalkyl, C2-C6 alkenyl, and C2-C6 alkynyl;

$R_8$, $R_9$ and $R_{10}$ are each independently selected from hydrogen, deuterium, halogen, C1-C6 alkyl or acyl, and alkynylalkyl;

m2=0, 1, 2, 3;

n2=0, 1;

q=0, 1, 2, 3; and

Y is a linking group, which is a linking arm composed of 2 to 17 carbon, oxygen and nitrogen atoms.

The present invention provides a compound of formula (I-1), comprising compounds of the following general structural formula structures (II-1) and (III-1), stereoisomers, tautomers or pharmaceutically acceptable salts thereof, (II-1)

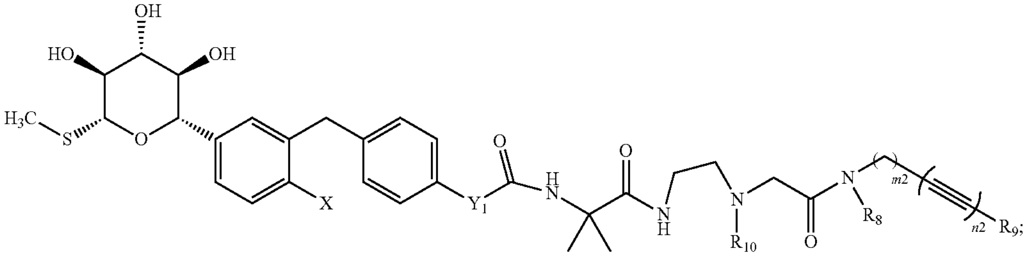

(III-1)

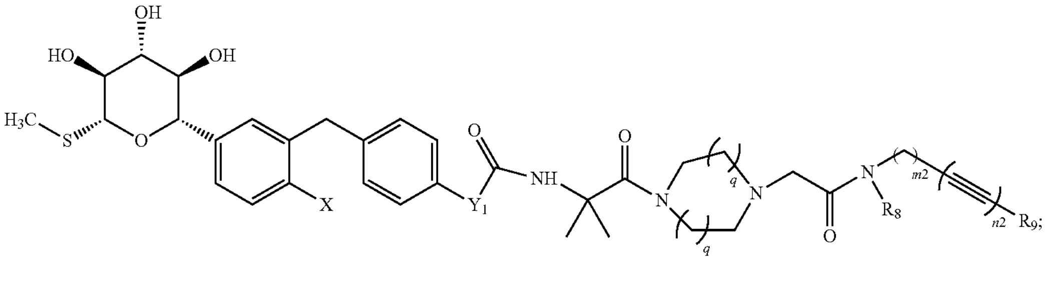

wherein, X is selected from hydrogen, deuterium, halogen, C1-C6 alkyl, C3-C6 cycloalkyl, C2-C6 alkenyl, and C2-C6 alkynyl;

$R_8$, $R_9$ and $R_{10}$ are each independently selected from hydrogen, deuterium, halogen, C1-C6 alkyl, cycloalkyl, cycloalkylalkyl or acyl, and C2-C8 alkynyl;

m2=0, 1, 2, 3;

n2=0, 1;

q=0, 1, 2, 3;

$Y_1$ is a linking group selected from the following structures:

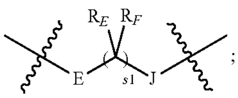

;

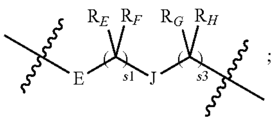

;

-continued

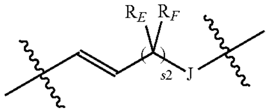

wherein, $R_E$, $R_F$, $R_G$ and $R_H$ are each independently selected from hydrogen, deuterium, halogen, C1-C6 alkyl or acyl;

E and J are each independently selected from chemical bonds, —$CH_2$—, oxygen, and —NH—;

s1=0, 1, 2, 3, 4, 5;

s2=0, 1, 2, 3, 4, 5; and s3=0, 1, 2, 3, 4, 5.

The present invention provides the compound of formula (I), comprising compounds of the following general structural formula structures (IV) and (V), stereoisomers, tautomers or pharmaceutically acceptable salts thereof, (VI)

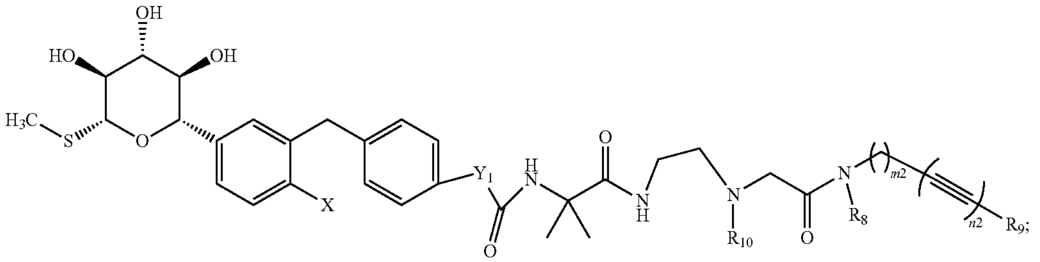

(V)

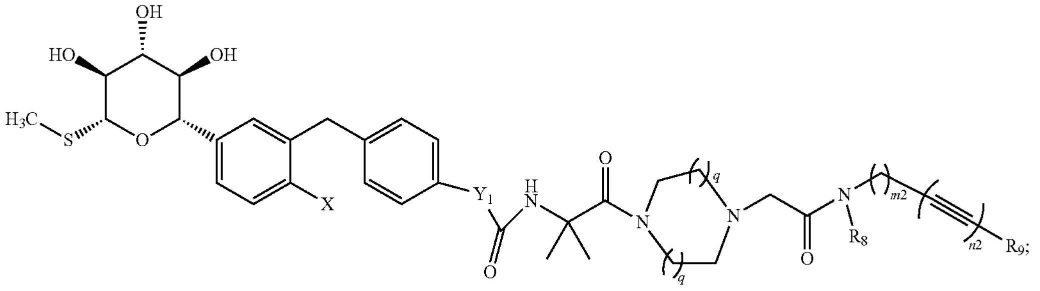

wherein, X is selected from hydrogen, deuterium, halogen, C1-C6 alkyl, C3-C6 cycloalkyl, C2-C6 alkenyl, and C2-C6 alkynyl;

$R_8$, $R_9$ and $R_{10}$ are each independently selected from hydrogen, deuterium, halogen, C1-C6 alkyl or acyl, and alkynylalkyl;

m2=0, 1, 2, 3;

n2=0, 1;

q=0, 1, 2, 3;

$Y_1$ is a linking group, which is a linking arm composed of 2 to 17 carbon, oxygen and nitrogen atoms, and selected from the following structure:

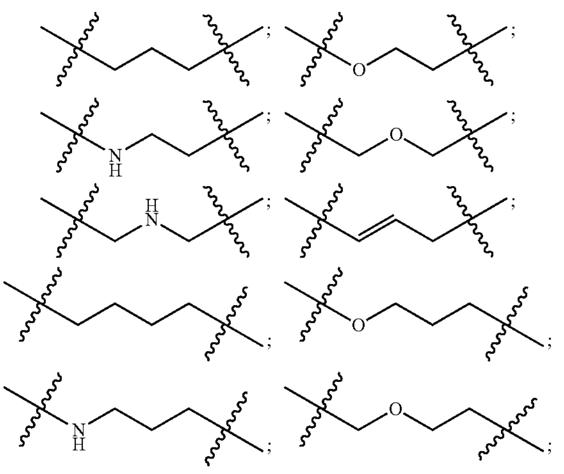

-continued

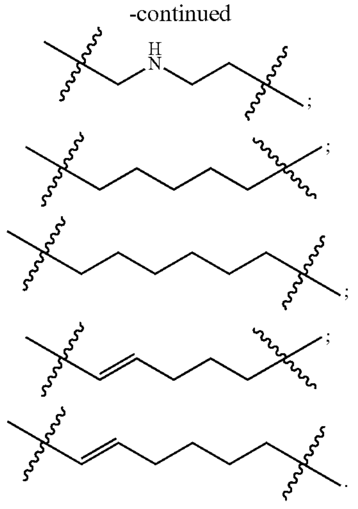

The present invention provides the compound of formula (II), wherein X is selected from hydrogen, deuterium, fluorine, bromine, iodine, methyl, ethyl, vinyl and ethynyl.

The present invention provides the compound of formula (II), wherein $R_9$ is selected from hydrogen, deuterium, fluorine, bromine, iodine, methyl, ethyl, C3~C8 cycloalkyl, vinyl and ethynyl.

The present invention provides following compounds, comprising compounds of following structures, stereoisomers, tautomers or pharmaceutically acceptable salts thereof,

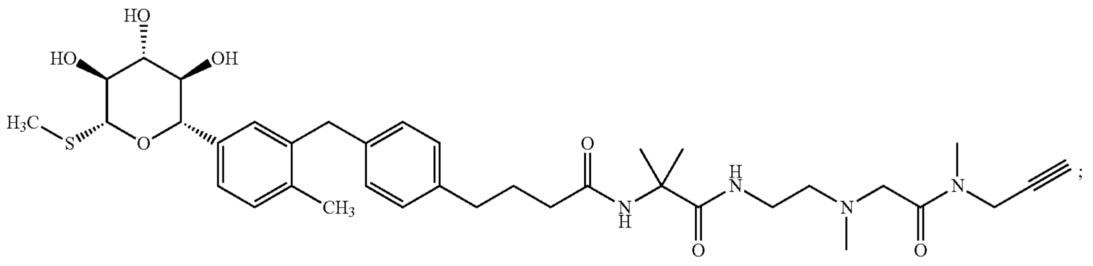

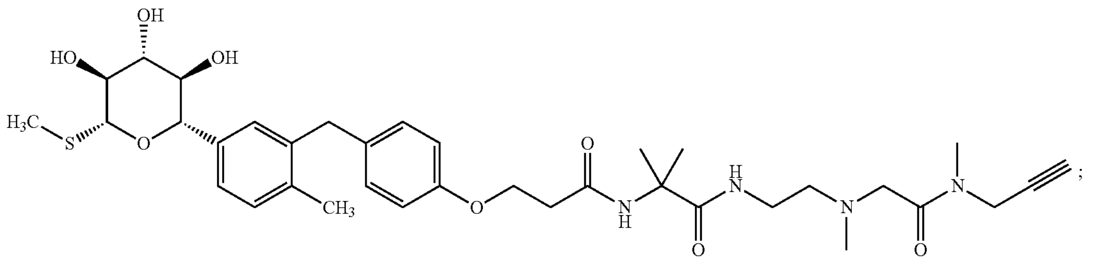

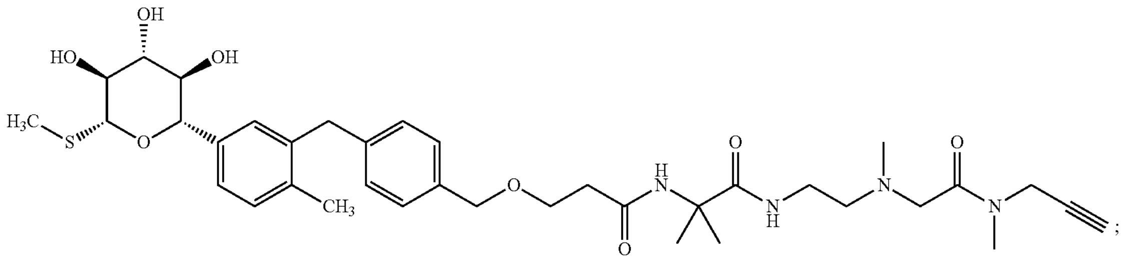

-continued
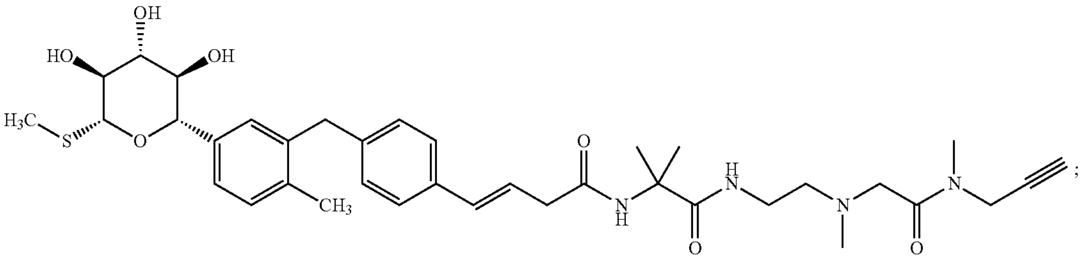
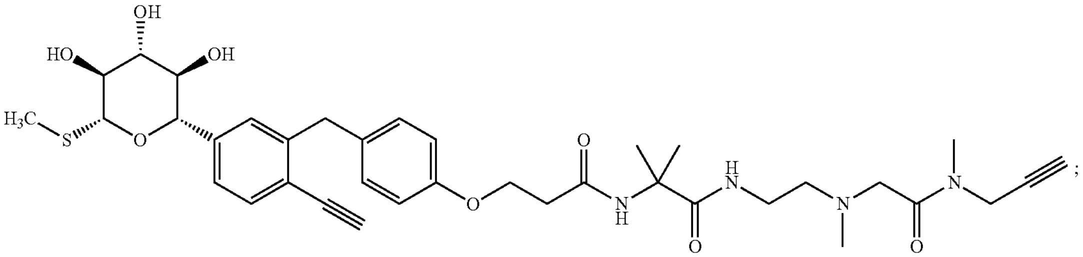
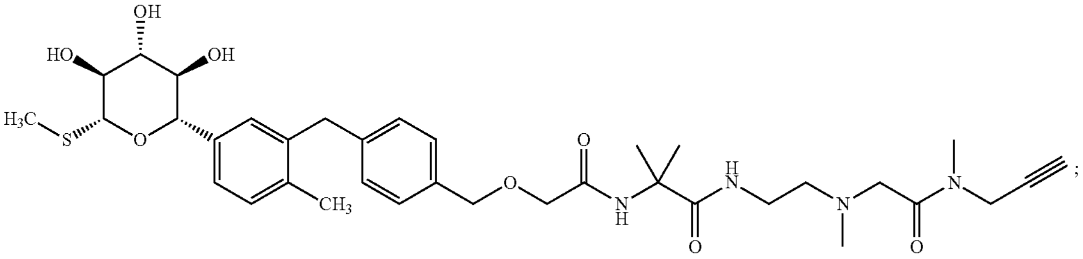
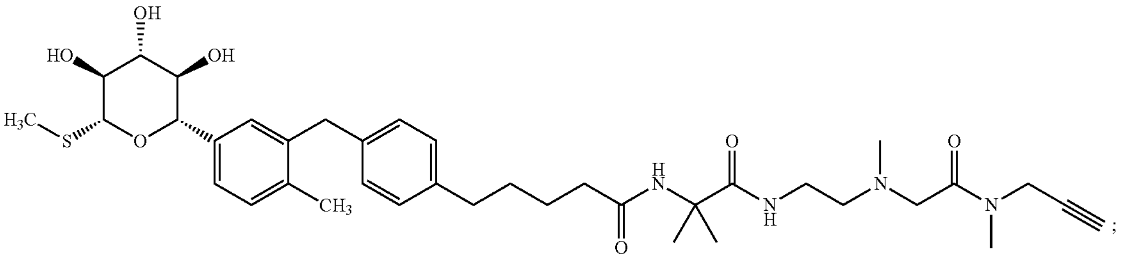
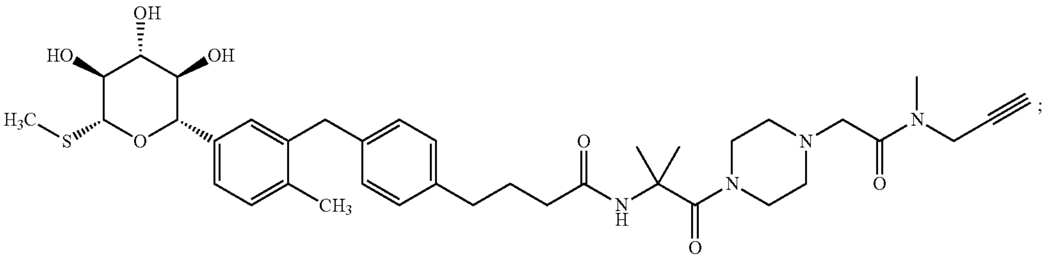
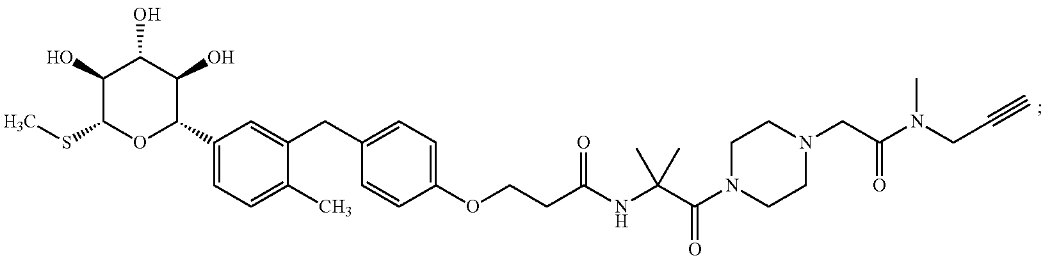

-continued

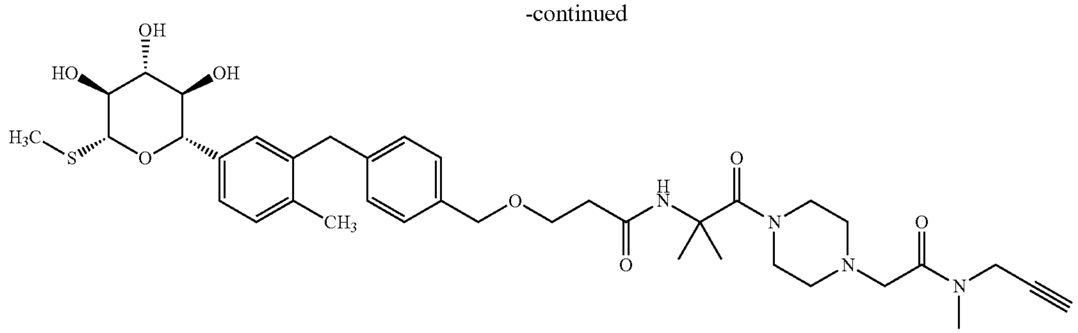

;

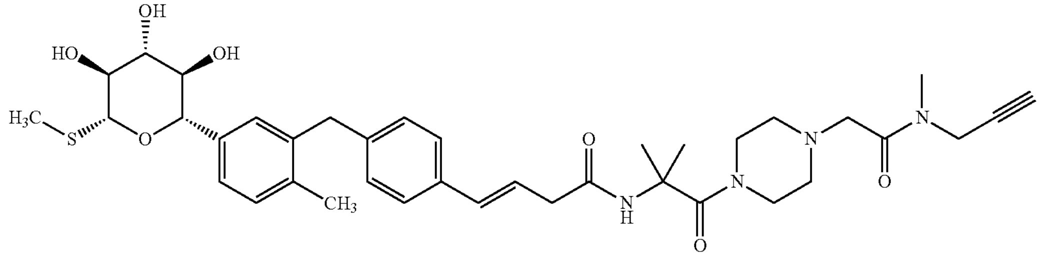

;

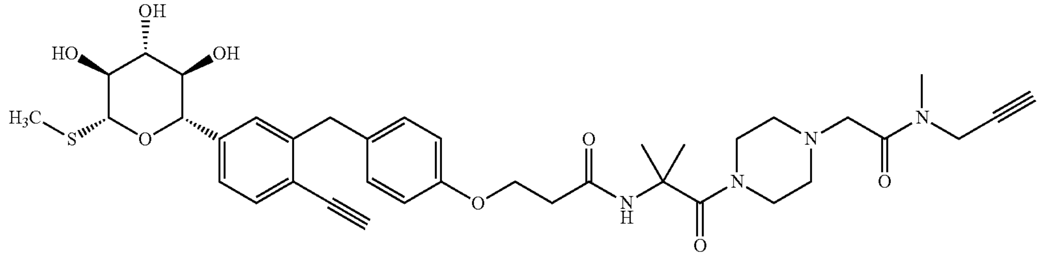

;

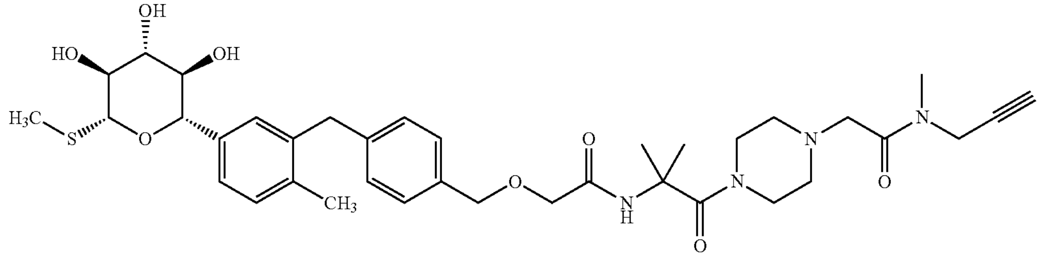

;

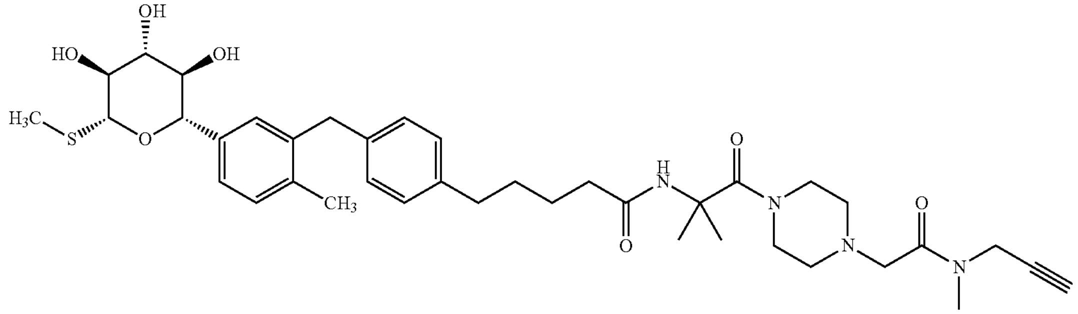

.

The present invention provides a pharmaceutical composition, comprising a therapeutically effective dose of the compound or the stereoisomer, the tautomer or the pharmaceutically acceptable salt thereof according to any item of the present invention, and a pharmaceutically acceptable carrier.

Use of the compound or the pharmaceutically acceptable salt thereof according to any item of the present invention or the pharmaceutical composition according to the present invention in the preparation for the treatment and improvement of diabetes, cardiovascular and cerebrovascular diseases, weight loss, fatty liver, metabolism-related diseases and in the treatment of tumors.

Use of the compound or the pharmaceutically acceptable salt thereof according to any item of the present invention or the pharmaceutical composition according to the present invention, as SGLT1/SGLT2 inhibitor, in the preparation of drugs or pharmaceutical compositions for the treatment of diseases related to SGLT1/SGLT2 function.

The use according to the present invention, wherein other therapeutic drugs already taken or currently taken by patients comprise hypotensive drugs, hypolipidemic drugs, antidiabetic drugs, hypoglycemic drugs, weight-loss drugs or appetite suppressants.

DETAILED DESCRIPTION OF THE INVENTION

Figure 1:
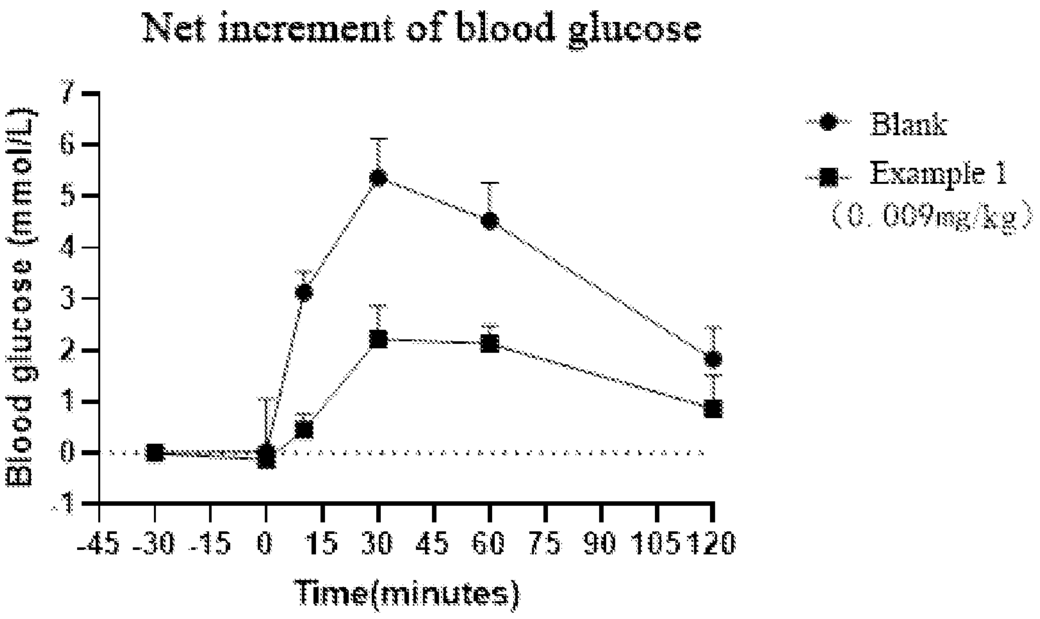
FIG. 1 shows results of oral glucose tolerance test (OGTT) after 14 days of continuous administration of the compound of example 1 in rats.
Figure 2:
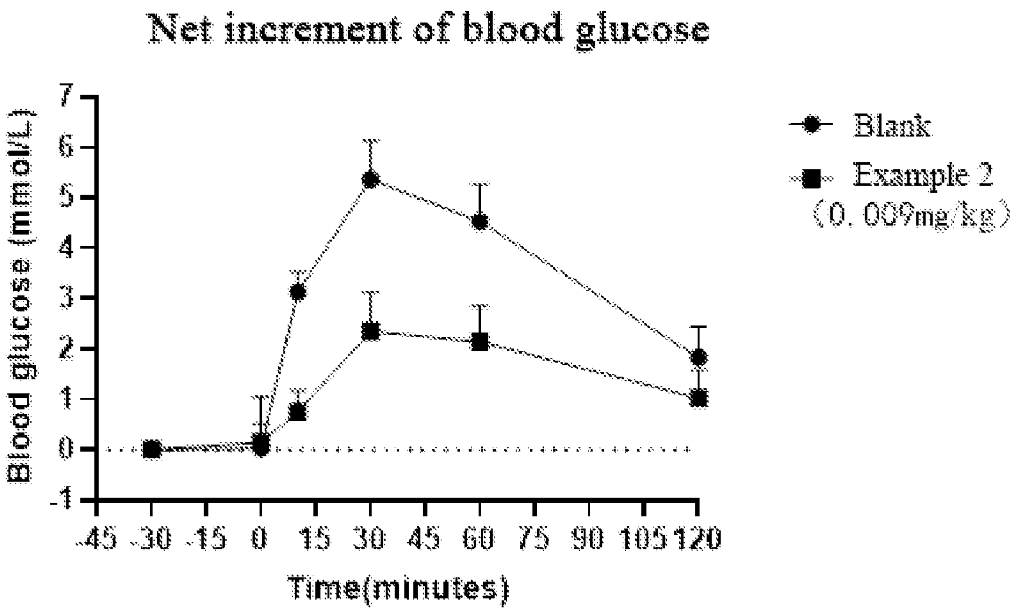
FIG. 2 shows results of oral glucose tolerance test (OGTT) after 14 days of continuous administration of the compound of example 2 in rats.
Figure 3:
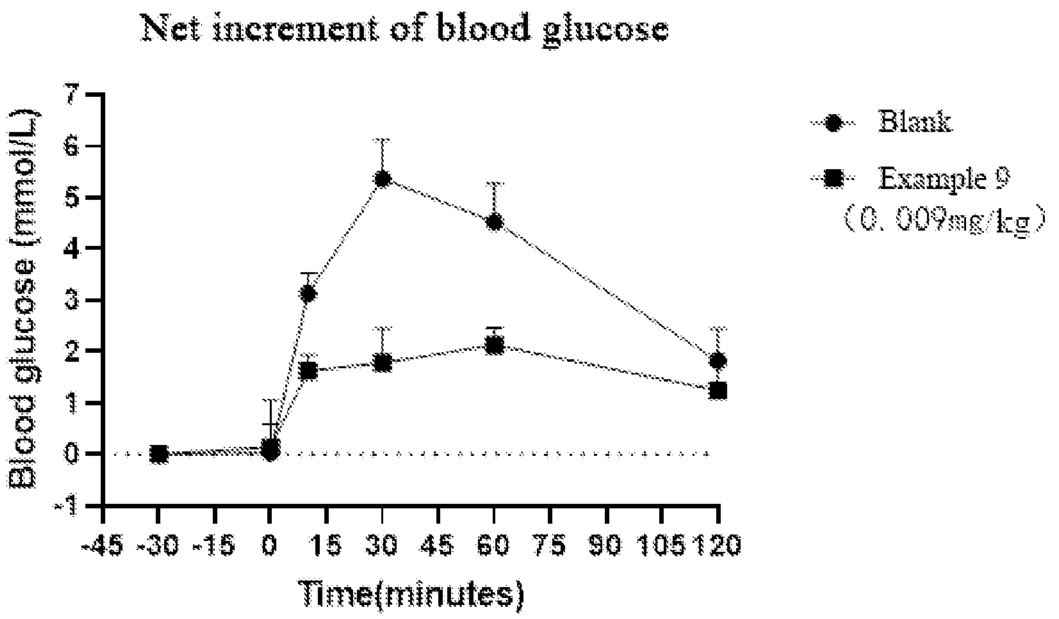
FIG. 3 shows results of oral glucose tolerance test (OGTT) after 14 days of continuous administration of the compound of example 9 in rats.
Figure 4:
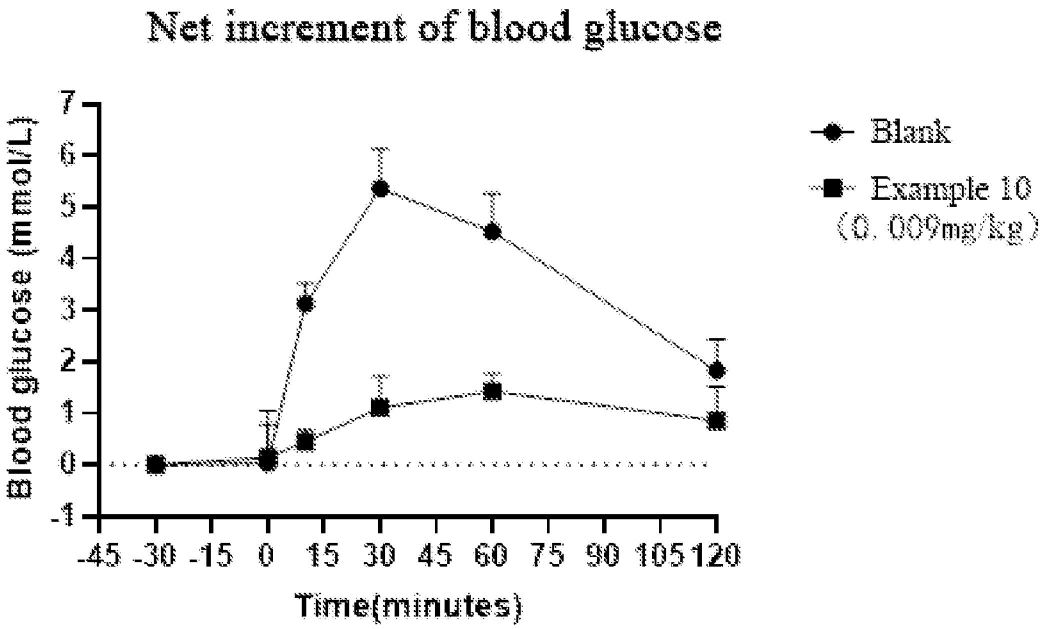
FIG. 4 shows results of oral glucose tolerance test (OGTT) after 14 days of continuous administration of the compound of example 10 in rats.
Figure 5:
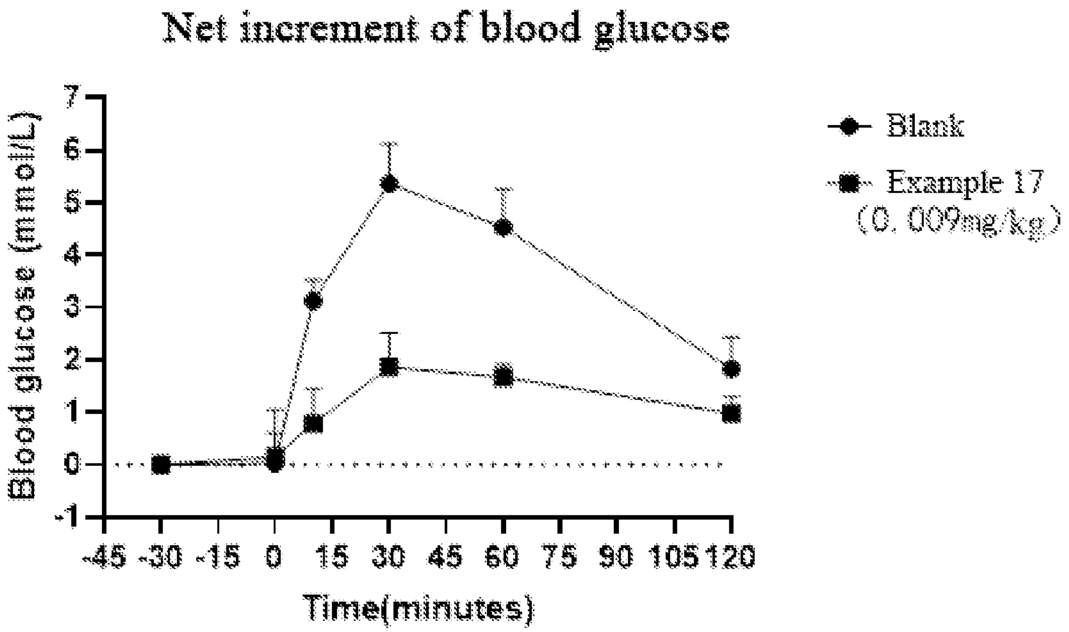
FIG. 5 shows results of oral glucose tolerance test (OGTT) after 14 days of continuous administration of the compound of example 17 in rats.

As used above and elsewhere herein, the following terms and abbreviations have the meanings defined below. If not defined, all technical and scientific terms used in this specification have the meanings commonly understood by one of ordinary skill in the art.

The term "hydrogen" refers herein to —H.

The term "halogen" refers herein to —F, —Cl, —Br and —I.

The term "fluoro" refers herein to —F.

The term "chloro" refers herein to —Cl.

The term "bromo" refers herein to —Br.

The term "iodo" refers herein to —I.

The term "cyano" refers herein to —CN.

The term "amino" refers herein to —$NH_2$.

The term "hydroxyl" refers herein to —OH.

The term "nitro" refers herein to —$NO_2$.

The term "carboxy" refers herein to —COOH.

The term "nitroso" refers herein to —NO.

The term "linking arm" herein refers to a chemical structure with a linking function composed of 2 to 17 carbon atoms, oxygen atoms, nitrogen atoms. Specifically, it refers to an alkane structure with a straight or branched chain structure (including saturated alkane, alkene and alkyne) or a similar alkane structure with a carbonyl group at one end; wherein, under the premise of forming a stable chemical structure, any carbon atom may be replaced by oxygen atom, nitrogen atom, and may also be further substituted by a substituent group, wherein the substituent group includes: fluoro, chloro, bromo, iodo, cyano, nitro, hydroxyl, carboxyl, amino, alkyl, alkoxy, acyl, acylamino, ester group, amido, sulfonyl, sulfinyl, cycloalkyl, cycloalkenyl, heterocycloalkyl, alkenyl, alkynyl and cycloalkoxy. The "linking arm" described herein include, but are not limited to, the following chemical structures:

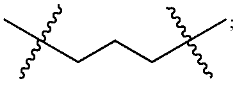 ; 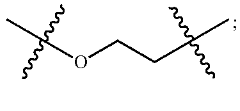 ;

-continued

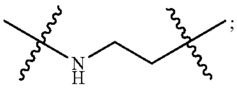 ; 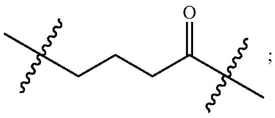 ;

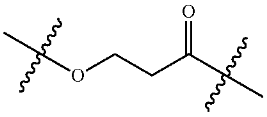 ; 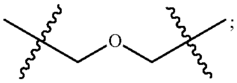 ;

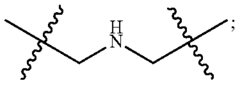 ; 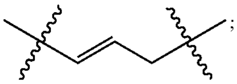 ;

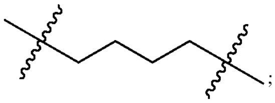 ; 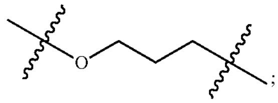 ;

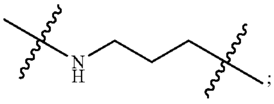 ; 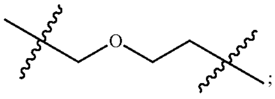 ;

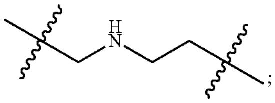 ;

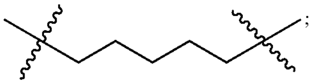 ;

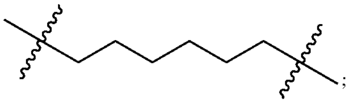 ;

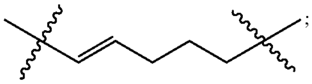 ;

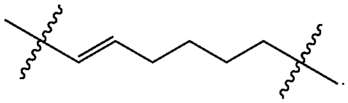 .

The term "aryl" herein refers to a 6- to 10-membered all-carbon monocyclic or fused polycyclic (i.e., ring that share adjacent pairs of carbon atoms) groups, polycyclic (i.e., ring with adjacent pairs of carbon atoms) group with a conjugated π electron system. Aryl groups may be covalently attached to the defined chemical structure at any carbon atom that results in a stable structure. The aryl groups described herein may be optionally substituted by one or more of the following substituents: fluoro, chloro, bromo, iodo, cyano, nitro, hydroxyl, carboxyl, amino, alkyl, alkoxy, acyl, acylamino, ester group, amido, sulfonyl, sulfinyl, cycloalkyl, cycloalkenyl, heterocycloalkyl, alkenyl, alkynyl and cycloalkoxy.

The term "heteroaryl" herein refers to an aromatic group composed of 5 to 10 atoms and containing at least one heteroatom selected from N, O or S and the like. The term may be a single ring (non-limiting examples include furan, thiophene, imidazole, pyrazole, pyridine, pyrazine, oxazole, thiazole, etc.) or multiple fused rings (non-limiting examples include benzothiophene, benzofuran, indole, isoindole, etc.), wherein the fused ring may or may not be an aromatic group containing a heteroatom, provided the linking point is through atoms of the aromatic heteroaryl group. The heteroaryl described herein may be optionally substituted by one or more of the following substituents: fluoro, chloro, bromo, iodo, cyano, nitro, hydroxy, amino, alkyl, alkoxy, acyl, acyloxy, acylamino, ester group, amido, sulfonyl, sulfinyl, cycloalkyl, cycloalkenyl, heterocycloalkyl, alkenyl, alkynyl and cycloalkoxy.

The term “cycloalkyl” herein refers to a cyclic alkyl group having 3 to 10 carbon atoms, having a monocyclic or polycyclic ring (including fused, bridged and spiro ring systems). Non-limiting examples of cycloalkyl groups include cyclopropyl, cyclobutyl, cyclopentyl, cyclohexyl, and the like. The cycloalkyl groups described herein may be optionally substituted by one or more of the following substituents: fluoro, chloro, bromo, iodo, cyano, nitro, hydroxy, carboxy, amino, alkyl, oxo, alkoxy, acyl, acyloxy, acylamino ester group, amido, cycloalkyl, cycloalkenyl, heterocycloalkyl, alkenyl, alkenyloxy, alkynyl, cycloalkoxy, aryl or heteroaryl.

The term “heterocyclyl” refers to a substituted or unsubstituted, saturated or unsaturated aromatic ring, non-aromatic ring containing at least 1 to 5 heteroatoms selected from N, O or S; the aromatic ring, non-aromatic ring may be 3- to 10-membered monocyclic ring, 4- to 20-membered spiro ring, bicyclic ring or bridged ring, selectively substituted N, S in the heterocyclyl ring may be oxidized to various oxidation states. A 3- to 12-membered heterocycle is preferred. Non-limiting examples include oxiranyl, oxetanyl, oxolanyl, oxanyl, oxanyl, oxocanyl, aziridinyl, azetidinyl, azolidinyl, azacyclohexyl, azacyclopropenyl, 1,3-dioxocyclopentyl, 1,4-dioxocyclopentyl, 1,3-dioxocyclopentyl, 1,3-dioxacyclohexyl, 1,3-dithiocyclohexyl, azacycloheptenyl, morpholinyl, piperazinyl, pyridyl, furyl, thienyl, pyrrolyl, pyranyl, N-alkylpyrrolyl, pyrimidinyl, pyrazinyl, pyridazinyl, imidazolyl, piperidinyl, thiomorpholinyl, dihydropyranyl, thiadiazolyl, oxazolyl, oxadiazolyl, pyrazolyl, 1,4-dioxacyclohexadienyl or the like.

The term “heterocycloalkyl” refers to a non-aromatic cycloalkyl group containing at least one heteroatom selected from O, N and S and optionally containing one or more double or triple bonds. The heterocycloalkyl group as a whole may have 3 to 10 ring atoms. The heterocycloalkyl group may be covalently attached to a defined chemical structure at any heteroatom or carbon atom that results in a stable structure. Non-limiting examples of the heterocycloalkyl group include: pyrrolinyl, piperidinyl, piperazinyl, tetrahydrofuranyl, tetrahydropyranyl, morpholinyl, pyranyl and the like. One or more N or S atoms on the heterocycloalkyl group may be oxidized (such as morpholine N-oxide, thiomorpholine S-oxide, thiomorpholine S,S-dioxide). The heterocycloalkyl group may also contain one or more oxo groups such as phthalimido, piperidinone group, oxazolidinone group, 2,4(1H,3H)-dioxo-pyrimidinyl, pyridine-2(1H)-keto group and the like. The heterocycloalkyl groups described herein may be optionally substituted by one or more of the following substituents: fluoro, chloro, bromo, iodo, cyano, nitro, hydroxy, carboxy, amino, alkyl, alkoxy, oxo, acyl, acyloxy, acylamino, ester group, amido, cycloalkyl, cycloalkenyl, heterocycloalkyl, alkenyl, alkenyloxy, alkynyl, cycloalkoxy, aryl or heteroaryl.

The term “alkenyl” herein refers to an alkenyl group having 2 to 8 carbon atoms and having at least one alkenyl unsaturated site. Non-limiting examples of the alkenyl groups include ethenyl, propenyl, allyl, isopropenyl, butenyl, isobutenyl, and the like. The alkenyl group described herein may be optionally substituted by one or more of the following substituents: deuterium, fluoro, chloro, bromo, iodo, cyano, nitro, hydroxyl, carboxyl, amino, alkyl, alkoxyl, acyl, acylamino, ester group, amido, sulfonyl, sulfinyl, cycloalkyl, cycloalkenyl, heterocycloalkyl, cycloalkoxy, mercapto, alkylmercapto, deuterated alkylmercapto, sulphonyl, sulfoxide group, amino, silyl, phosphonyl, deuterated alkyl, heterocycloalkyl, aryl, heteroaryl, alkynyl, alkenyl, arylalkyl, ester group.

The term “alkynyl” herein refers to an alkyl group in which two adjacent carbon atoms are joined by a triple bond, wherein the alkyl group is as defined herein. Alkynyl means an unsaturated alkyl group as defined above composed of at least two carbon atoms and at least one carbon-carbon triple bond, such as ethynyl, 1-propynyl, 2-propynyl, 1-, 2- or 3-butynyl, and the like. The alkynyl groups may be substituted or unsubstituted, and when substituted, the substituents are preferably one or more of the following groups which are independently selected from: deuterium, fluoro, chloro, bromo, iodo, cyano, nitro, hydroxyl, carboxyl, amino, alkyl, alkoxyl, acyl, acylamino, ester group, amido, sulfonyl, sulfinyl, cycloalkyl, cycloalkenyl, heterocycloalkyl, cycloalkoxy, mercapto, alkylmercapto, deuterated alkylmercapto, sulphonyl, sulfoxide group, amino, silyl, phosphonyl, deuterated alkyl, heterocycloalkyl, aryl, heteroaryl, alkynyl, alkenyl, arylalkyl, ester group.

The term “alkyl” herein refers to a saturated aliphatic hydrocarbyl group having from 1 to 10 carbon atoms, and the term includes both straight chain and branched chain hydrocarbyl groups. Non-limiting examples of the alkyl groups include methyl, ethyl, n-propyl, isopropyl, n-butyl, isobutyl, sec-butyl, tert-butyl, n-pentyl, neopentyl, n-hexyl, and the like. The alkyl groups described herein may be optionally substituted by one or more of the following substituents: fluoro, chloro, bromo, iodo, cyano, nitro, hydroxy, carboxyl, amino, alkyl, alkoxy, acyl, acyloxy, oxo, acylamino, ester group, amido, cycloalkyl, cycloalkenyl, heterocycloalkyl, alkenyl, alkenyloxy, alkynyl, cycloalkoxy, heterocycloalkyloxy, aryloxy, heteroaryloxy, aryl or heteroaryl.

The term “heteroalkyl” herein refers to an alkyl group that comprises at least one heteroatom.

The term “alkoxy” herein refers to an alkyl group attached to the remainder of the molecule through an oxygen atom (—O-alkyl), wherein the alkyl group is as defined herein. Non-limiting examples of the alkoxy groups include methoxy, ethoxy, trifluoromethoxy, difluoromethoxy, n-propoxy, isopropoxy, n-butoxy, t-butoxy, n-pentyloxy, and the like.

The term “acylamino” herein refers to —$NR^8$—C(O)-alkyl, —$NR^8$—C(O)-cycloalkyl, —$NR^8$—C(O)-cycloalkenyl, —$NR^8$—C(O)-aryl, —$NR^8$—C(O)-heteroaryl and —$NR^8$—C(O)-heterocycloalkyl, wherein $R^8$ is hydrogen, cycloalkyl, cycloalkenyl, aryl, heteroaryl, heterocycloalkyl and alkyl. Wherein, the groups such as hydrogen, cycloalkyl, cycloalkenyl, aryl, heteroaryl, heterocycloalkyl and alkyl are as defined herein.

The term “acyl” herein refers to H—C(O)—, $R^9R^{10}N$—C(O)—, alkyl-C(O)—, cycloalkyl-C(O)—, cycloalkenyl-C(O)—, heterocycloalkyl-C(O)—, aryl-C(O)— and heteroaryl-C(O)—, wherein the $R^9$ and $R^{10}$ are each independently selected from hydrogen, hydroxyl, alkyl, heterocycloalkyl, aryl, heteroaryl, sulfonyl, sulfinyl, cycloalkenyl, acyl or cycloalkyl. Wherein, the groups such as hydrogen, hydroxy, alkyl, heterocycloalkyl, aryl, heteroaryl, sulfonyl, sulfinyl, cycloalkenyl, acyl and cycloalkyl are as defined herein.

The term “oxo” refers to the description of the oxidation state of carbon atoms, nitrogen atoms, sulfur atoms, and the like by oxygen atoms, the representative structures formed after the oxidation of carbon atoms, nitrogen atoms, sulfur atoms, and the like by oxygen atoms include but are not limited to functional groups such as hydroxyl, alkoxy, carbonyl, oxynitride, sulfoxide, and sulphone.

The term "sulfonyl" herein refers to $R^{11}R^{12}N$—$S(O)_2$—, cycloalkyl-$S(O)_2$—, cycloalkenyl-$S(O)_2$—, aryl-$S(O)_2$—, heteroaryl-$S(O)_2$—, heterocycloalkyl-$S(O)_2$— and alkyl-S $(O)_2$—, wherein the $R^{11}$ and $R^{12}$ are each independently selected from hydrogen, hydroxyl, alkyl, heterocycloalkyl, aryl, heteroaryl, sulfonyl, sulfinyl, cycloalkenyl, acyl or cycloalkyl. Wherein, the groups such as hydrogen, hydroxy, alkyl, heterocycloalkyl, aryl, heteroaryl, sulfonyl, sulfinyl, cycloalkenyl, acyl and cycloalkyl are as defined herein.

The term "sulfinyl" herein refers to $R^{13}R^{14}N$—S(O)—, cycloalkyl-S(O)—, cycloalkenyl-S(O)—, aryl-S(O)—, heteroaryl-S(O)—, heterocycloalkyl-S(O)— or alkyl-S(O)—, wherein the $R^{13}$ and $R^{14}$ are each independently selected from hydrogen, hydroxyl, alkyl, heterocycloalkyl, aryl, heteroaryl, sulfonyl, sulfinyl, cycloalkenyl, acyl or cycloalkyl. Wherein, the groups such as hydrogen, hydroxy, alkyl, heterocycloalkyl, aryl, heteroaryl, sulfonyl, sulfinyl, cycloalkenyl, acyl and cycloalkyl are as defined herein.

The term "acyloxy" herein refers to —O—C(O)-alkyl, —O—C(O)-cycloalkyl, —O—C(O)-cycloalkenyl, —O—C (O)-aryl, —O—C(O)-heteroaryl and —O—C(O)-heterocycloalkyl, wherein the groups such as alkyl, cycloalkyl, cycloalkenyl, aryl, heteroaryl and heterocycloalkyl are as defined herein.

The term "ester group" herein refers to alkyl-O—C(O)—, cycloalkyl-O—C(O)—, cycloalkenyl-O—C(O)—, heterocycloalkyl-O—C(O)—, aryl-O—C(O)— and heteroaryl-O—C(O)—, wherein the groups such as alkyl, cycloalkyl, cycloalkenyl, heterocycloalkyl, aryl and heteroaryl are as defined herein.

The term "optional" or "optionally" means that the subsequently described event or circumstance may, but does not necessarily, occur, and this description includes cases in which the event or circumstance occurs and does not occur.

The term "optionally substituted by . . . " means that the structure is unsubstituted or substituted by one or more substituents described in the present invention. The term "substitution" herein means the single or multiple substitution of any group by a designated substituent to the extent that such single or multiple substitution (including multiple substitutions in the same moiety) is chemically permissible, wherein each substituent can be located at any available position on the group and can be attached through any available atom on the substituent. "Any available position" refers to any position on the group, which is chemically obtainable by methods known in the art or as taught herein and does not create molecules that are excessively unstable. When there are two or more substituents on any group, each substituent is defined independently of any other substituent and thus may be the same or different.

In various parts of the specification, substituents of the compounds of the present invention are disclosed in the form of groups or ranges. This specifically means that the present invention encompasses each of the members of such groups or ranges or subgroups of each of the members. The term "$C_{1-6}$ alkyl" specifically means that methyl, ethyl, $C_3$ alkyl, $C_4$ alkyl, $C_5$ alkyl and $C_6$ alkyl are disclosed separately.

The term "compounds of the present invention" (unless otherwise specifically indicated) herein refers to compounds of formula (I) and formula (II) and all pure and mixed stereoisomers, geometric isomers, tautomers, solvates, prodrugs and isotopically labeled compounds and any pharmaceutically acceptable salts thereof. The solvate of the compound of the present invention means a compound or a salt thereof combined with a stoichiometric and non-stoichiometric solvent, such as a hydrate, an ethylate, a methylate, an acetonate or the like. The compound may also be present in one or more crystalline states, i.e., as a co-crystal, a polymorph, or it may be present as an amorphous solid. All such forms are covered by the claims.

The term "pharmaceutically acceptable" means that the substance or composition must be chemically and/or toxicologically compatible with the other ingredients that make up the formulation and/or the mammal treated by it.

The term "stereoisomer" herein refers to compounds with different chiral properties having one or more stereocenters, including the enantiomers and diastereomers.

The term "tautomer" herein refers to structural isomers with different energies that can cross the low energy barrier and thus convert to each other. One example is proton tautomers including tautomers that interconvert by proton transfer, such as enol-keto tautomers and imine-enamine tautomers, or a tautomeric form of a heteroaryl group containing a ring atom attached to ring-NH-moiety and ring=N-moiety, such as pyrazole, imidazole, benzimidazole, triazole and tetrazole. Valence tautomers include those in which some bonding electrons recombine to interconvert.

The term "prodrug" herein refers to any derivative of the compound of the present invention that, when administered to a subject, directly or indirectly provides the compound of the present invention, an active metabolite or residue thereof. Especially preferred are those derivatives or prodrugs that increase the bioavailability, metabolic stability and tissue targeting of the compounds of the present invention.

The compounds of the present invention may be used in the form of salts, such as "pharmaceutically acceptable salts" derived from inorganic or organic acids. These include, but are not limited to, the following substances: acetate, adipate, alginate, citrate, aspartate, benzoate, besylate, ethanesulfonate, disulfate, butyrate, camphorate, camphorsulfonate, digluconate, cyclopentane propionate, lauryl sulfate, ethanesulfonate, glucoheptonate, glycerophosphate, hemisulphate, heptanoate, hexanoate, fumarate, hydrochloride, hydrobromide, hydroiodide, 2-hydroxyethanesulfonate, lactate, maleate, methanesulfonate, ethanesulfonate, hydrochloride, 2-naphthalene sulfonate, oxalate, pectate, sulfate, 3-phenylpropionate, picrate, trimethylacetate, propionate, succinate, tartrate, thiocyanate, p-toluenesulfonate and decanoate. In addition, basic nitrogen-containing groups can be quaternized with the following reagents to form quaternary ammonium salts: such as lower alkyl halide, including chloride, bromide and iodide of methyl, ethyl, propyl and butyl groups; such as dialkylsulfate, including dimethylsulfate, diethylsulfate, dibutylsulfate and dipentylsulfate; such as long chain halide, including chloride, bromide and iodide of decyl, lauryl, myristyl, and stearyl; such as aralkyl halide, such as bromide of benzyl and phenethyl, and the like.

The present invention also includes isotopically labeled compounds of the present invention, which are identical to those disclosed above in structure, but in which one or more atoms are replaced by an atom having the same number of protons but a different number of neutrons. Examples of the isotope incorporating into the compounds of the present invention include isotopes of hydrogen, carbon, nitrogen, oxygen, sulfur, fluorine, chlorine and iodine, such as $^{2}H$, $^{3}H$, $^{13}C$, $^{14}C$, $^{15}N$, $^{18}O$, $^{17}O$, $^{35}S$, $^{18}F$, $^{36}Cl$ and $^{131}I$, etc.

The compounds of the present invention, stereoisomers, tautomers or pharmaceutically acceptable salts thereof, and the compounds of the above forms containing the above isotopes and/or isotopes of other atoms are all within the scope of the present invention. Certain isotopically labeled compounds of the present invention, such as those labeled with $^{3}H$ or $^{14}C$, can be used in drug tissue distribution assays, and therefore, these $^{3}H$ or $^{14}C$ isotopes are particularly preferred because of their ease of preparation and detection. In addition, certain compounds of the present invention replaced by heavier isotopes such as $^{2}H$ have certain therapeutic advantages due to better metabolic stability, such as increased in vivo half-life and lower doses, etc., therefore, $^{2}H$ is also preferred in some cases.

EMBODIMENTS

The following examples are used to further illustrate the present invention, but the present invention is not limited thereto. Throughout the present application, various examples of the compounds and methods of the present invention are referred herein. The various examples described are intended to provide a number of illustrative examples and should not be construed as a description of alternatives. At the same time, it should be noted that the examples (including various methods and parameters) discussed herein are merely intended to illustrate the invention and do not limit the scope of protection of the invention by any means. For the purpose of describing the present invention, specific examples are set forth below. However, it is to be understood that the present invention is not limited to these examples, and the following examples are merely intended to provide a method of practicing the present invention and do not limit the scope of the present invention by any means.

A preparation method of a compound of formula (I) in any item of the present invention, a stereoisomer, tautomer or pharmaceutically acceptable salt thereof, comprises the following steps, Scheme 1:

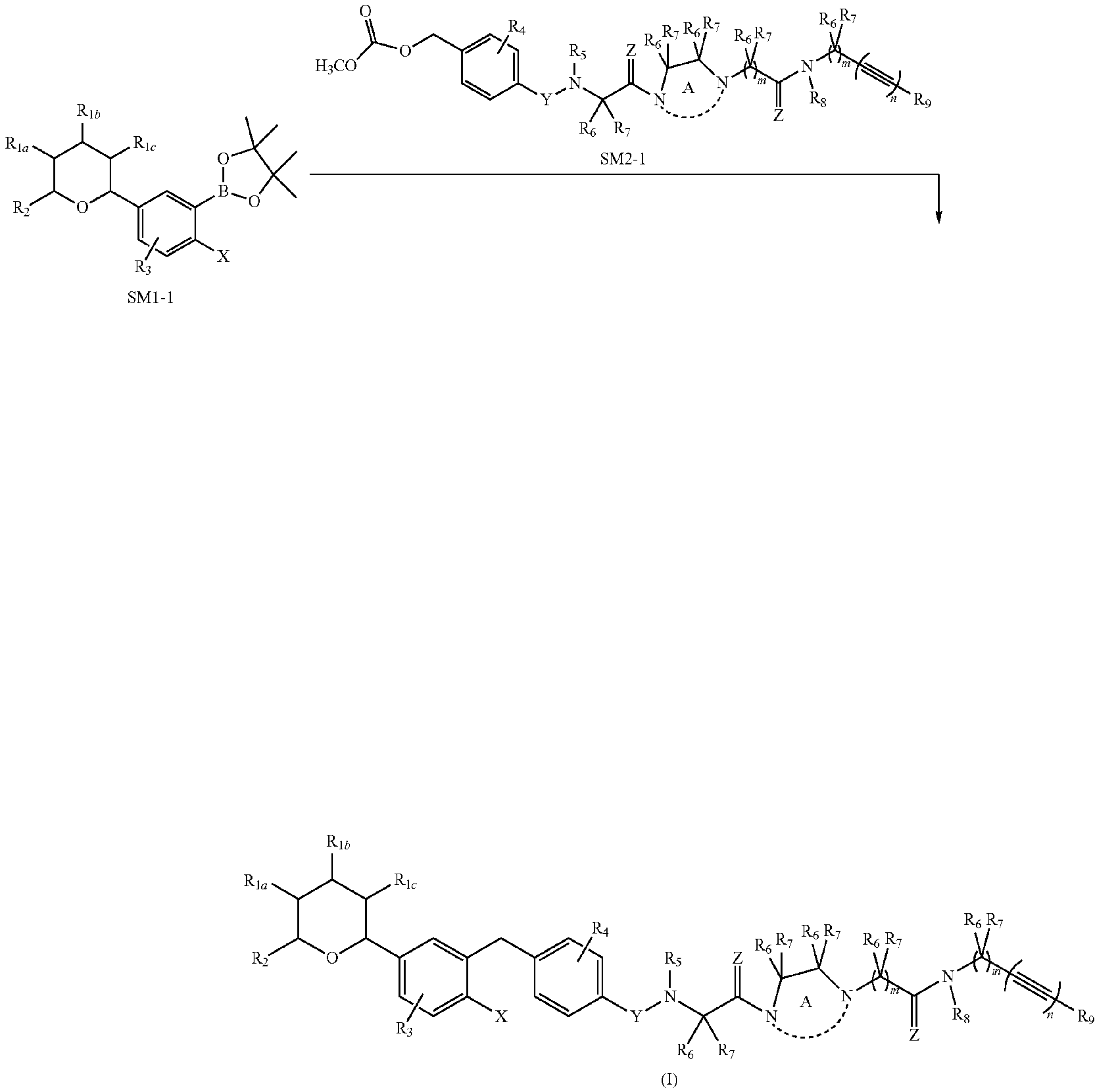

SM2-1

SM1-1

(I)

SM1-1 and SM2-1 are reacted under certain chemical reaction conditions to prepare the compound of general formula (I), wherein each substituent is defined as before;

alternatively, the preparation method of the compound of formula (I) according to any one of the present invention, the stereoisomer, tautomer or pharmaceutically acceptable salt thereof, comprises the following steps, scheme 2:

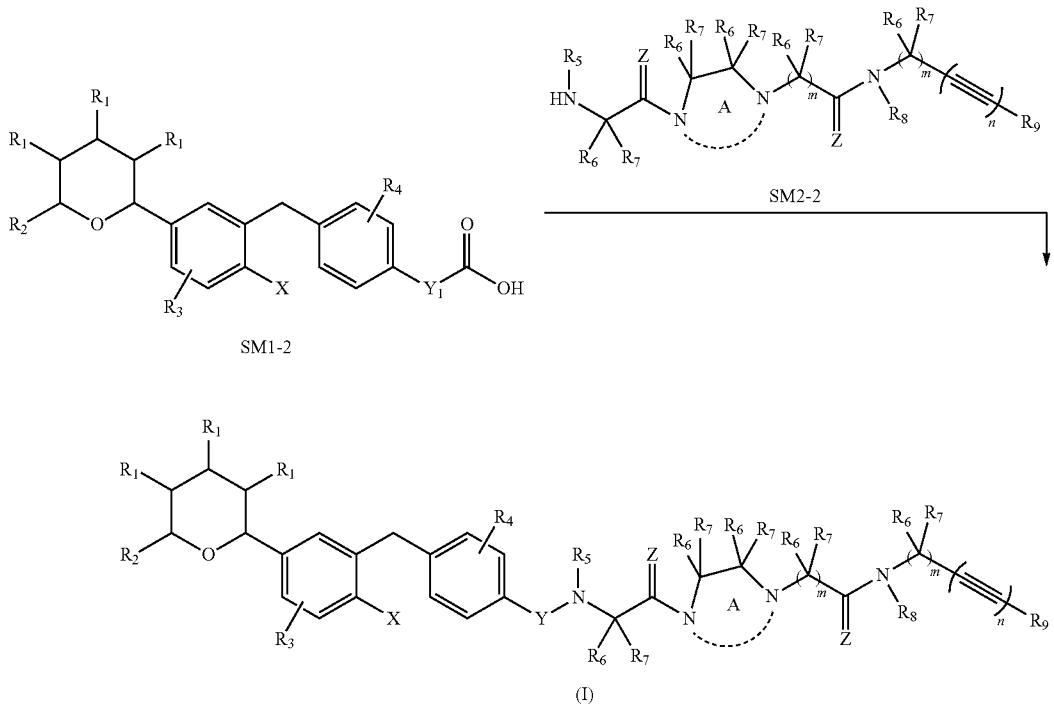

SM1-2 and SM2-2 are reacted under certain chemical reaction conditions to prepare the compound of general formula (I), wherein each substituent is defined as before.

The compounds provided by the present invention can be prepared by standard synthetic methods well known in the art, and this specification provides general methods for preparing the compounds of the present invention. The starting materials are usually commercially available, for example, purchased from companies such as Alfa Aesar®, Sigma-Aldrich®, TCI, J&K®, Shaoyuan Chemical, Energy Chemical, etc., or prepared by methods well known to those skilled in the art.

The compounds of the present invention and the corresponding preparation methods are further explained and listed below by means of examples and preparations. It should be understood that although typical or preferred reaction conditions (such as reaction temperature, time, molar ratio of reactants, reaction solvent and pressure, etc.) are given in the specific examples, other reaction conditions may also be used by those skilled in the art. Optimal reaction conditions may vary with the particular reaction substrates or solvents used, but such conditions can be determined by one skilled in the art through routine optimization.

The structures of the compounds in the following examples were characterized by nuclear magnetic resonance (NMR) and/or mass spectrometry (MS). NMR spectrometer was used, the compound was dissolved in appropriate deuterated reagents and analyzed by $^1$H-NMR at ambient temperature with TMS as an internal standard. NMR chemical shifts (S) were measured in ppm and the following abbreviations were used: s, singlet; d, doublet; t, triplet; q, quartet; m, multiplet; brs, broad singlet. MS was determined by mass spectrometer (ESI).

The starting materials of the reaction, intermediates and the compounds of examples can be separated and purified by conventional techniques such as precipitation, filtration, crystallization, evaporation, distillation and chromatography (such as column chromatography, TLC separation and purification, etc.) and the like.

HSGF254 thin layer chromatography silica gel plate (0.2±0.03 mm) was used for TLC, and HSGF254 thin layer chromatography thick preparation plate (0.9 mm-1 mm) was used for TLC separation and purification. 300-400 mesh silica gel was used as the carrier for column chromatography.

Commercial solvents and reagents used in the test, unless otherwise specified, can be used directly without further purification or treatment after purchase. When referring to other examples or synthetic methods, the reaction conditions (reaction temperature, reaction solvent, molar ratio of reactants or/and reaction duration) may be different. In general, the progress of the reaction can be monitored by TLC, and the appropriate time can be selected to terminate the reaction and carry out post-treatment accordingly. The purification conditions of the compounds may also vary, in general, an appropriate column chromatography eluent is selected according to the $R_f$ value of TLC, or the corresponding compounds are separated and purified by preparative TLC.

Preparation of Intermediates

Intermediate: 4-(4-(2-methyl-5-(2S,3R,4R,5S,6R)-3,4,5-trihydroxy-6-(methylthio)tetrahydro-2H-pyran-2-yl)benzyl)phenyl)butyric acid

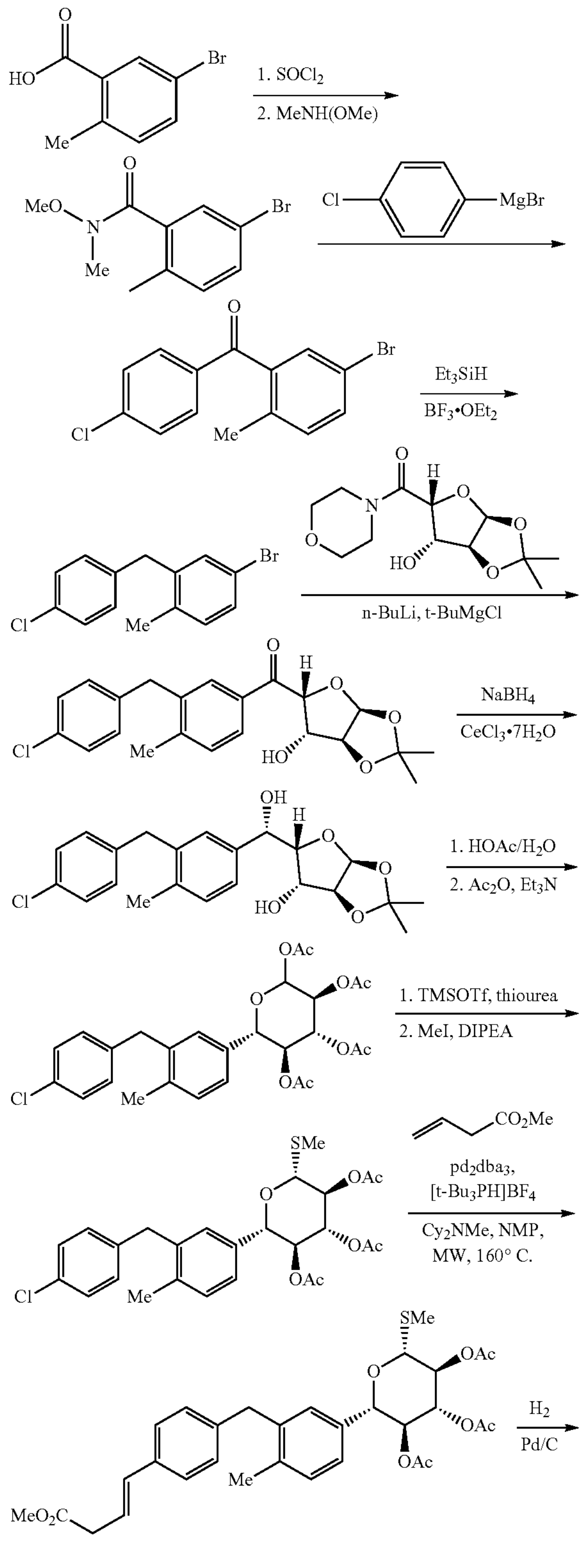

-continued

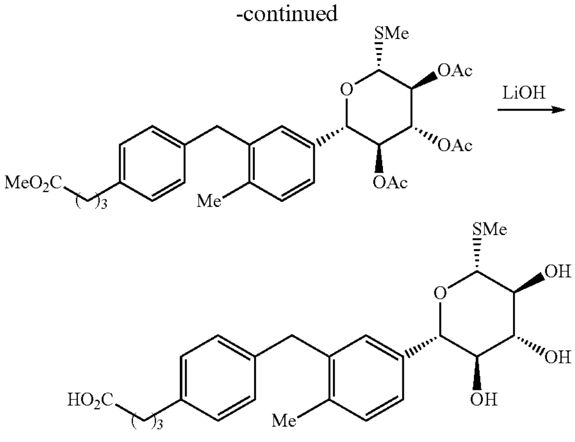

5-Bromo-N-methoxy-N,2-dimethylbenzamide

5-Bromo-2-methylbenzoic acid (24.0 g) and dichloromethane (600 ml) were added into a 1 L reaction flask, dropwise added with dimethyl sulfoxide (16.2 ml) and N,N-dimethylformamide (3.6 ml) successively, then returned to room temperature and stirred for 3 h after dropping. The reaction solution was concentrated to dryness, added with dichloromethane (190 ml), and N,O-dimethylhydroxylamine hydrochloride (31.0 g) successively, cooled to 0° C. in an ice bath, and dropwise added with triethylamine (46.5 ml). After addition, the solution was returned to room temperature and stirred for 15 h. The reaction solution was poured into 1M diluted hydrochloric acid, and subjected to liquid separation. The aqueous phase was extracted twice with dichloromethane, and the organic phases were combined, washed with saturated salt solution solution, dried with anhydrous sodium sulfate, filtered, and concentrated under reduced pressure. The concentrate was purified by column chromatography to obtain 23.1 g of colorless liquid.

(5-Bromo-2-methylphenyl)(4-chlorophenyl)methanone

The product of the previous step (18.7 g) and tetrahydrofuran (150 ml) were added into a 500 ml reaction flask, cooled to 0° C., dropwise added with 4-chlorophenylmagnesium bromide (1M in $Et_2O$), and stirred at room temperature for 2 h after dropping. The reaction solution was poured into saturated aqueous ammonium chloride solution, and extracted with ethyl acetate for three times. The organic phases were combined, washed with saturated salt solution, dried with anhydrous sodium sulfate, filtered, concentrated under reduced pressure, and purified by column chromatography to obtain 18.0 g of white solid. $^1H$ NMR (400 MHz, $CDCl_3$): δ 7.76 (m, 2H), 7.54 (dd, J=2.1, 8.2 Hz, 1H), 7.48 (m, 2H), 7.43 (d, J=2.1 Hz, 1H), 7.20 (d, J=8.2 Hz, 1H), 2.27 (s, 3H).

4-Bromo-2-(4-chlorobenzyl)-1-toluene (5-Bromo-2-methylphenyl)(4-chlorophenyl)methanone (23.0 g), acetonitrile (230 ml) and triethylsilane (52.9 ml, 331.2 mmol) were added into a 500 ml reaction flask, cooled to 0° C., slowly dropwise added with boron trifluoride ether (54.6 ml), kept stirring at 0° C. for 30 min after addition, and then heated to 65° C. and stirred for 2 h. After the reaction was completed, the reaction solution was cooled to 0° C., slowly added with saturated aqueous sodium bicarbonate solution until no bubbles were generated, and extracted with ethyl acetate for three times. The organic phases were combined, washed with saturated salt solution, dried with anhydrous sodium sulfate, filtered, and concentrated under reduced pressure, and purified by column chromatography (eluting with petroleum ether) to obtain 18.5 g of white solid.

(3-(4-Chlorobenzyl)-4-methylphenyl)((3aS,5R,6S,6aS)-6-hydroxy-2,2-dimethyltetrahydrofuro[2,3-d][1,3]dioxol-5-yl)methanone (3aS,5R,6S,6aS)-6-Hydroxy-2,2-dimethyltetrahydrofuro[2,3-d][1,3]dioxol-5-yl)(morpholinyl)methanone (14.3 g) and tetrahydrofuran (150 ml) were added into a 500 ml reaction flask, cooled to 0° C., dropwise added with tert-butylmagnesium chloride (1M in THF, 57.5 ml, 57.5 mmol). After addition, the mixture was continued to stir for 30 min.

4-Bromo-2-(4-chlorobenzyl)-1-toluene (18.5 g) and tetrahydrofuran (180 ml) were added into a 1 L reaction flask under nitrogen protection, cooled to −78° C., and then slowly dropwise added with n-butyllithium (1.6 M in hexane) and stirred for 10 min. Then, the newly prepared Grignard reaction solution above was added, and after addition, the mixture was returned to room temperature and continued to stir for 1 h. After the reaction was completed, the reaction solution was poured into saturated aqueous ammonium chloride solution, and extracted with ethyl acetate for three times. The organic phases were combined, washed with saturated salt solution, dried with anhydrous sodium sulfate, filtered, concentrated under reduced pressure, and purified by column chromatography to obtain 14.2 g of white solid. $^1$H NMR (400 MHz, $CDCl_3$): δ 7.90-7.88 (dd, J=1.8, 7.9 Hz, 1H), 7.77 (d, J=1.6 Hz, 1H), 7.32-7.30 (d, J=8.0 Hz, 1H), 7.28-7.26 (m, 2H), 7.08-7.06 (d, J=8.4 Hz, 2H), 6.10 (d, J=3.6 Hz, 1H), 5.31 (d, J=2.7 Hz, 1H), 4.61 (d, J=3.6 Hz, 1H), 4.58 (s, 1H), 4.02 (s, 2H), 3.09 (s, 1H), 2.31 (s, 3H), 1.57 (s, 3H), 1.38 (s, 3H).

(3aS,5S,6R,6aS)-5-((s)-(3-(4-chlorobenzyl)-4-methylphenyl)(hydroxy)methyl)-2,2-dimethyltetrahydrofuro[2,3-d][1,3]dioxol-6-ol (3aS,5R,6S,6aS)-6-Hydroxy-2,2-dimethyltetrahydrofuro[2,3-d][1,3]dioxol-5-yl)(morpholinyl)methanone (14.2 g), cerium chloride heptahydrate (15.7 g) and methanol (280 ml) were added into a 500 ml reaction flask, cooled to 0° C. in an ice bath, and then slowly dropwise added with a solution (16 ml) of sodium borohydride (1.6 g) in 1M aqueous sodium hydroxide. After the addition, the mixture was returned to room temperature and stirred for 1 h. The reaction solution was poured into saturated aqueous ammonium chloride solution, and extracted with ethyl acetate for three times. The organic phases were combined, washed with saturated salt solution, dried with anhydrous sodium sulfate, filtered, and concentrated under reduced pressure to obtain 13.0 g of pale yellow solid, which was directly used in the next reaction.

(3S,4R,5S,6S)-6-(3-(4-Chlorobenzyl)-4-methylphenyl)tetrahydro-2H-pyran-2,3,4,5-tetrayl tetraacetate (3aS,5S,6R,6aS)-5-((s)-(3-(4-chlorobenzyl)-4-methylphenyl)(hydroxy)methyl)-2,2-dimethyltetrahydrofuro[2,3-d][1,3]dioxol-6-ol (13.0 g), glacial acetic acid (65 ml) and water (65 ml) were added into a 500 ml reaction flask, heated to 110° C. and stirred for 4 h. The reaction solution was concentrated to dryness, and azeotropically distilled with toluene for three times. The residue was dissolved in 130 ml of acetonitrile, and then added with triethylamine (44.5 ml), and a solution (65 ml) of acetic anhydride (30.1 ml) in acetonitrile was slowly added dropwise at 35° C. under nitrogen protection. After addition, the mixture was cooled to room temperature naturally and stirred for 15 h. The reaction solution was diluted with ethyl acetate, added with water, and subjected to liquid separation. The aqueous phase was extracted with ethyl acetate for three times. The organic phases were combined, washed once with diluted hydrochloric acid and saturated salt solution in turn, dried with anhydrous sodium sulfate, filtered, and concentrated under reduced pressure, purified by column chromatography to obtain 14.6 g of yellow solid. $^1$H NMR (400 MHz, $CDCl_3$): δ 7.26-7.23 (m, 2H), 7.19-7.14 (m, 2H), 7.09 (s, 1H), 7.01 (d, J=8.5 Hz, 2H), 5.88 (d, J=8.2 Hz, 1H), 5.37 (t, J=9.5 Hz, 1H), 5.28 (t, J=8.9 Hz, 1H), 5.20 (t, J=9.6 Hz, 1H), 4.50 (d, J=9.9 Hz, 1H), 3.98-3.90 (m, 2H), 2.18 (s, 3H), 2.12 (s, 3H), 2.08 (s, 3H), 2.03 (s, 3H), 1.78 (s, 3H).

(2S,3S,4R,5S,6R)-2-(3-(4-Chlorobenzyl)-4-methylphenyl)-6-(methylthio)tetrahydro-2H-pyran-3,4,5-triyl triacetate (3S,4R,5S,6S)-6-(3-(4-Chlorobenzyl)-4-methylphenyl)tetrahydro-2H-pyran-2,3,4,5-tetrayl tetraacetate (14.6 g), thiourea (4.2 g), 1,4-dioxane (150 ml), and trimethylsilyl trifluoromethanesulfonate (9.9 ml) were added into a 500 ml reaction flask, heated to 90° C. and stirred for 2 h. After the reaction was completed, the solution was cooled to room temperature, added with iodomethane (5.1 ml) and N,N-diisopropylethylamine (27.1 ml) successively, and then stirred at room temperature for 15 h. Ethyl acetate and water were added, stirred, and liquid separation was carried out. The aqueous phase was extracted with ethyl acetate for three times, the organic phases were combined, washed once with diluted hydrochloric acid and saturated salt solution in turn, dried with anhydrous sodium sulfate, filtered, and concentrated under reduced pressure, purified by column chromatography to obtain 11.4 g of pale yellow solid. $^1$H NMR (400 MHz, $CDCl_3$): δ 7.26-7.23 (m, 2H), 7.18-7.14 (m, 2H), 7.06 (s, 1H), 7.03-7.00 (m, 2H), 5.35 (t, J=9.4 Hz, 1H), 5.23 (t, J=9.6 Hz, 1H), 5.13 (t, J=9.7 Hz, 1H), 4.53 (d, J=9.9 Hz, 1H), 4.40 (d, J=9.8 Hz, 1H), 3.99-3.88 (m, 2H), 2.20 (s, 3H), 2.19 (s, 3H), 2.11 (s, 3H), 2.03 (s, 3H), 1.78 (s, 3H)

(2S,3S,4R,5S,6R)-2-(3-(4-((E)-4-methoxy-4-oxobut-1-en-1-yl)benzyl)-4-methylphenyl)-6-(methylthio)tetrahydro-2H-pyran-3,4,5-triyl triacetate (2S,3S,4R,5S,6R)-2-(3-(4-chlorobenzyl)-4-methylphenyl)-6-(methylthio)tetrahydro-2H-pyran-3,4,5-triyl triacetate (1.0 g), methyl 3-butenoate (1.0 ml), $Pd_2(dba)_3$ (366 mg), tri-tert-butylphosphine tetrafluoroborate (232 mg), dicyclohexylmethylamine (1.2 ml) and N-methylpyrrolidone (10 ml) were added into a 25 ml microwave reaction tube, after nitrogen replacement, the mixture was heated to 160° C. by microwave and reacted for 1 h. This operation process was repeated for 10 times and for a total of 10 g of raw materials. The reaction solutions were combined and diluted with ethyl acetate, added with water, and subjected to liquid separation. The aqueous phase was extracted with ethyl acetate for three times. The organic phases were combined, washed once with diluted hydrochloric acid and saturated salt solution in turn, dried with anhydrous sodium sulfate, filtered, and concentrated under reduced pressure, purified by column chromatography to obtain 6.4 g of pale yellow solid. $^1$H NMR (400 MHz, $CDCl_3$): δ 7.30-7.28 (m, 2H), 7.16-7.15 (m, 2H), 7.04-7.02 (m, 3H), 6.47 (d, J=15.9 Hz, 1H), 6.30-6.22 (m, 1H), 5.35 (t, J=9.4 Hz, 1H), 5.23 (t, J=9.6 Hz, 1H), 5.13 (t, J=9.7 Hz, 1H), 4.53 (d, J=9.8 Hz, 1H), 4.40 (d, J=9.9 Hz, 1H), 4.01-3.90 (m, 2H), 3.73 (s, 3H), 3.26 (dd, J=1.2, 7.1 Hz, 2H), 2.21 (s, 3H), 2.18 (s, 3H), 2.11 (s, 3H), 2.02 (s, 3H), 1.77 (s, 3H).

(2S,3S,4R,5S,6R)-2-(3-(4-(4-Methoxy-4-oxobutyl)benzyl)-4-methylphenyl)-6-(methylthio)tetrahydro-2H-pyran-3,4,5-triyl triacetate (2S,3S,4R,5S,6R)-2-(3-(4-((E)-4-methoxy-4-oxobut-1-en-1-yl)benzyl)-4-methylphenyl)-6-(meth ylthio)tetrahydro-2H-pyran-3,4,5-triyl triacetate (6.8 g), methanol (60 ml), tetrahydrofuran (60 ml), 5% palladium on carbon (1.4 g) were added into a 250 ml reaction flask, hydrogen replacement was carried out for 3 times, and the mixture was stirred at room temperature for 4 h. The reaction solution was filtered with diatomite, and the filtrate was concentrated under reduced pressure, and purified by column chromatography to obtain 5.6 g of pale yellow solid.

4-(4-(2-methyl-5-(2S,3R,4R,5S,6R)-3,4,5-trihydroxy-6-(methylthio)tetrahydro-2H-pyran-2-yl)benzyl)phenyl)butyric acid (2S,3S,4R,5S,6R)-2-(3-(4-(4-Methoxy-4-oxobutyl)benzyl)-4-methylphenyl)-6-(methylthio)tetrahydro-2H-pyran-3,4,5-triyl triacetate (5.6 g), methanol (30 ml), tetrahydrofuran (15 ml) and water (30 ml) were added into a 250 ml reaction flask, then lithium hydroxide monohydrate (4.0 g) was slowly added, and after addition, the mixture was stirred at room temperature for 4 h. The reaction solution was diluted with water, and extracted with ethyl acetate for three times. The organic phase was discarded, and the pH of the aqueous phase was adjusted to 1 with diluted hydrochloric acid, and extracted with ethyl acetate for three times. The organic phases were combined, washed once with saturated salt solution, and dried with anhydrous sodium sulfate, and filtered. The filtrate was concentrated under reduced pressure to obtain 2.8 g of white solid. {0>$^1$H NMR (400 MHz, DMSO-d6): $^1$H NMR (400 MHz, DMSO-d6): δ 12.04 (s, 1H), 7.11-7.04 (m, 7H), 5.22 (d, J=5.5 Hz, 1H), 5.13 (br s, 1H), 4.88 (d, J=5.4 Hz, 1H), 4.33 (d, J=9.4 Hz, 1H), 4.05 (d, J=8.9 Hz, 1H), 3.91 (s, 2H), 3.29-3.15 (m, 3H), 2.53 (t, J=7.4 Hz, 2H), 2.20 (t, J=7.4 Hz, 2H), 2.17 (s, 3H), 2.03 (s, 3H), 1.80-1.72 (quin, J=7.7 Hz, 2H). MS: m/z 445.2, $[M-H]^-$.

Intermediate: 3-((4-(2-methyl-5-((2S,3R,4R,5S,6R)-3,4,5-trihydroxy-6-(methylthio)tetrahydro-2H-pyran-2-yl)benzyl)benzyl)oxy)propionic acid

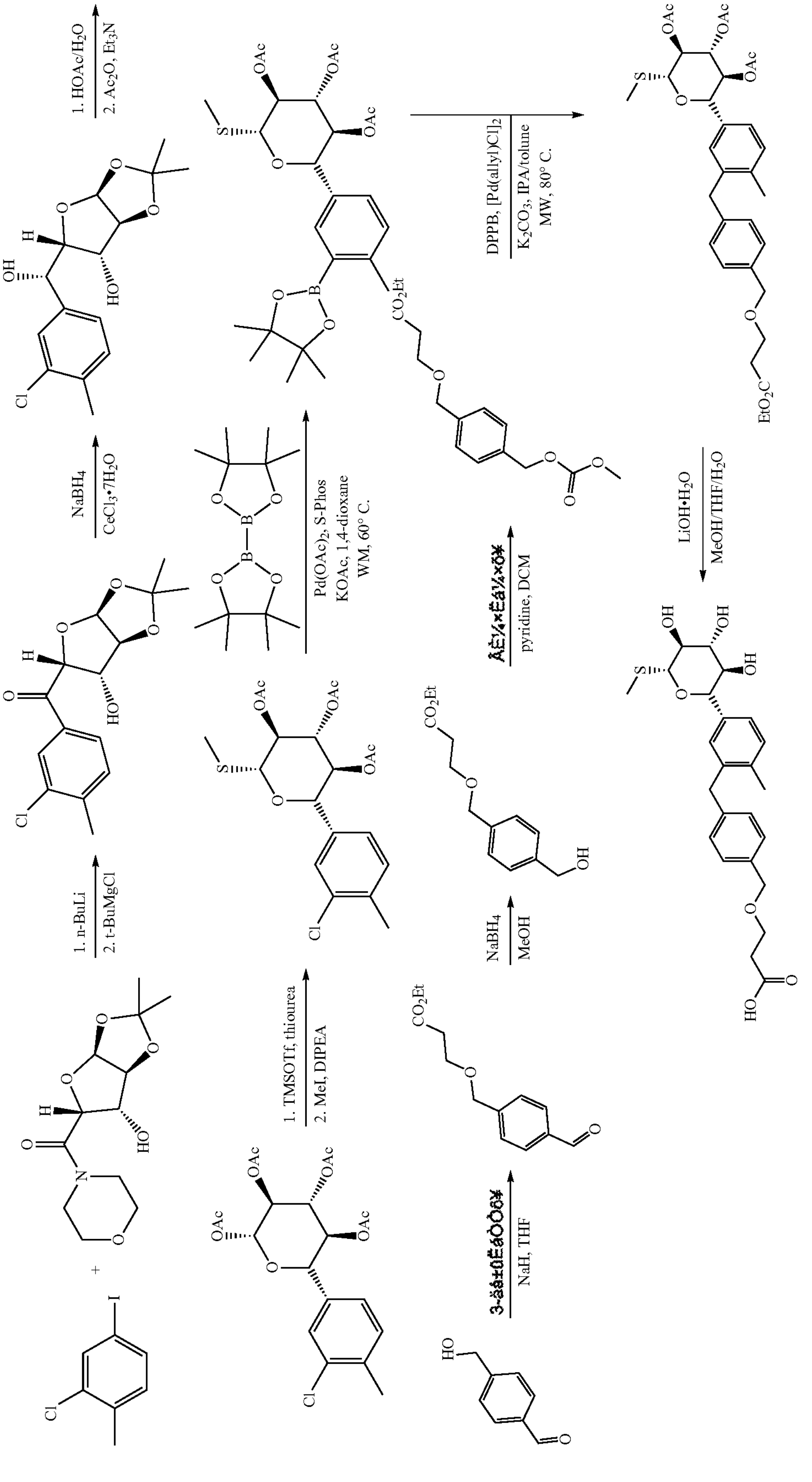
1. n-BuLi
2. t-BuMgCl
NaBH4
CeCl3•7H2O
1. HOAc/H2O
2. Ac2O, Et3N
1. TMSOTf, thiourea
2. MeI, DIPEA
Pd(OAc)2, S-Phos
KOAc, 1,4-dioxane
WM, 60° C.
DPPB, [Pd(allyl)Cl]2
K2CO3, IPA/tolune
MW, 80° C.
NaH, THF
NaBH4
MeOH
pyridine, DCM
LiOH•H2O
MeOH/THF/H2O (3-Chloro-4-methylphenyl)((3aS,5R,6S,6aS)-6-hydroxy-2,2-dimethyltetrahydrofuro[2,3-d][1,3]dioxol-5-yl)methanone (3aS,5R,6S,6aS)-6-Hydroxy-2,2-dimethyltetrahydrofuro[2,3-d][1,3]dioxol-5-yl)(morpholinyl)methanone (5.0 g) and tetrahydrofuran (50 ml) were added into a 250 ml reaction flask, under nitrogen protection, cooled to 0° C. in an ice bath, then added with tert-butylmagnesium chloride (1M in THF, 20.1 mL), and stirred for 30 min.

2-Chloro-4-iodotoluene (5.5 g) and tetrahydrofuran (50 ml) were added into a 500 ml reaction flask, under nitrogen protection, cooled to −78° C., slowly added with n-butyllithium (1.6M in hexane, 14.9 ml), and stirred for 10 min after addition. The newly prepared Grignard reaction solution above was added, and after addition, the mixture was returned to room temperature and stirred for 1 h. The reaction solution was poured into saturated aqueous ammonium chloride solution, and extracted with ethyl acetate for three times. The organic phases were combined, washed with saturated salt solution, dried with anhydrous sodium sulfate, filtered, concentrated under reduced pressure, and purified by column chromatography to obtain 4.0 g of white solid.

(3aS,5S,6R,6aS)-5-((S)-(3-chloro-4-methylphenyl)(hydroxy)methyl)-2,2-dimethyltetrahydrofuro[2,3-d][1,3]dioxol-6-ol (3-Chloro-4-methylphenyl)(3aS,5R,6S,6aS)-6-hydroxy-2,2-dimethyltetrahydrofuro[2,3-d][1,3]dioxol-5-yl)methanone (3.0 g), cerium chloride heptahydrate (4.3 g) and methanol (60 ml) were added into a 250 ml reaction flask, cooled to 0° C. in an ice bath, and then slowly dropwise added with a solution (5 ml) of sodium borohydride (0.4 g) in 1M aqueous sodium hydroxide. After the addition, the mixture was returned to room temperature and stirred for 1 h. The reaction solution was poured into saturated aqueous ammonium chloride solution, and extracted with ethyl acetate for three times. The organic phases were combined, washed once with saturated salt solution, dried with anhydrous sodium sulfate, filtered, and concentrated to obtain 3.0 g of pale yellow solid.

(2R,3S,4R,5S,6S)-6-(3-Chloro-4-methylphenyl)tetrahydro-2H-pyran-2,3,4,5-tetrayl tetraacetate (3aS,5S,6R,6aS)-5-((S)-(3-chloro-4-methylphenyl)(hydroxy)methyl)-2,2-dimethyltetrahydrofuro[2,3-d][1,3]dioxol-6-ol (3.0 g), glacial acetic acid (15 ml) and water (15 ml) were added into a 150 ml reaction flask, heated to 110° C. and stirred for 4 h. The reaction solution was concentrated to dryness, and azeotropically distilled with toluene for three times. The residue was dissolved in 30 ml of acetonitrile, and then added with triethylamine (13.3 ml), and a solution (18 ml) of acetic anhydride (9.0 ml) in acetonitrile was slowly added dropwise at 35° C. under nitrogen protection. After the addition, the mixture was cooled to room temperature naturally and stirred for 15 h. The reaction solutions were c diluted with ethyl acetate, added with water, and subjected to liquid separation. The aqueous phase was extracted with ethyl acetate for three times. The organic phases were combined, washed once with diluted hydrochloric acid and once with saturated salt solution in turn, dried with anhydrous sodium sulfate, filtered, and concentrated to obtain 4.6 g of brown oily substance, which was directly added to next reaction.

(2S,3S,4R,5S,6R)-2-(3-Chloro-4-methylphenyl)-6-(methylthio)tetrahydro-2H-pyran-3,4,5-triyl triacetate (2R,3S,4R,5S,6S)-6-(3-Chloro-4-methylphenyl)tetrahydro-2H-pyran-2,3,4,5-tetrayl tetraacetate (4.6 g (theoretical amount)), thiourea (1.5 g), 1,4-dioxane (40 ml) and trimethylsilyl trifluoromethanesulfonate (3.5 ml) were added into a 150 ml reaction flask, heated to 90° C. and stirred for 2 h. The reaction solution was cooled to room temperature, added with iodomethane (1.8 ml) and N,N-diisopropylethylamine (9.5 ml) successively, and then stirred for 15 h. The reaction solution was added with ethyl acetate and water, and subjected to liquid separation. The aqueous phase was extracted with ethyl acetate for three times, the organic phases were combined, washed once with diluted hydrochloric acid and once with saturated salt solution, dried with anhydrous sodium sulfate, filtered, and concentrated under reduced pressure, purified by column chromatography to obtain 2.4 g of pale yellow solid.

$^1$H NMR ($CDCl_3$, 400 MHz): δ 7.33 (d, J=1.6 Hz, 1H), 7.21 (d, J=7.9 Hz, 1H), 7.17-7.14 (dd, J=1.6, 7.8 Hz, 1H), 5.36 (t, J=9.4 Hz, 1H), 5.23 (t, J=9.7 Hz, 1H), 5.10 (t, J=9.7 Hz, 1H), 4.55 (d, J=9.9 Hz, 1H), 4.41 (d, J=9.9 Hz, 1H), 2.37 (s, 3H), 2.22 (s, 3H), 2.12 (s, 3H), 2.04 (s, 3H), 1.87 (s, 3H). MS: m/z 453.1, $[M+Na]^+$.

(2S,3S,4R,5S,6R)-2-(4-methyl-3-(4,4,5,5-tetramethyl-1,3,2-dioxaborolane-2-yl)phenyl)-6-(methylthio)tetrahydro-2H-pyran-3,4,5-triyl triacetate (2S,3S,4R,5S,6R)-2-(3-Chloro-4-methylphenyl)-6-(methylthio)tetrahydro-2H-pyran-3,4,5-triyl triacetate (1.2 g), bis(pinacolato)diboron (1.4 g), potassium acetate (0.8 g), palladium acetate (0.05 g), 2-dicyclohexylphosphino-2',6'-dimethoxybiphenyl (0.1 g) and 1,4-dioxane (10 ml) were added into a 25 ml microwave tube, after nitrogen replacement, the mixture was heated to 60° C. by microwave and stirred for 18 h. The reaction solution was concentrated, and then purified by column chromatography to obtain 1.1 g of pale yellow solid. $^1$H NMR ($CDCl_3$, 400 MHz): δ 7.67 (d, J=2.0 Hz, 1H), 7.37 (dd, J=2.1, 8.0 Hz, 1H), 7.17 (d, J=7.9 Hz, 1H), 5.36 (t, J=9.4 Hz, 1H), 5.24 (t, J=9.6 Hz, 1H), 5.15 (t, J=9.7 Hz, 1H), 4.54 (d, J=9.9 Hz, 1H), 4.46 (d, J=9.9 Hz, 1H), 2.52 (s, 3H), 2.20 (s, 3H), 2.12 (s, 3H), 2.03 (s, 3H), 1.85 (s, 3H), 1.35 (d, J=3.3 Hz, 12H). MS: m/z 545.2, $[M+Na]^+$.

Ethyl 3-(4-formylbenzyl)oxy)propionate p-Hydroxymethylbenzaldehyde (3.0 g) and tetrahydrofuran (30 ml) were added into a 150 ml reaction flask, cooled to 0° C. in an ice bath, and a solution of ethyl 3-bromopropionate (14.1 ml) in tetrahydrofuran (15 ml) was slowly added dropwise, and the mixture was returned to room temperature and stirred for 15 h after the addition. The reaction solution was poured into saturated aqueous ammonium chloride solution, and extracted with ethyl acetate for three times. The organic phases were combined, washed once with saturated salt solution, dried with anhydrous sodium sulfate, filtered, concentrated under reduced pressure and purified by column chromatography to obtain 800 mg of colorless liquid. $^1$H NMR ($CDCl_3$, 400 MHz): δ 10.03 (s, 1H), 7.89 (d, J=8.2 Hz, 2H), 7.52 (d, J=8.0 Hz, 2H), 4.64

(s, 2H), 4.19 (q, J=7.1 Hz, 2H), 3.82 (t, J=6.3 Hz, 2H), 2.66 (t, J=6.3 Hz, 2H), 1.29 (t, J=7.1 Hz, 3H).

Ethyl 3-(4-(hydroxymethyl)benzyloxy)propionate

Ethyl 3-(4-Formylbenzyl)oxy)propionate (800 mg) and methanol (16 ml) were added into a 50 ml reaction flask, cooled to 0° C. in an ice bath, and added with sodium borohydride (193 mg) in batches. After addition, the mixture was returned to room temperature and stirred for 2 h. The reaction solution was poured into 1N HCl aqueous solution, and extracted with ethyl acetate for three times. The organic phases were combined, washed once with saturated salt solution, dried with anhydrous sodium sulfate, filtered, concentrated under reduced pressure and purified by column chromatography to obtain 600 mg of colorless liquid. $^1$H NMR ($CDCl_3$, 400 MHz): δ 7.36-7.32 (m, 4H), 4.68 (s, 2H), 4.54 (s, 2H), 4.17 (q, J=7.2 Hz, 2H), 3.75 (t, J=6.4 Hz, 2H), 2.62 (t, J=6.4 Hz, 2H), 2.07 (br s, 1H), 1.27 (t, J=7.1 Hz, 3H).

Ethyl 3-((4-(((methoxycarbonyl)oxy)methyl)benzyl)oxy)propionate

Ethyl 3-(4-(hydroxymethyl)benzyloxy)propionate (600 mg), pyridine (0.4 ml) and dichloromethane (6 ml) were added into a 50 ml reaction flask, cooled to 0° C. in an ice bath, and dropwise added with a solution (2 ml) of methyl chloroformate (0.5 ml) in dichloromethane. After addition, the mixture was returned to room temperature and stirred for 3 h. The reaction solution was poured into 1N HCl aqueous solution, and extracted with ethyl acetate for three times. The organic phases were combined, washed once with saturated salt solution, dried with anhydrous sodium sulfate, filtered, concentrated and purified by column chromatography to obtain 620 mg of colorless liquid. $^1$H NMR ($CDCl_3$, 400 MHz): δ 7.41-7.34 (m, 4H), 5.17 (s, 2H), 4.55 (s, 2H), 4.18 (q, J=7.1 Hz, 2H), 3.81 (s, 3H), 3.76 (t, J=6.4 Hz, 2H), 2.63 (t, J=6.4 Hz, 2H), 1.28 (t, J=7.1 Hz, 3H).

(2S,3S,4R,5S,6R)-2-(3-(4-(3-ethoxy-3-oxopropyloxy)methyl)benzyl)-4-methylphenyl)-6-(methylthio)tetrahydro-2H-pyran-3,4,5-triyl triacetate 1,4-Bis(diphenylphosphino)butane (72 mg), allylpalladium(II) chloride dimer (32 mg), toluene (4 ml) and isopropanol (2 ml) were added into a 25 ml there-necked flask. After nitrogen replacement, the mixture was stirred at room temperature for 30 min.

(2S,3S,4R,5S,6R)-2-(4-Methyl-3-(4,4,5,5-tetramethyl-1,3,2-dioxaborolan-2-yl)phenyl)-6-(methyl thio)tetrahydro-2H-pyran-3,4,5-triyl triacetate (911 mg) and Ethyl 3-((4-(((methoxycarbonyl)oxy)methyl)benzyl)oxy)propionate and isopropanol (8 ml) were added into a 25 ml microwave reaction tube, the above catalyst was added after nitrogen replacement, and the reaction was microwaved to 80° C. for 12 h. The reaction solution was concentrated under reduced pressure, and then purified by column chromatography to obtain 540 of oily substance. $^1$H NMR ($CDCl_3$, 400 MHz): $^1$H NMR ($CDCl_3$, 400 MHz): δ 7.23 (d, J=8.1 Hz, 2H), 7.18-7.13 (m, 2H), 7.07-7.05 (m, 3H), 5.34 (t, J=9.4 Hz, 1H), 5.22 (t, J=9.6 Hz, 1H), 5.13 (t, J=9.7 Hz, 1H), 4.53 (d, J=9.9 Hz, 1H), 4.50 (s, 2H), 4.40 (d, J=9.8 Hz, 1H), 4.15 (q, J=7.2 Hz, 2H), 4.00-3.92 (m, 2H), 3.75 (t, J=6.4 Hz, 2H), 2.61 (t, J=6.4 Hz, 2H), 2.21 (s, 3H), 2.18 (s, 3H), 2.11 (s, 3H), 2.02 (s, 3H), 1.76 (s, 3H), 1.27 (t, J=6.4 Hz, 3H).

3-((4-(2-methyl-5-((2S,3R,4R,5S,6R)-3,4,5-trihydroxy-6-(methylthio)tetrahydro-2H-pyran-2-yl)benzyl)benzyl)oxy)propionic acid (2S,3S,4R,5S,6R)-2-(3-(4-(3-ethoxy-3-oxopropyloxy)methyl)benzyl)-4-methylphenyl)-6-(methyl thio)tetrahydro-2H-pyran-3,4,5-triyl triacetate (540 mg), methanol (3 ml), tetrahydrofuran (1.5 ml), water (3 ml) and lithium hydroxide monohydrate (368 mg) were added into a 25 ml reaction flask, and stirred at room temperature for 15 h. The reaction solution was diluted with water, and extracted with ethyl acetate for three times. The organic phase was discarded, and the pH of the aqueous phase was adjusted to 1 with diluted hydrochloric acid, and extracted with ethyl acetate for three times. The organic phases were combined, washed once with saturated salt solution, and dried with anhydrous sodium sulfate, and filtered. The filtrate was concentrated under reduced pressure to obtain 300 mg of colorless foam. $^1$H NMR (DMSO-d6, 400 MHz): $^1$H NMR (DMSO-d6, 400 MHz): δ 12.19 (br s, 1H), 7.22 (d, J=8.1 Hz, 2H), 7.13-7.11 (m, 5H), 5.22 (br s, 1H), 4.89 (br s, 1H), 4.42 (s, 2H), 4.33 (d, J=9.4 Hz, 1H), 4.05 (d, J=9.1 Hz, 1H), 3.94 (s, 2H), 3.61 (t, J=6.3 Hz, 2H), 3.51-3.45 (m, 1H), 3.30-3.17 (m, 3H), 2.48 (t, J=6.3 Hz, 2H), 2.18 (s, 3H), 2.04 (s, 3H). $^{13}$C NMR (DMSO-d6, 100 MHz): δ 173.2, 140.0, 138.7, 137.9, 136.3, 135.8, 130.1, 129.7, 128.9, 128.1, 126.0, 85.8, 81.8, 78.6, 74.8, 72.7, 72.2, 66.0, 38.9, 35.2, 19.5, 11.5. MS: m/z 485.2, $[M+Na]^+$.

Intermediate: $N^1$-methyl-$N^1$-(prop-2-yn-1-yl)eth-1,2-diamine

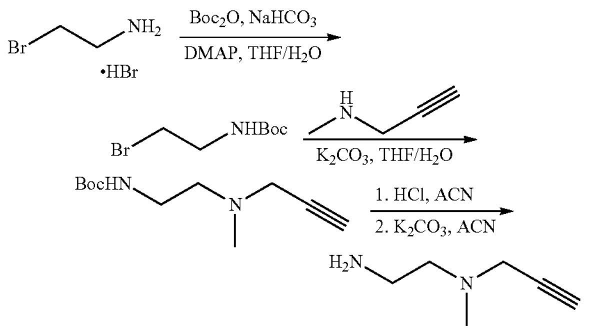

2-(Boc-amino)ethyl bromide

Tetrahydrofuran (4 ml), water (4 ml) and bromoethylamine hydrobromic acid (2.05 g) were successively added into a 25 ml reaction flask, cooled to 10° C., then added with sodium bicarbonate (2.1 g), 4-dimethylaminopyridine (61 mg), and di-tert-butyl dicarbonate (2.05 g), and stirred at 10° C. for 8 h after addition. The reaction solution was filtered, the filtrate was subjected to liquid separation, the aqueous phase was extracted twice with dichloromethane, and the organic phases were combined, washed once with saturated salt solution, dried with anhydrous sodium sulfate, and concentrated under reduced pressure to obtain 2.0 g of pale yellow liquid.

$N^1$-methyl-$N^1$-(prop-2-yn-1-yl)eth-1,2-diamine

N-methylpropargylamine (0.68 g), tetrahydrofuran (20 ml), water (20 ml), potassium carbonate (2.46 g, 17.8 mmol)

and a solution (5 ml) of 2-(Boc-amino)ethyl bromide (2.0 g) in tetrahydrofuran were successively added into a 100 ml reaction flask, and stirred at room temperature for 2 h after addition. The reaction solution was extracted with ethyl acetate for three times, washed with saturated salt solution, dried with anhydrous sodium sulfate, filtered and concentrated to obtain 1.72 g of pale yellow oily substance. The obtained crude product was dissolved in acetonitrile (10 ml), slowly dropwise added with concentrated hydrochloric acid (5 ml), and stirred at room temperature for 1 h. The reaction solution was concentrated under reduced pressure, dissolved in 10 ml of acetonitrile, added with potassium carbonate (3.35 g, 24.3 mmol), and stirred at 35° C. for 3 h, cooled to room temperature, filtered with diatomite, and washed with acetonitrile. The filtrate was concentrated to dryness to obtain 0.67 g of pale yellow liquid. MS: m/z 112.9, $[M+H]^+$.

Intermediate: 2-amino-2-methyl-N-(2-(methyl(prop-2-yn-1-yl)amino)ethyl)propionamide

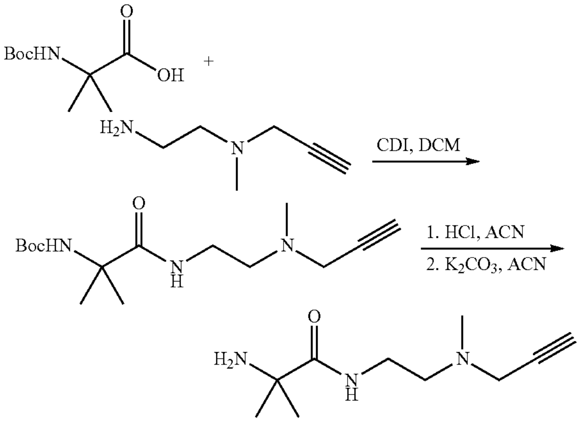

2-((tert-butoxycarbonyl)amino)-2-methylpropionic acid (894 mg) and dichloromethane (25 ml) were added into a 50 ml reaction flask successively, cooled to 0° C. in an ice bath, and slowly added with CDI (713 mg). After addition, the mixture was stirred at 0° C. for 30 min. $N^1$-methyl-$N^1$-(prop-2-yn-1-yl)eth-1,2-diamine (450 mg) was added, and after addition, the mixture was returned to room temperature and stirred for 3 h. The reaction solution was diluted with dichloromethane, added with water, and subjected to liquid separation. The aqueous phase was extracted with dichloromethane for three times, the organic phases were combined, washed once with saturated salt solution, dried with anhydrous sodium sulfate, and concentrated under reduced pressure to obtain 1.04 g of pale yellow liquid. The product was dissolved in acetonitrile (5 ml), slowly dropwise added with concentrated hydrochloric acid (2 ml), and stirred at room temperature for 1 h. The reaction solution was concentrated to dryness, dissolved in acetonitrile (10 ml), added with potassium carbonate (1.93 g), and stirred at 35° C. for 3 h, cooled to room temperature, filtered with diatomite, and washed with acetonitrile. The filtrate was concentrated under reduced pressure to obtain 550 mg of pale yellow liquid. MS: m/z 198.2, $[M+H]^+$.

Intermediate: 2-amino-N-(2-(dimethylamino)ethyl)-2-methylpropionamide

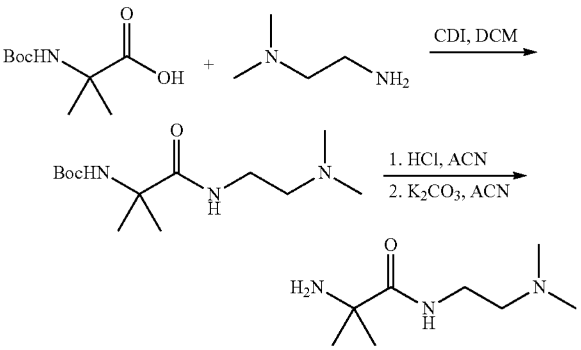

2-((tert-butoxycarbonyl)amino)-2-methylpropionic acid (2.03 g) and dichloromethane (25 ml) were added into a 50 ml reaction flask successively, cooled to 0° C. in an ice bath, and slowly added with CDI (1.62 g). After the addition, the mixture was stirred at 0° C. for 30 min. N,N-dimethylethylenediamine (970 mg) was added, and after addition, the mixture was returned to room temperature and stirred for 3 h. The reaction solution was diluted with dichloromethane, added with water, and subjected to liquid separation. The aqueous phase was extracted with dichloromethane for three times, the organic phases were combined, washed once with saturated salt solution, dried with anhydrous sodium sulfate, and concentrated under reduced pressure to obtain 1.96 g of pale yellow liquid. The product was dissolved in acetonitrile (10 ml), slowly dropwise added with concentrated hydrochloric acid (4 ml), and stirred at room temperature for 1 h. The reaction solution was concentrated to dryness, dissolved in acetonitrile (10 ml), added with potassium carbonate (4.14 g, 30 mmol), and stirred at 35° C. for 3 h, cooled to room temperature, filtered with diatomite, and washed with acetonitrile. The filtrate was concentrated under reduced pressure to obtain 930 mg of pale yellow liquid. MS: m/z 174.2, $[M+H]^+$.

Intermediate: 2-amino-2-methyl-N-(2-(methyl(2-(methyl(prop-2-yn-1-yl)amino)-2-oxoethyl)amino)ethyl)propionamide

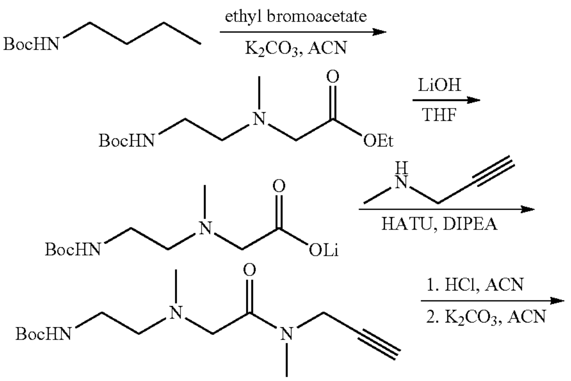

-continued

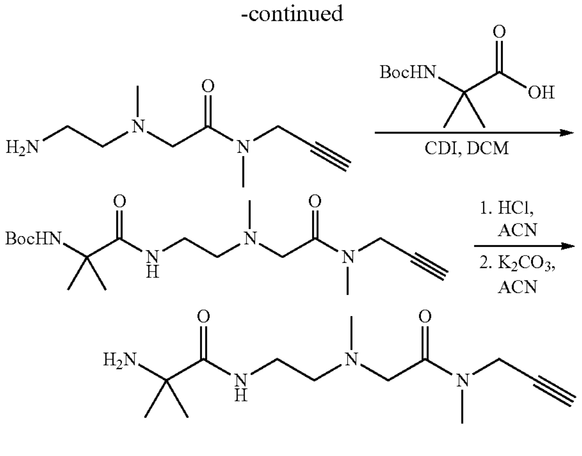

Ethyl N-(2-((tert-butoxycarbonyl)amino)ethyl)-N-methylglycine

Tert-butyl 2-(methylamino)ethylcarbamate (8.7 g), acetonitrile (100 ml), potassium carbonate (10.4 g) and ethyl bromoacetate (9.2 g) were successively added into a 100 ml reaction flask, heated to 35° C. and stirred for 10 h. The reaction solution was filtered, and the filtrate was concentrated under reduced pressure, and purified by column chromatography to obtain 9.89 g of pale yellow oily substance.

2-((2-Aminoethyl)(methyl)amino)-N-methyl-N-(prop-2-yn-1-yl)acetamide

Ethyl N-(2-((tert-butoxycarbonyl)amino)ethyl)-N-methylglycine (5.5 g), tetrahydrofuran (25 ml), lithium hydroxide monohydrate (0.98 g) and water (2 ml) were successively added into a 50 ml reaction flask, and stirred at room temperature for 5 h. The reaction solution was concentrated under reduced pressure, and the concentrated residue was dissolved in dichloromethane (25 ml). HATU (9.62 g), DIPEA (5.57 g) and N-methylpropargylamine (1.75 g) were added successively, and the mixture was stirred at room temperature for 3 h. The reaction solution was diluted with dichloromethane, added with water, and subjected to liquid separation. The organic phase was washed once with saturated salt solution, dried with anhydrous sodium sulfate, concentrated under reduced pressure, and purified by column chromatography to obtain 3.2 g of pale yellow oily substance. The product was dissolved in acetonitrile (15 ml), slowly dropwise added with concentrated hydrochloric acid (5 ml), and stirred at room temperature for 1 h. The reaction solution was concentrated, added with acetonitrile (15 ml) to dissolve, then added with potassium carbonate (6.24 g), and stirred at 35° C. for 3 h. The reaction solution was cooled to room temperature, filtered with diatomite, washed with acetonitrile, and the filtrate was concentrated to obtain 1.67 g of pale yellow liquid.

2-Amino-2-methyl-N-(2-(methyl(2-(methyl(prop-2-yn-1-yl)amino)-2-oxoethyl)amino)ethyl)propionamide 2-((tert-butoxycarbonyl)amino)-2-methylpropionic acid (2.03 g) and dichloromethane (25 ml) were added into a 50 ml reaction flask successively, cooled to 0° C. in an ice bath, and slowly added with CDI (1.62 g). After the addition, the mixture was stirred at 0° C. for 30 min. The reaction solution was added with 2-((2-Aminoethyl)(methyl)amino)-N-methyl-N-(prop-2-yn-1-yl)acetamide (1.67 g), and returned to room temperature and stirred for 3 h after the addition. Dichloromethane was added into the reaction flask to dilute, and then the reaction solution was added with water, and subjected to liquid separation. The aqueous phase was extracted with dichloromethane for three times, and the organic phases were combined, washed once with saturated salt solution, dried with anhydrous sodium sulfate, and concentrated under reduced pressure to obtain 2.1 g of pale yellow oily substance. The product was dissolved in acetonitrile (10 ml), slowly dropwise added with concentrated hydrochloric acid (4 ml), and stirred at room temperature for 1 h. The reaction solution was concentrated to dryness, added with acetonitrile (10 ml) to dissolve, then added with potassium carbonate (3.15 g), and stirred at 35° C. for 3 h. The reaction solution was cooled to room temperature, filtered with diatomite, washed with acetonitrile, and the filtrate was concentrated under reduced pressure to dryness to obtain 1.24 g of pale yellow oily substance. MS: m/z 269.2, $[M+H]^+$.

Intermediate: 2-(4-(2-amino-2-methylpropionyl)piperazin-1-yl)-N-methyl-N-(prop-2-yn-1-yl)acetamide

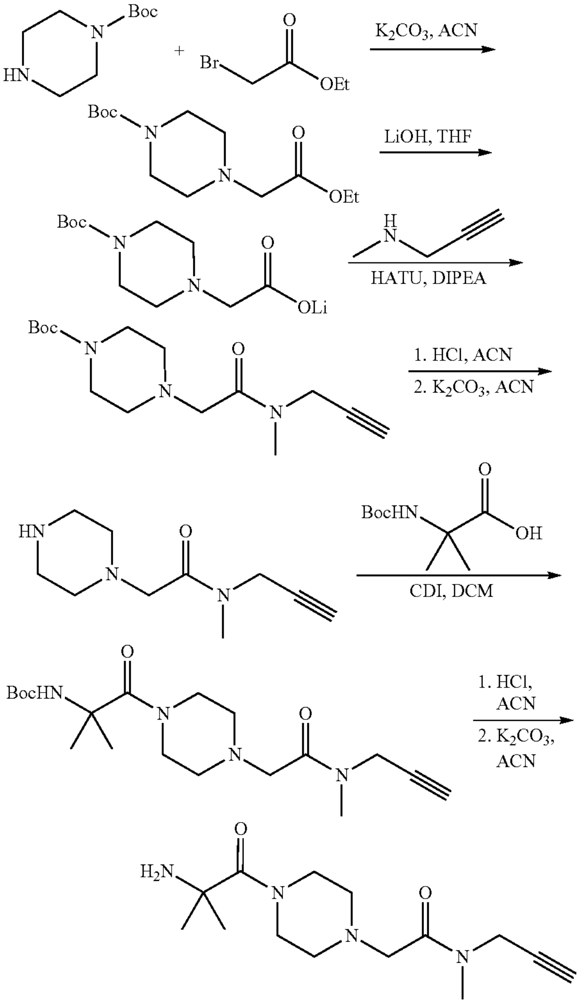

2-(4-(tert-butoxycarbonyl)piperazin-1-yl)lithium acetate

Tert-Butyl 1-piperazinecarboxylate (5 g), ethyl bromoacetate (4.48 g), potassium carbonate (7.32 g) and acetonitrile (50 ml) were successively added into a 100 ml flask, and then stirred at room temperature for 2 h after the addition. The reaction solution was filtered, the filter cake was washed with acetonitrile, the filtrates were combined and concentrated to dryness, and purified by column chromatography to obtain 6.0 g of yellow liquid. The above product, lithium hydroxide monohydrate (1.01 g), water (3 ml) and tetrahydrofuran (20 ml) were successively added into a 100 ml reaction flask, and stirred at room temperature overnight after addition. The reaction solution was concentrated to dryness under reduced pressure to obtain 6.0 g of white solid.

N-methyl-2-(piperazin-1-yl)-N-(prop-2-yn-1-yl)acetamide 2-(4-(tert-butoxycarbonyl)piperazin-1-yl)lithium acetate (6.0 g), methylene chloride (50 ml), HATU (9.8 g) and DIPEA (4.5 g) were successively added into a 100 ml flask, and then stirred in an ice bath for 30 min after the addition. N-methylpropargylamine (1.75 g) was added into the reaction flask and stirred at room temperature for 3 h. The reaction solution was diluted with dichloromethane, and added with water for liquid separation. The organic phases were washed once with saturated salt solution, dried with anhydrous sodium sulfate, filtered, concentrated under reduced pressure, and purified by column chromatography to obtain 4.5 g of yellow liquid. The product was dissolved in acetonitrile (20 ml), slowly dropwise added with concentrated hydrochloric acid (8 ml), and stirred at room temperature for 1 h. The reaction solution was concentrated to dryness, dissolved in acetonitrile (15 ml), added with potassium carbonate (6.3 g), and stirred at 35° C. for 3 h. The reaction solution was cooled to room temperature, filtered with diatomite, and washed with acetonitrile. The filtrate was concentrated to dryness to obtain 2.5 g of pale yellow liquid.

2-(4-(2-amino-2-methylpropionyl)piperazin-1-yl)-N-methyl-N-(prop-2-yn-1-yl)acetamide 2-((tert-butoxycarbonyl)amino)-2-methylpropionic acid (2.6 g) and dichloromethane (25 ml) were added into a 50 ml round flask successively, cooled to 0° C. in an ice bath, and slowly added with CDI (2.07 g). After addition, the mixture was stirred at 0° C. for 30 min. The reaction solution was added with N-methyl-2-(piperazin-1-yl)-N-(prop-2-yn-1-yl)acetamide (2.5 g), and returned to room temperature and stirred for 3 h after addition. The reaction solution was diluted with dichloromethane, and added with water for liquid separation. The aqueous phase was extracted with dichloromethane for three times, and the organic phases were combined, washed once with saturated salt solution, dried with anhydrous sodium sulfate, concentrated to dryness under reduced pressure, and purified by column chromatography to obtain 3.0 g of pale yellow oily substance. The product was dissolved in acetonitrile (15 ml), slowly dropwise added with concentrated hydrochloric acid (8 ml), and stirred at room temperature for 1 h. The reaction solution was concentrated to dryness, dissolved in acetonitrile (10 ml), added with potassium carbonate (3.27 g), and stirred at 35° C. for 3 h. The reaction solution was cooled to room temperature, filtered with diatomite, and washed with acetonitrile. The filtrate was concentrated to dryness under reduced pressure to obtain 1.5 g of pale yellow solid. MS: m/z 281.2, $[M+H]^+$.

Intermediate: 2-amino-2-methyl-N-(2-(methyl(2-oxo-2-(pyrrolidine-1-yl)ethyl)amino)ethyl)propionamide

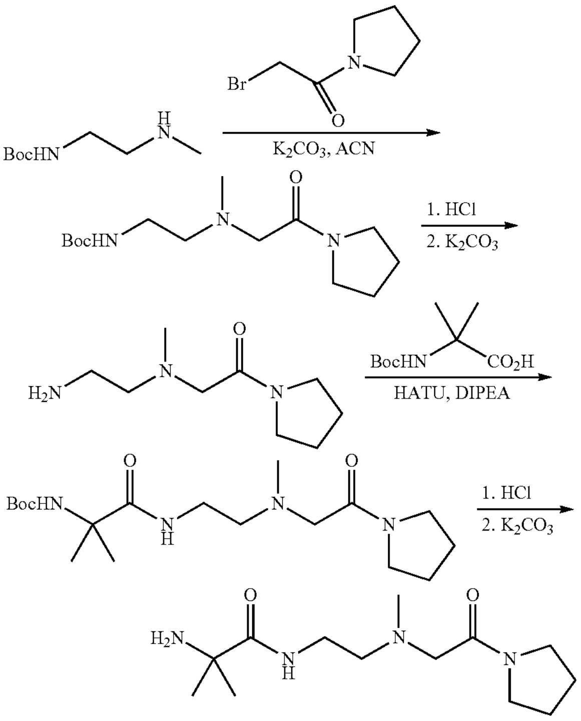

Step 1

Tert-Butyl (2-(methylamino)ethyl)carbamate (5 g), acetonitrile (50 ml), 2-bromo-1(pyrrolidine-1-yl)ethyl-1-one (5.6 g) and potassium carbonate (7.9 g) were successively added into a 100 ml reaction flask, stirred at room temperature for 3 h after the addition, and monitored by TLC. The reaction liquid was filtered with silica gel, eluted with ethyl acetate and concentrated to obtain 5.4 g of colorless oily liquid.

Step 2

The product of the previous step (5.4 g), acetonitrile (20 ml), concentrated hydrochloric acid (10 ml) and methanol (2 ml) were added into a 100 ml reaction flask, stirred at room temperature, and TLC monitored that the raw materials were completely transformed. The reaction solution was concentrated to dryness, added with acetonitrile (20 ml) for dissolution, then added with potassium carbonate (7.9 g), and stirred at 35° C. for 2 h. The reaction solution was cooled to room temperature, filtered with diatomite, and washed with acetonitrile. The filtrate was concentrated to dryness to obtain 2.8 g of colorless oily liquid, which was directly used in next step.

Step 3

2-((tert-butoxycarbonyl)amino)-2-methylpropionic acid (3.08 g), DIPEA (5.9 g), methylene chloride (40 ml) and HATU (6.34 g) were successively added into a 100 ml reaction flask, stirred at room temperature for 20 min, added with the product of the previous step (2.8 g), reacted at room temperature for 3 h after addition, and then monitored by TLC. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 4.3 g of colorless oily liquid. MS: m/z 371.3, $[M+H]^+$.

Step 4

The product of the previous step (1 g), acetonitrile (10 ml), concentrated hydrochloric acid (5 ml) and methanol (1 ml) were added into a 100 ml reaction flask, stirred at room temperature, and monitored by TLC. The reaction solution was concentrated to dryness, added with acetonitrile (10 ml) for dissolution, then added with potassium carbonate (3.9 g), and stirred at 35° C. for 2 h. The reaction solution was cooled to room temperature, filtered with diatomite, and washed with acetonitrile. The filtrate was concentrated to dryness to obtain 580 mg of colorless oily liquid.

Intermediate: 2-amino-N-(2-(2-(dimethylamino)-2-oxoethyl)(methyl)amino)ethyl)-2-methylpropionamide

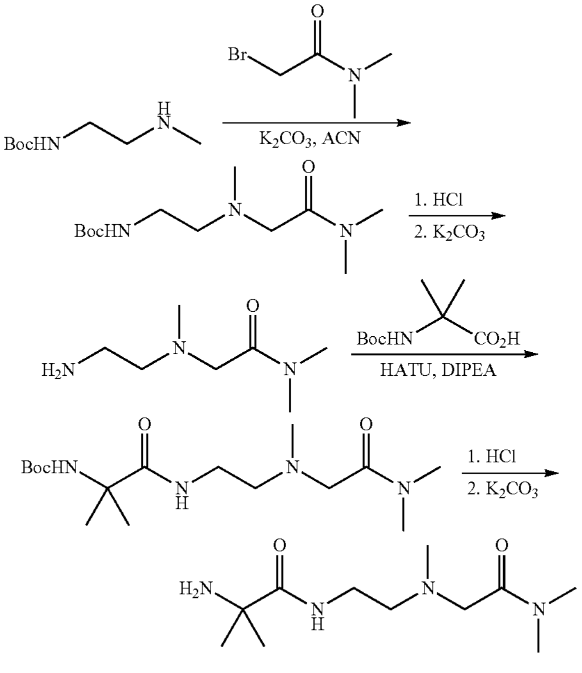

Step 1

Tert-Butyl (2-(methylamino)ethyl)carbamate (5 g), acetonitrile (50 ml), 2-bromo-N,N-dimethylacetamide (4.86 g) and potassium carbonate (7.9 g) were successively added into a 100 ml reaction flask, and stirred at room temperature for 3 h. The reaction liquid was filtered with silica gel, eluted with ethyl acetate and concentrated to obtain 5.84 g of colorless oily liquid. MS: m/z 260.2, $[M+H]^+$.

Step 2

The product of the previous step (5 g), acetonitrile (20 ml), concentrated hydrochloric acid (10 ml) and methanol (2 ml) were added into a 100 ml reaction flask, stirred at room temperature, and monitored by TLC. The reaction solution was concentrated to dryness, added with acetonitrile (20 ml) for dissolution, then added with potassium carbonate (28 g), and stirred at 35° C. for 2 h. The reaction solution was cooled to room temperature, filtered with diatomite, and washed with acetonitrile. The filtrate was concentrated to dryness to obtain 3 g of colorless oily liquid, which was directly used in next step.

Step 3

2-((tert-butoxycarbonyl)amino)-2-methylpropionic acid (3.08 g), DIPEA (5.9 g), methylene chloride (40 ml) and HATU (6.34 g) were successively added into a 100 ml reaction flask, stirred at room temperature for 20 min, added with the product of the previous step (2.4 g), reacted at room temperature for 3 h after addition, and then monitored by TLC. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by silica gel column chromatography to obtain 3 g of colorless oily liquid.

Step 4

The product of the previous step (1 g), acetonitrile (10 ml), concentrated hydrochloric acid (5 ml) and methanol (1 ml) were added into a 100 ml reaction flask, stirred at room temperature, and monitored by TLC. The reaction solution was concentrated to dryness, added with acetonitrile (10 ml) for dissolution, then added with potassium carbonate (3.9 g), and stirred at 35° C. for 2 h. The reaction solution was cooled to room temperature, filtered with diatomite, and washed with acetonitrile. The filtrate was concentrated to dryness to obtain 689 of mg colorless oily liquid.

Intermediate: 2-amino-2-methyl-N-(2-(methyl(2-(4-methylpiperazine-1-yl)-2-oxoethyl)amino)ethyl) propionamide

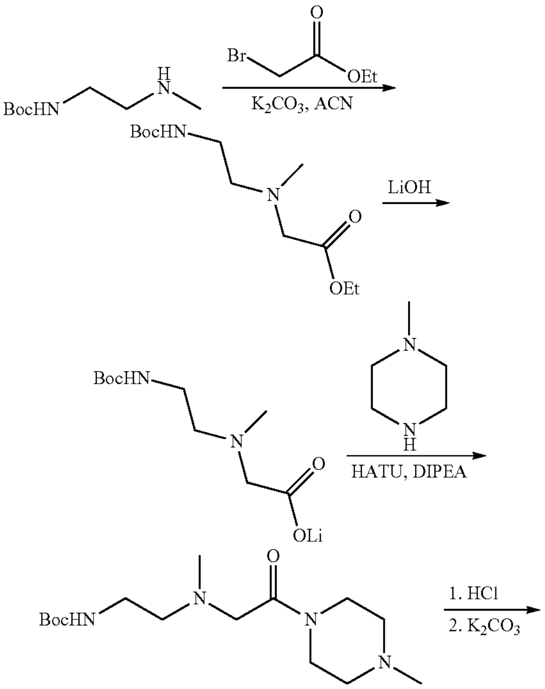

-continued

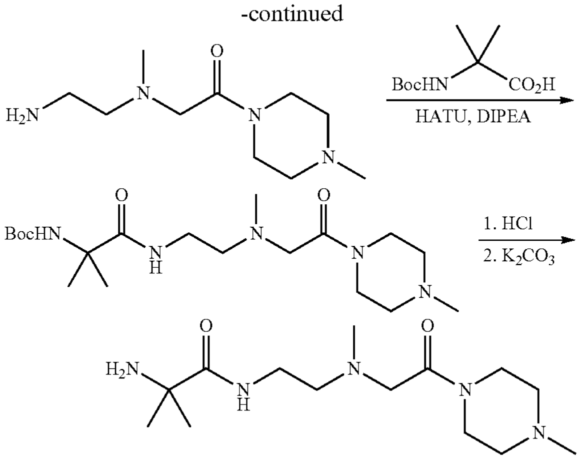

Step 1

Tert-Butyl (2-(methylamino)ethyl)carbamate (5 g), acetonitrile (50 ml), ethyl bromoacetate (4.86 g) and potassium carbonate (7.9 g) were successively added into a 100 ml reaction flask, and stirred at room temperature for 3 h. The reaction liquid was filtered with silica gel, eluted with ethyl acetate and concentrated to obtain 6.1 g of colorless oily liquid. MS: m/z 261.2, $[M+H]^+$.

Step 2

The product of the previous step (6.1 g), tetrahydrofuran (20 ml), water (2 ml) and lithium hydroxide monohydrate (1.1 g) were added into a 100 ml reaction flask, and reacted at 60° C. for 2 h. The reaction solution was concentrated to dryness, added with toluene (20 ml) for azeotropic concentration to dryness to obtain 5.2 g of off-white solid, which was directly used in the next step.

Step 3

The product of the previous step (3.6 g), methylpiperazine (1.52 g), DIPEA (5.9 g), methylene chloride (40 ml) and HATU (6.34 g) were successively added into a 100 ml reaction flask, and reacted at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 3 g of waxy solid. MS: m/z 315.2, $[M+H]^+$.

Step 4

The product of the previous step (3 g), acetonitrile (20 ml), concentrated hydrochloric acid (10 ml) and methanol (2 ml) were added into a 100 ml reaction flask, stirred at room temperature, and monitored by TLC. The reaction solution was concentrated to dryness, dissolved in acetonitrile (20 ml), added with potassium carbonate (6.9 g), and stirred at 35° C. for 2 h. The reaction solution was cooled to room temperature, filtered with diatomite, and washed with acetonitrile. The filtrate was concentrated to dryness to obtain 2.1 g of colorless oily liquid.

Step 5

2-((tert-butoxycarbonyl)amino)-2-methylpropionic acid (1.9 g), DIPEA (3.6 g, 28.1 mmol), methylene chloride (40 ml) and HATU (3.9 g) were successively added into a 100 ml reaction flask, stirred at room temperature, added with the product of the previous step (2.0 g), and reacted at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 2.2 g of colorless oily liquid.

Step 6

The product of the previous step (1 g), acetonitrile (10 ml), concentrated hydrochloric acid (5 ml) and methanol (1 ml) were added into a 100 ml reaction flask, stirred at room temperature, and monitored by TLC. The reaction solution was concentrated to dryness, dissolved in acetonitrile (10 ml), added with potassium carbonate (3.9 g), and stirred at 35° C. for 2 h. The reaction solution was cooled to room temperature, filtered with diatomite, and washed with acetonitrile. The filtrate was concentrated to dryness to obtain 718 mg of colorless oily liquid.

Intermediate: 2-amino-2-methyl-1-(4-(2-oxo-2-(pyrrolidine-1-yl)ethyl)piperazin-1-yl)propane-1-one

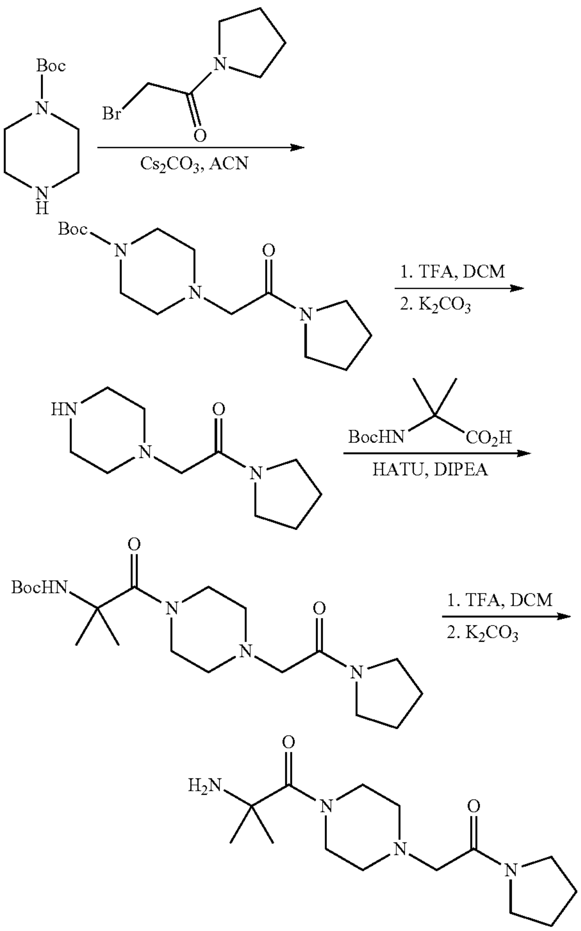

Step 1

Tert-butyl piperazine-1-carboxylate (4.08 g), acetonitrile (50 ml), 2-bromo-1(pyrrolidine-1-yl)ethyl-1-one ((4.4 g) and caesium carbonate (10.7 g) were successively added into a 100 ml reaction flask, and reacted at room temperature for 3 h. The reaction liquid was filtered with silica gel, eluted with ethyl acetate and concentrated to obtain 5.6 g of colorless oily liquid. MS: m/z 298.2, $[M+H]^+$.

Step 2

The product of the previous step (5 g), acetonitrile (20 ml), concentrated hydrochloric acid (10 ml) and methanol (2 ml) were added into a 100 ml reaction flask, stirred at room temperature, and monitored by TLC. The reaction solution was concentrated to dryness, dissolved in acetonitrile (20 ml), added with potassium carbonate (9.3 g), and stirred at 35° C. for 2 h. The reaction solution was cooled to room temperature, filtered with diatomite, and washed with acetonitrile. The filtrate was concentrated to dryness to obtain 3.3 g of colorless oily liquid.

Step 3

2-((tert-butoxycarbonyl)amino)-2-methylpropionic acid (3.08 g), DIPEA (5.9 g), methylene chloride (40 ml) and HATU (6.34 g) were successively added into a 100 ml reaction flask, stirred at room temperature for 20 min, added with the product of the previous step (3 g), and reacted at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 3.6 g of colorless waxy solid.

Step 4

The product of the previous step (2 g), acetonitrile (10 ml), concentrated hydrochloric acid (5 ml) and methanol (1 ml) were added into a 100 ml reaction flask, stirred at room temperature, and monitored by TLC. The reaction solution was concentrated to dryness, dissolved in acetonitrile for resolution, added with potassium carbonate (3.6 g), and stirred at 35° C. for 2 h. The reaction solution was cooled to room temperature, filtered with diatomite, and washed with acetonitrile. The filtrate was concentrated to dryness to obtain 1.3 g of colorless oily liquid.

Intermediate: 2-(4-(2-amino-2-methylpropionyl)piperazin-1-yl)-N,N-dimethylacetamide

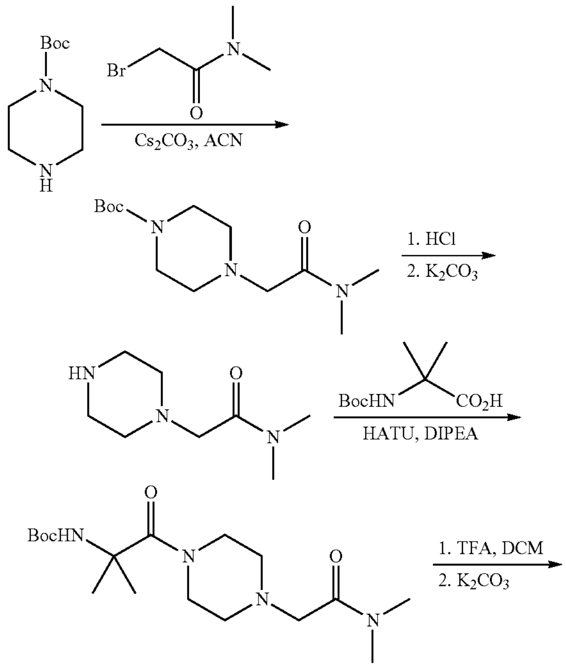

-continued

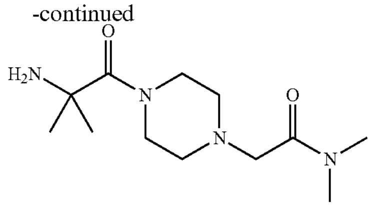

Step 1

Tert-butyl piperazine-1-carboxylate (5 g), acetonitrile (50 ml), 2-bromo-N,N-dimethylacetamide (4.9 g) and potassium carbonate (7.42 g, 53.7 mmol) were successively added into a 100 ml reaction flask, and stirred at room temperature for 3 h. The reaction liquid was filtered with silica gel, eluted with ethyl acetate and spin-dried to obtain 7.3 g of white solid. MS: m/z 272.2, $[M+H]^+$.

Step 2

The product of the previous step (5 g), acetonitrile (20 ml), concentrated hydrochloric acid (10 ml) and methanol (2 ml) were added into a 100 ml reaction flask, stirred at room temperature, and TLC monitored that the reaction was completed. The reaction solution was concentrated to dryness, dissolved in acetonitrile (20 ml), added with potassium carbonate (10.2 g), and stirred at 35° C. for 2 h. The reaction solution was cooled to room temperature, filtered with diatomite, and washed with acetonitrile. The filtrate was concentrated to dryness to obtain 3 g of colorless oily liquid.

Step 3

2-((tert-butoxycarbonyl)amino)-2-methylpropionic acid (3.1 g), DIPEA (5.9 g), methylene chloride (40 ml) and HATU (6.3 g) were successively added into a 100 ml reaction flask, stirred at room temperature for 20 min, added with the product of the previous step (2.6 g), and reacted at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 3.51 g of colorless waxy solid. MS: m/z 357.3, $[M+H]^+$.

Step 4

The product of the previous step (2 g), acetonitrile (10 ml), concentrated hydrochloric acid (8 ml) and methanol (1 ml) were added into a 100 ml reaction flask, stirred at room temperature, and TLC monitored that the reaction was completed. The reaction solution was concentrated to dryness, dissolved in acetonitrile (10 ml), added with potassium carbonate (3.1 g), and stirred at 35° C. for 2 h. The reaction solution was cooled to room temperature, filtered with diatomite, and washed with acetonitrile. The filtrate was concentrated to dryness to obtain 1.22 g of white waxy solid.

Intermediate: 2-amino-2-methyl-1-(4-(2-(4-methylpiperazine-1-yl)-2-oxoethyl)piperazin-1-yl)propane-1-one

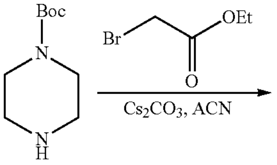

-continued

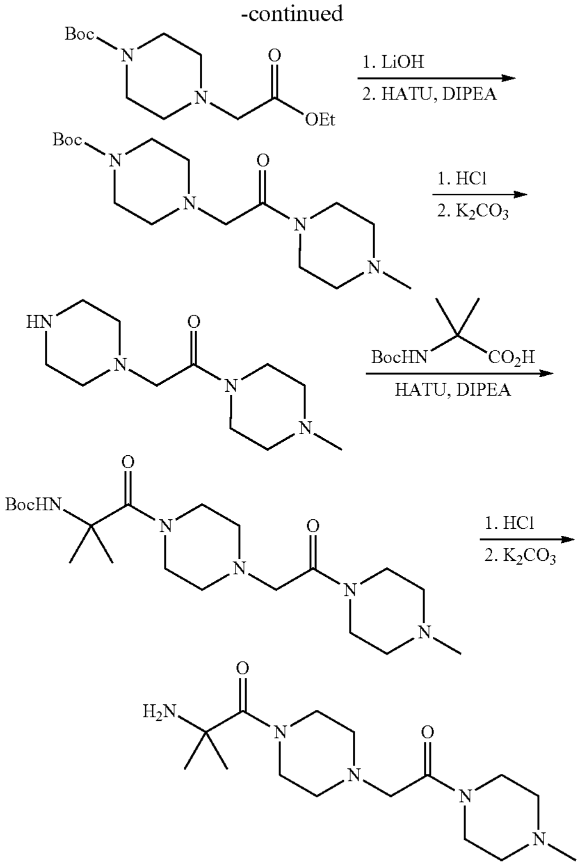

Step 1

Tert-butyl piperazine-1-carboxylate (5 g), acetonitrile (50 ml), ethyl bromoacetate (4.7 g) and caesium carbonate (7.42 g) were successively added into a 100 ml reaction flask, stirred at room temperature for 3 h, and monitored by TLC. The reaction liquid was filtered with silica gel, eluted with ethyl acetate and concentrated to obtain 7.63 g of white solid. MS: m/z 273.2, $[M+H]^+$.

Step 2

The product of the previous step (5 g), tetrahydrofuran (20 ml), water (2 ml) and lithium hydroxide monohydrate (848 mg) were added into a 100 ml reaction flask, reacted at 60° C. for 2 h, and monitored by TLC. The reaction solution was concentrated to dryness, and added with toluol for azeotropic concentration to dryness to obtain 4.4 g of white solid. Methylpiperazine (1.76 g), DIPEA (6.8 g), methylene chloride (40 ml) and HATU (7.4 g) were successively added into the concentrate, and reacted at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 3.9 g of colorless oily liquid. MS: m/z 327.2, $[M+H]^+$.

Step 3

The product of the previous step (3.5 g, 10.7 mmol), acetonitrile (20 ml), concentrated hydrochloric acid (10 ml) and methanol (2 ml) were added into a 100 ml reaction flask, stirred at room temperature, and TLC monitored that the raw materials were completed reacted. The reaction solution was concentrated to dryness, dissolved in acetonitrile (20 ml), added with potassium carbonate (5.9 g), and stirred at 35° C. for 2 h. The reaction solution was cooled to room temperature, filtered with diatomite, and washed with acetonitrile. The filtrate was concentrated to dryness to obtain 2.33 g of colorless oily liquid.

Step 4

2-((tert-butoxycarbonyl)amino)-2-methylpropionic acid (2.1 g), DIPEA (3.9 g), methylene chloride (40 ml) and HATU (4.2 g) were successively added into a 100 ml reaction flask, stirred at room temperature for 20 min, added with the product of the previous step (2.3 g), and reacted at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 2.8 g of pale yellow oily liquid.

Step 5

The product of the previous step (2.8 g), acetonitrile (10 ml), concentrated hydrochloric acid (8 ml) and methanol (1 ml) were added into a 100 ml reaction flask, stirred at room temperature, and TLC monitored that the raw materials were completed reacted. The reaction solution was concentrated to dryness, dissolved in acetonitrile (10 ml), added with potassium carbonate (3.8 g, 27.2 mmol), and stirred at 35° C. for 2 h. The reaction solution was cooled to room temperature, filtered with diatomite, and washed with acetonitrile. The filtrate was concentrated to dryness to obtain 1.22 g of white waxy solid.

Intermediate: 4-(2-amino-2-methylpropionyl)-N,N-dimethylpiperazine-1-formamide

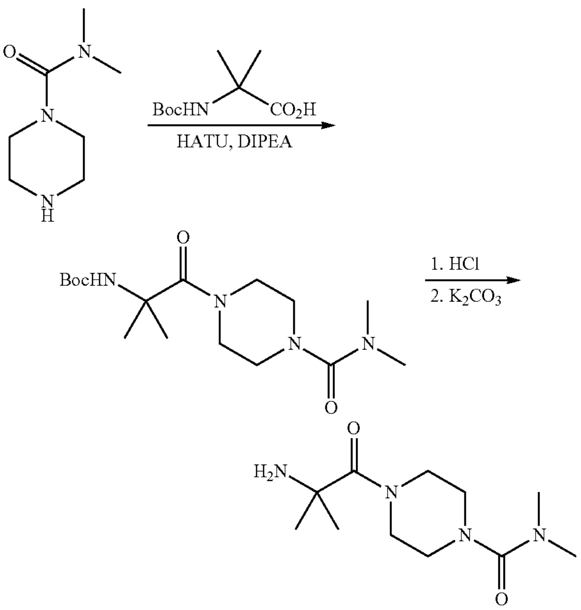

Step 1

2-((tert-butoxycarbonyl)amino)-2-methylpropionic acid (1.3 g), DIPEA (2.4 g), methylene chloride (20 ml) and HATU (2.7 g) were successively added into a 100 ml reaction flask, stirred at room temperature for 20 min, added with N,N-dimethylpiperazine-1-formamide (1 g), and reacted at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 1.26 g of pale yellow oily liquid.

Step 2

The product of the previous step (1.26 g), acetonitrile (10 ml), concentrated hydrochloric acid (8 ml) and methanol (1 ml) were added into a 100 ml reaction flask, stirred at room temperature, and TLC monitored that the raw materials were completed reacted. The reaction solution was concentrated to dryness, dissolved in acetonitrile for resolution, added with potassium carbonate (2 g), and stirred at 35° C. for 2 h. The reaction solution was cooled to room temperature, filtered with diatomite, and washed with acetonitrile. The filtrate was concentrated to dryness to obtain 876 mg of white solid.

Intermediate: 2-amino-2-methyl-N-(2-(1,3,3-trimethylurea)ethyl) Propionamide

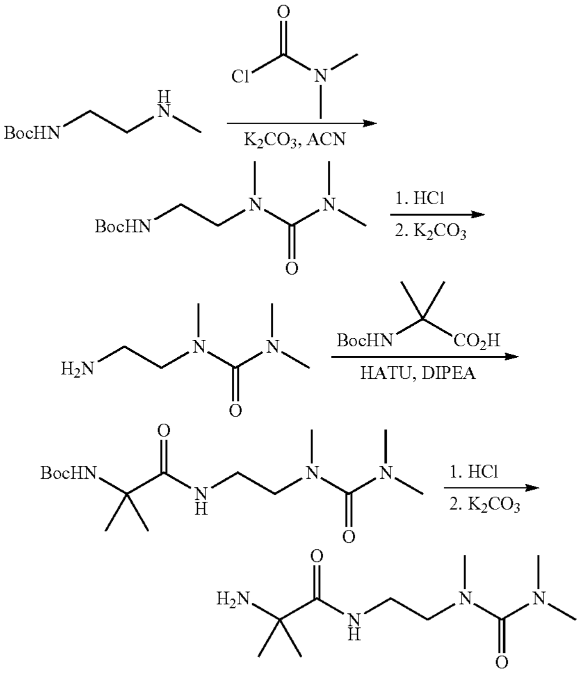

Step 1

Tert-Butyl (2-(methylamino)ethyl)carbamate (5 g), acetonitrile (50 ml), dimethylcarbamoyl chloride (3.1 g) and potassium carbonate (7.42 g) were successively added into a 100 ml reaction flask, and stirred at room temperature for 3 h. The reaction liquid was filtered with silica gel, eluted with ethyl acetate and concentrated to obtain 6.7 g of white solid.

Step 2

The product of the previous step (5 g), acetonitrile (20 ml), concentrated hydrochloric acid (10 ml) and methanol (2 ml) were added into a 100 ml reaction flask, stirred at room temperature, and TLC monitored that the raw materials were completely transformed. The reaction solution was concentrated to dryness, dissolved in acetonitrile (20 ml), added with potassium carbonate (11.27 g), and stirred at 35° C. for 2 h. The reaction solution was cooled to room temperature, filtered with diatomite, and washed with acetonitrile. The filtrate was concentrated to dryness to obtain 2.64 g of colorless oily liquid.

Step 3

2-((tert-butoxycarbonyl)amino)-2-methylpropionic acid (3.1 g), DIPEA (5.9 g), methylene chloride (40 ml) and HATU (6.34 g) were successively added into a 100 ml reaction flask, stirred at room temperature for 20 min, added with the product of the previous step (2.2 g), and reacted at room temperature for 3 h after the addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 2.75 g of colorless waxy solid.

Step 4

The product of the previous step (1.85 g), acetonitrile (10 ml), concentrated hydrochloric acid (8 ml) and methanol (1 ml) were added into a 100 ml reaction flask, stirred at room temperature, and TLC monitored that the raw materials were completely transformed. The reaction solution was concentrated to dryness, dissolved in acetonitrile (10 ml), added with potassium carbonate (3.1 g), and stirred at 35° C. for 2 h. The reaction solution was cooled to room temperature, filtered with diatomite, and washed with acetonitrile. The filtrate was concentrated to dryness to obtain 1.26 g of white waxy solid.

Intermediate 6: 2-amino-2-methyl-N-(2-((2-oxo-2-(pyrrolidine-1-yl)ethyl(prop-2-yn-1-yl)amino)ethyl) propionamide

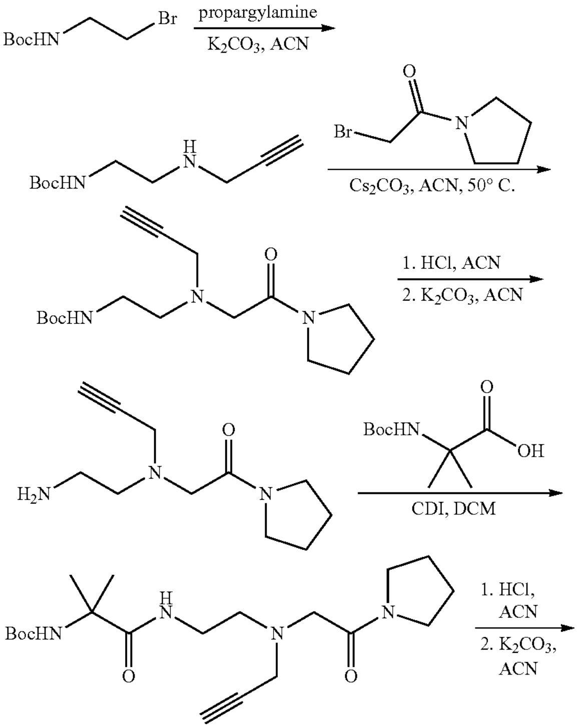

-continued

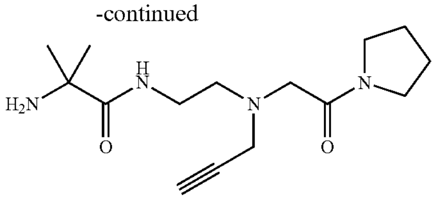

Tert-butyl (2-(prop-2-yn-1-ylamino)ethyl)carbamate 2-(Boc-amino)ethyl bromide (6.0 g), acetonitrile (100 ml), potassium carbonate (7.4 g) and propargylamine (1.62 g, 29.4 mmol) were successively added into a 100 ml flask, heated to 35° C., and stirred for 10 h. The reaction solution was filtered, the filtrate was diluted with water, extracted with dichloromethane for three times, and the organic phases were combined, washed once with saturated salt solution, dried with anhydrous sodium sulfate, and concentrated under reduced pressure to obtain 5.0 g of pale yellow liquid.

2-((2-aminoethyl)(prop-2-yn-1-yl)amino)-1-(pyrrolidine-1-yl)ethyl-1-one

Tert-butyl (2-(prop-2-yn-1-yl-amino)ethyl)carbamate (5.0 g), 1-(bromoacetyl)-pyrrolidine (4.87 g), caesium carbonate (16.6 g) and acetonitrile (50 ml) were successively added into a 100 ml flask, heated to 50° C., and stirred for 8 h. The reaction solution was cooled to room temperature and filtered. The filtrate was concentrated to dryness and purified by column chromatography to obtain 5.0 g of pale yellow oily liquid. The product was dissolved in acetonitrile (20 ml), slowly dropwise added with concentrated hydrochloric acid (5 ml), and stirred at room temperature for 1 h. The reaction solution was concentrated to dryness, dissolved in acetonitrile (20 ml), added with potassium carbonate (8.56 g), and stirred at 35° C. for 3 h. The reaction solution was cooled to room temperature, filtered with diatomite, and washed with acetonitrile. The filtrate was concentrated under reduced pressure to obtain 2.5 g of pale yellow oily liquid.

2-amino-2-methyl-N-(2-((2-oxo-2-(pyrrolidine-1-yl)ethyl(prop-2-yn-1-yl)amino)ethyl)propionamide 2-((tert-butoxycarbonyl)amino)-2-methylpropionic acid (2.5 g) and dichloromethane (25 ml) were added into a 50 ml reaction flask successively, cooled to 0° C. in an ice bath, and slowly added with CDI (2.28 g). After the addition, the mixture was stirred at 0° C. for 30 min. The reaction solution was added with 2-((2-aminoethyl)(prop-2-yn-1-yl)amino)-1-(pyrrolidine-1-yl)ethyl-1-one (2.5 g), and returned to room temperature and stirred for 3 h after the addition. The reaction solution was diluted with dichloromethane, and added with water for liquid separation. The aqueous phase was extracted with dichloromethane for three times, and the organic phases were combined, washed once with saturated salt solution, dried with anhydrous sodium sulfate, concentrated under reduced pressure, and purified by column chromatography (dichloromethane:methanol=20:1) to obtain 1.42 g of pale yellow oily substance. The product was dissolved in acetonitrile (10 ml), slowly dropwise added with concentrated hydrochloric acid (3 ml), and stirred at room temperature for 1 h. The reaction solution was concentrated to dryness, dissolved in acetonitrile (10 ml), added with potassium carbonate (1.99 g), and stirred at 35° C. for 3 h. The reaction solution was cooled to room temperature, filtered with diatomite, and washed with acetonitrile. The filtrate was concentrated to dryness under reduced pressure to obtain 0.75 g of pale yellow oily substance. MS: m/z 295.2, $[M+H]^+$.

Preparation of Compounds

Example 1

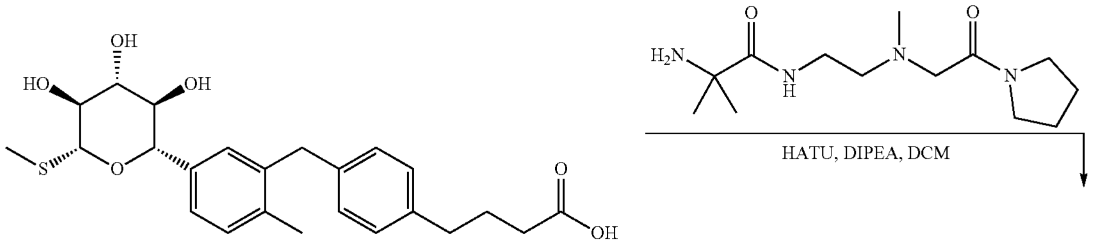

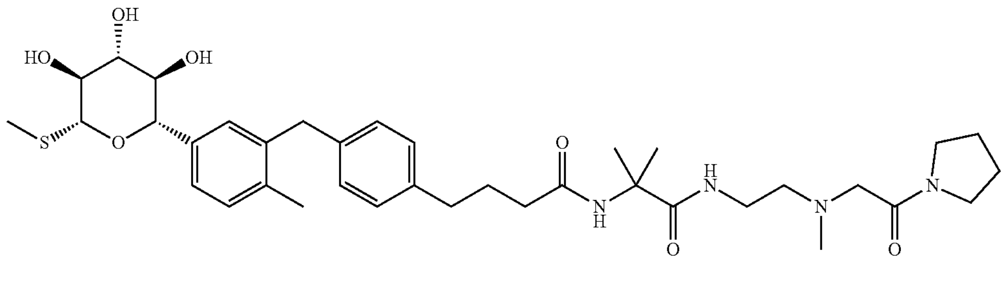

4-(4-(2-methyl-5-((2S,3R,4R,5S,6R)-3,4,5-trihydroxy-6-(methylthio)tetrahydro-2H-pyran-2-yl)benzyl)phenyl)butyric acid (100 mg), 2-amino-2-methyl-N-(2-(methyl(2-oxo-2-(pyrrolidine-1-yl)ethyl)amino)ethyl)propionamide (59.5 mg), DIPEA (85 mg), dichloromethane (40 ml) and HATU (6.34 g) were added into a 100 ml reaction flask, and stirred at room temperature for 3 h after the addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 70 mg of pale yellow solid. $^1$H NMR (400 MHz, $CD_3OD$): δ=7.24-7.02 (m, 7H), 4.41 (d, J=9.4 Hz, 1H), 4.15 (d, J=9.1 Hz, 1H), 3.98 (s, 2H), 3.52-3.33 (m, 8H), 3.25 (t, J=6.1 Hz, 2H), 3.16 (s, 2H), 2.65-2.51 (m, 4H), 2.28 (s, 2H), 2.26-2.19 (m, 5H), 2.16 (s, 3H), 1.97-1.78 (m, 6H), 1.45 (s, 6H). MS: m/z 699.4, $[M+H]^+$.

Example 2

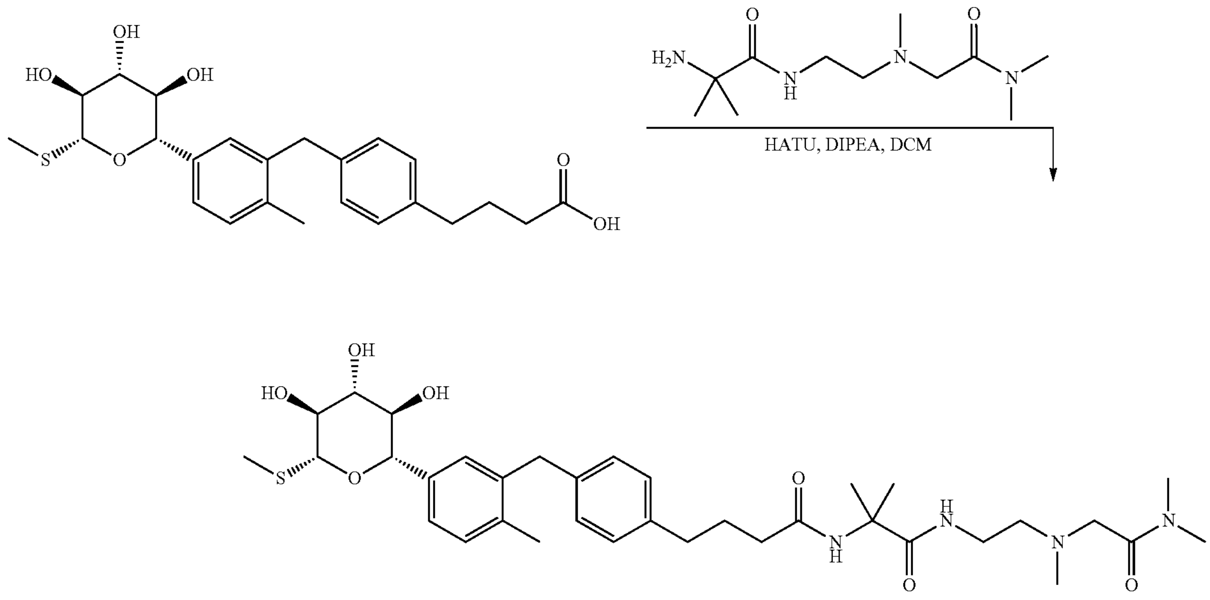

4-(4-(2-methyl-5-((2S,3R,4R,5S,6R)-3,4,5-trihydroxy-6-(methylthio)tetrahydro-2H-pyran-2-yl)benzyl)phenyl)butyric acid (100 mg), 2-amino-N-(2-(2-(dimethylamino)-2-oxoethyl)(methyl)amino)ethyl)-2-methylpropionamide (54 mg), DIPEA (85 mg), dichloromethane (40 ml) and HATU (92 mg) were added into a 100 ml reaction flask, and stirred at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by silica gel column chromatography to obtain 68 mg of pale yellow solid. $^1$H NMR (400 MHz, $CD_3OD$): δ=7.23-7.02 (m, 7H), 4.41 (d, J=9.4 Hz, 1H), 4.15 (d, J=9.2 Hz, 1H), 3.98 (s, 2H), 3.61 (t, J=5.4 Hz, 2H), 3.52-3.33 (m, 5H), 3.02 (s, 3H), 2.99 (s, 3H), 2.95 (s, 3H), 2.60 (t, J=7.6 Hz, 2H), 2.31-2.19 (m, 5H), 2.16 (s, 3H), 1.93-1.81 (m, 2H), 1.44 (s, 6H). MS: m/z 673.4, $[M+H]^+$.

Example 3

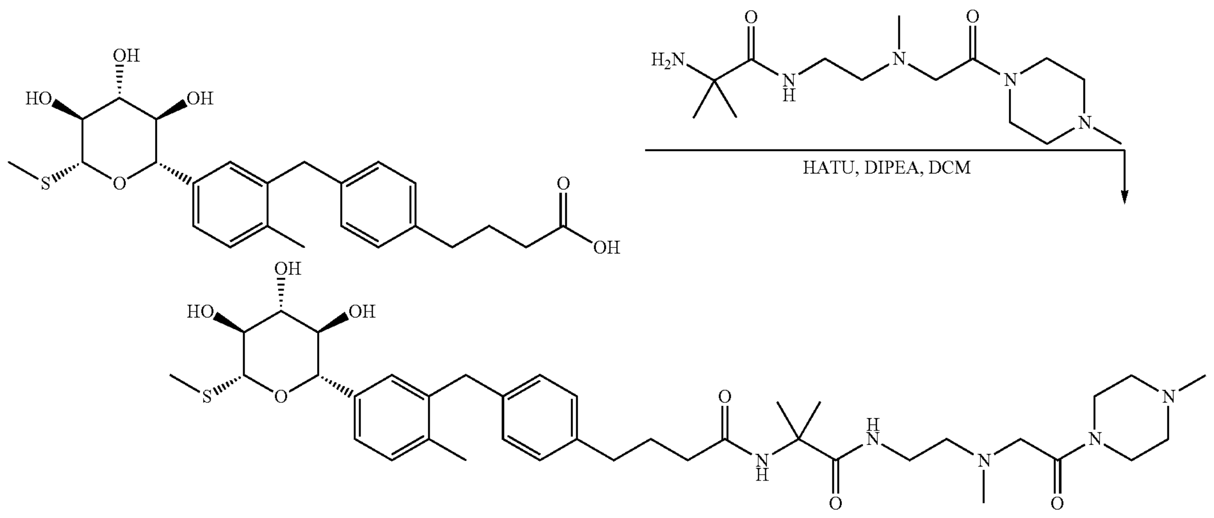

4-(4-(2-methyl-5-((2S,3R,4R,5S,6R)-3,4,5-trihydroxy-6-(methylthio)tetrahydro-2H-pyran-2-yl)benzyl)phenyl)butyric acid (100 mg), 2-amino-2-methyl-N-(2-(methyl(2-(4-methylpiperazine-1-yl)-2-oxoethyl)amino)ethyl) propionamide (66 mg), DIPEA (85 mg), dichloromethane (40 ml) and HATU (92 mg) were added into a 100 ml reaction flask, and stirred at room temperature for 3 h after the addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 50 mg of pale yellow solid. MS: m/z 728.4, $[M+H]^+$.

Example 4

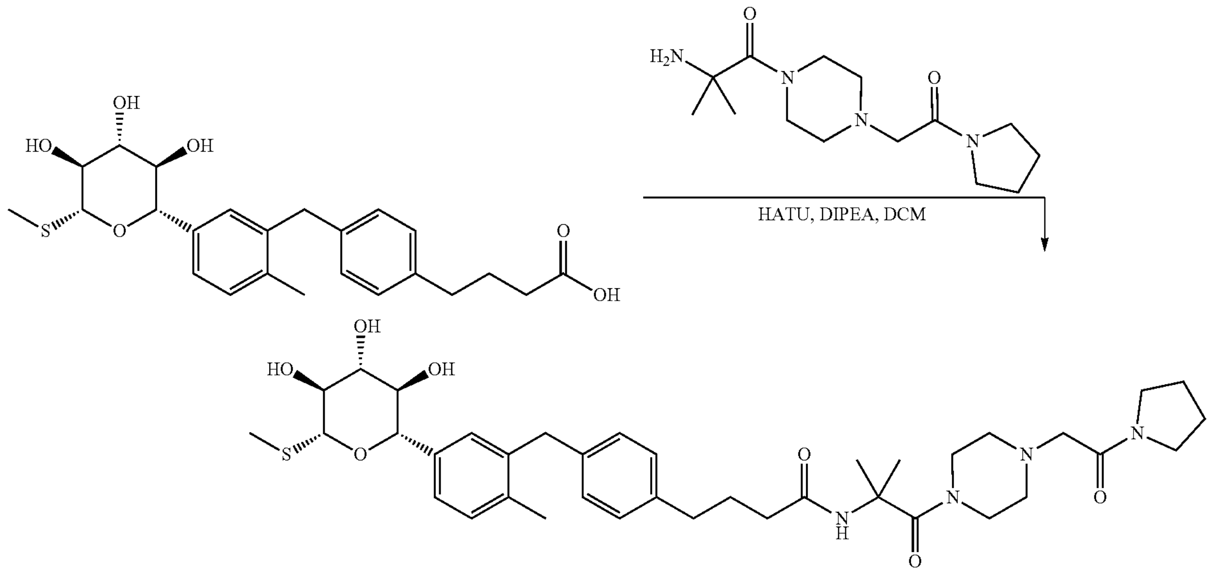

4-(4-(2-methyl-5-((2S,3R,4R,5S,6R)-3,4,5-trihydroxy-6-(methylthio)tetrahydro-2H-pyran-2-yl)benzyl)phenyl)butyric acid (100 mg), 2-amino-2-methyl-1-(4-(2-oxo-2-(pyrrolidine-1-yl)ethyl)piperazin-1-yl)propane-1-one (62.15 mg), DIPEA (85 mg), dichloromethane (40 ml) and HATU (92 mg) were added into a 100 ml reaction flask, and stirred at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 110 mg of pale yellow waxy solid. $^1$H NMR (400 MHz, $CDCl_3$): δ=7.21-7.00 (m, 7H), 4.40 (d, J=9.4 Hz, 1H), 4.16 (d, J=9.3 Hz, 1H), 3.94 (s, 2H), 3.72-3.60 (m, 4H), 3.57-3.38 (m, 8H), 2.61 (t, J=7.1 Hz, 2H), 2.57-2.47 (m, 4H), 2.26 (s, 3H), 2.20-2.10 (m, 5H), 2.08 (s, 2H), 1.99-1.78 (m, 6H), 1.52 (s, 6H). MS: m/z 711.4, $[M+H]^+$.

Example 5

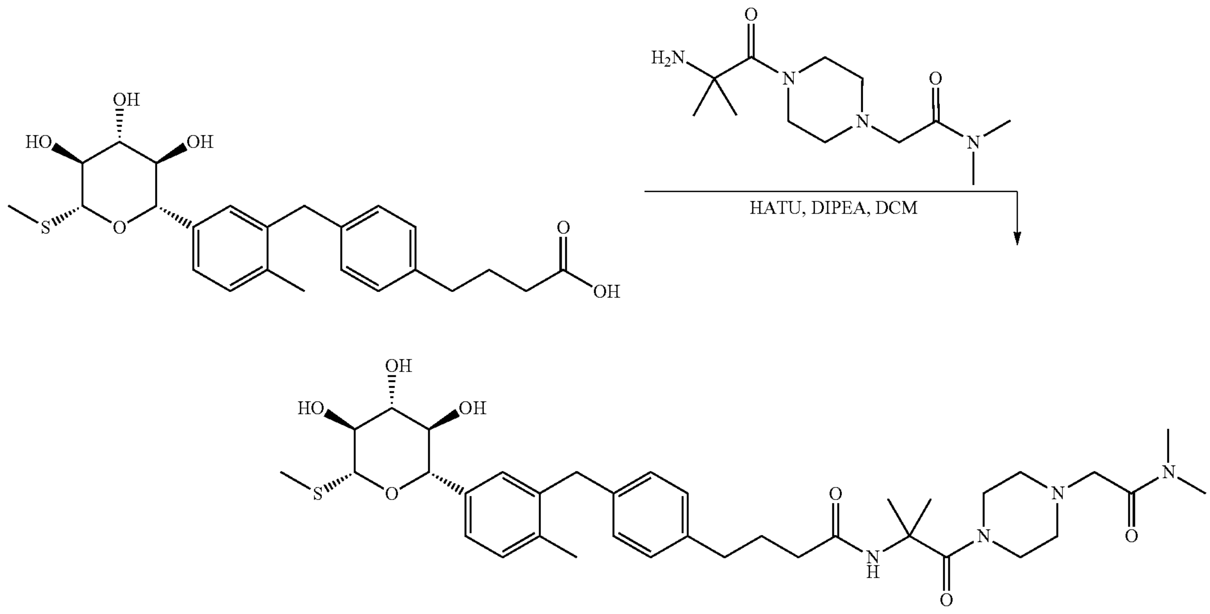

4-(4-(2-methyl-5-((2S,3R,4R,5S,6R)-3,4,5-trihydroxy-6-(methylthio)tetrahydro-2H-pyran-2-yl)benzyl)phenyl)butyric acid (100 mg), 2-(4-(2-amino-2-methylpropionyl)piperazin-1-yl)-N,N-dimethylacetamide (56 mg), DIPEA (85 mg), dichloromethane (40 ml) and HATU (92 mg) were added into a 100 ml reaction flask, and stirred at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 74 mg of pale yellow solid. $^1$H NMR (400 MHz, $CDCl_3$): δ=7.16-6.95 (m, 7H), 4.34 (d, J=9.5 Hz, 1H), 4.16 (d, J=9.4 Hz, 1H), 3.89 (s, 2H), 3.67-3.55 (m, 4H), 3.54-3.40 (m, 3H), 3.15-3.10 (m, 2H), 2.98 (s, 3H), 2.88 (s, 3H), 2.55 (t, J=7.4 Hz, 1H), 2.49-2.39 (m, 4H), 2.20 (s, 3H), 2.15-2.06 (m, 5H), 1.90-1.77 (m, 2H), 1.42 (s, 6H). MS: m/z 685.4, $[M+H]^+$.

Example 6

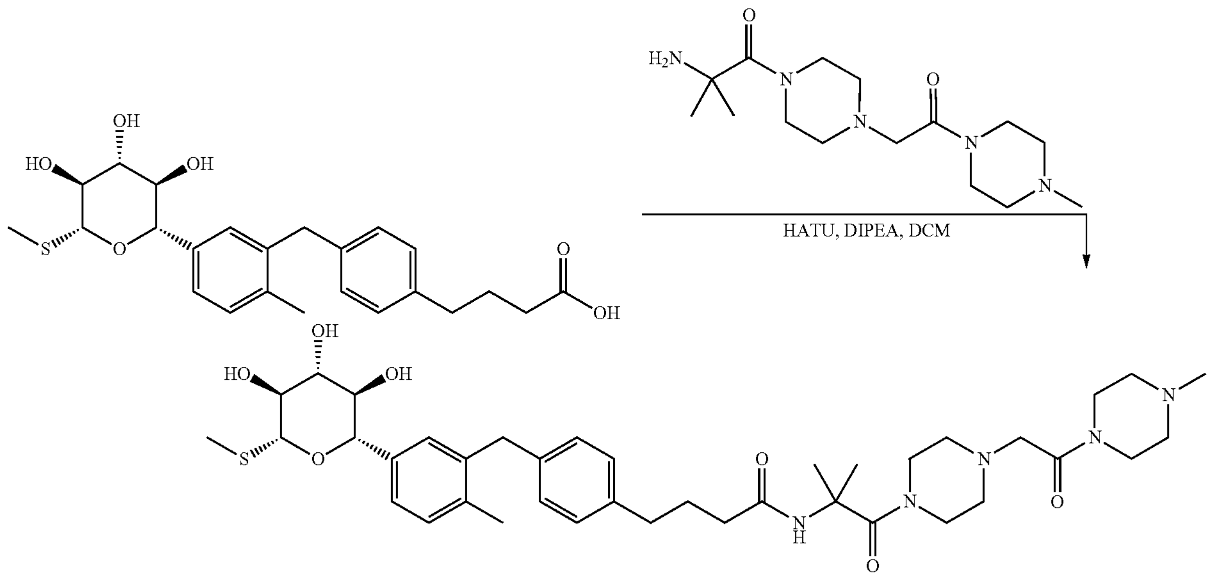

4-(4-(2-methyl-5-((2S,3R,4R,5S,6R)-3,4,5-trihydroxy-6-(methylthio)tetrahydro-2H-pyran-2-yl)benzyl)phenyl)butyric acid (100 mg), 2-amino-2-methyl-1-(4-(2-(4-methylpiperazine-1-yl)-2-oxoethyl)piperazin-1-yl)propane-1-one (69 mg), DIPEA (85 mg), dichloromethane (40 ml) and HATU (92 mg) were added into a 100 ml reaction flask, and stirred at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 74 mg of pale yellow solid. MS: m/z 740.4, $[M+H]^+$.

Example 7

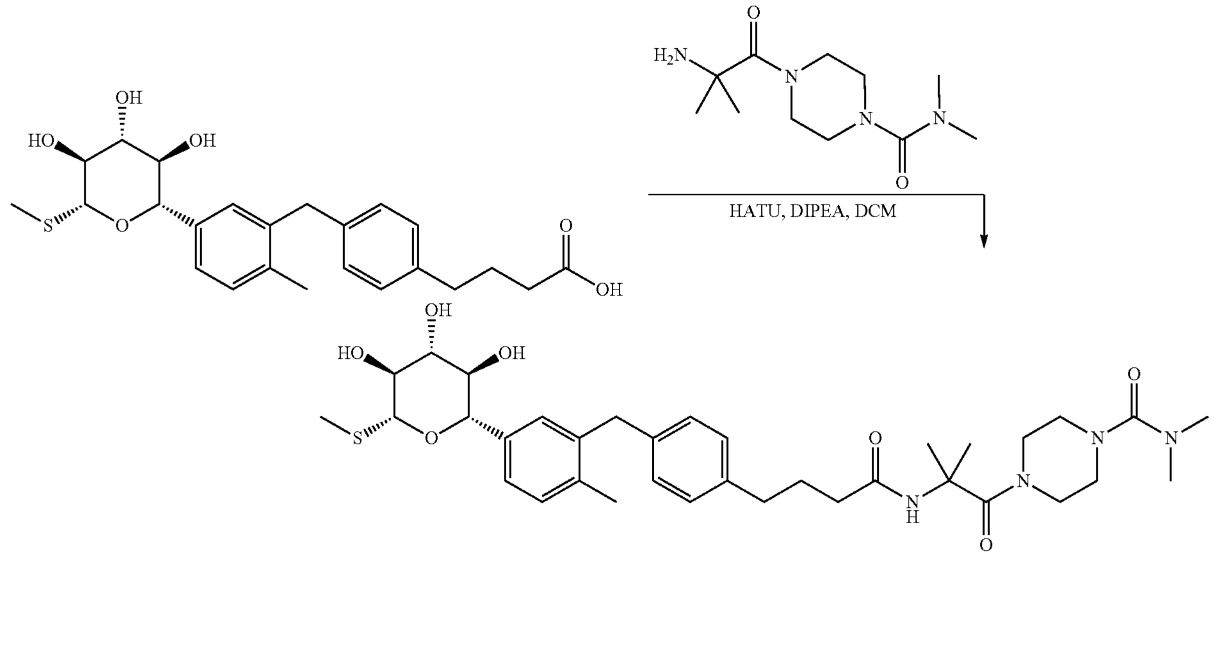

4-(4-(2-methyl-5-((2S,3R,4R,5S,6R)-3,4,5-trihydroxy-6-(methylthio)tetrahydro-2H-pyran-2-yl)benzyl)phenyl)butyric acid (100 mg), 4-(2-amino-2-methylpropionyl)-N,N-dimethylpiperazine-1-formamide (53 mg), DIPEA (85 mg), dichloromethane (40 ml) and HATU (92 mg) were added into a 100 ml reaction flask, and stirred at room temperature for 3 h after the addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 84 mg of pale yellow solid. MS: m/z 693.3, $[M+Na]^+$.

Example 8

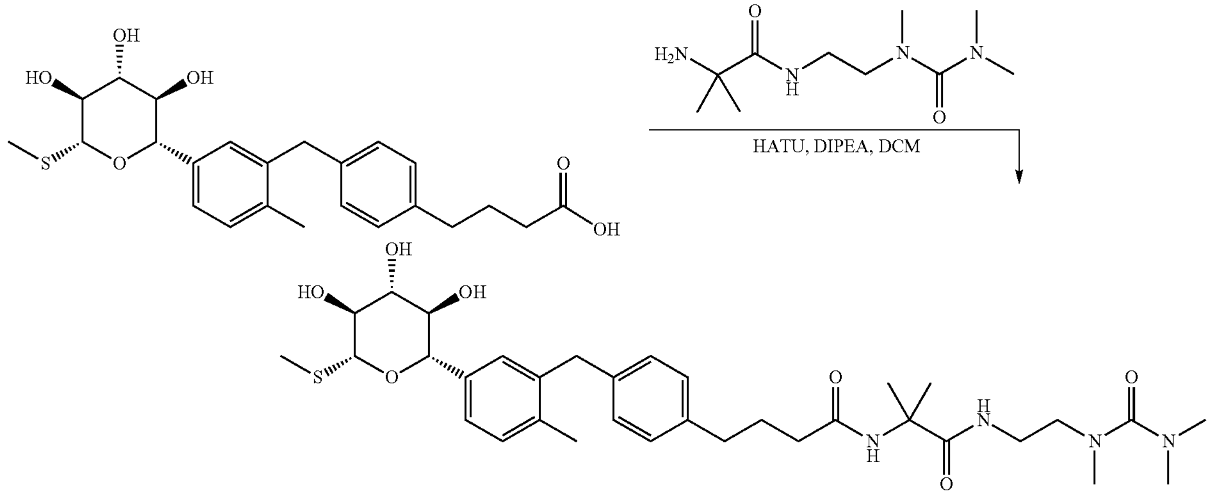

4-(4-(2-methyl-5-((2S,3R,4R,5S,6R)-3,4,5-trihydroxy-6-(methylthio)tetrahydro-2H-pyran-2-yl)benzyl)phenyl)butyric acid (100 mg), 2-amino-2-methyl-N-(2-(1,3,3-trimethylurea)ethyl) propionamide (51 mg), DIPEA (85 mg), dichloromethane (40 ml) and HATU (92 mg) were added into a 100 ml reaction flask, and stirred at room temperature for 3 h after addition. The reaction system was added with ammonium chloride aqueous solution for quenching, and extracted with dichloromethane for three times. The organic phases were combined, washed once with saturated salt solution, dried with anhydrous sodium sulfate, concentrated to dryness under reduced pressure, and purified by column chromatography to obtain 55 mg of pale yellow solid. MS: m/z 659.4, [M+H]‴.

Example 9

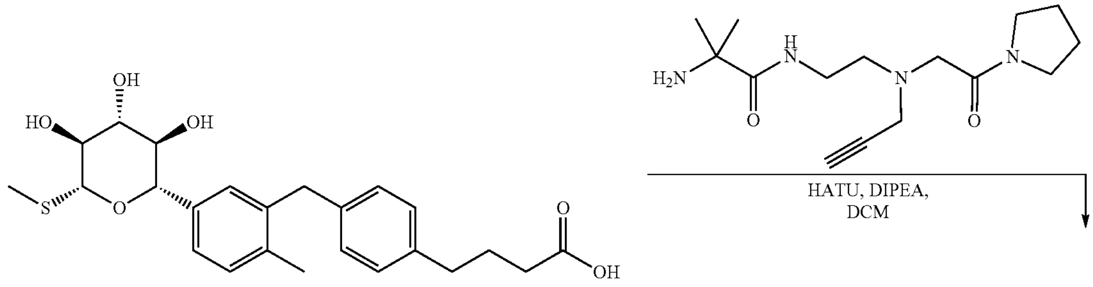

-continued

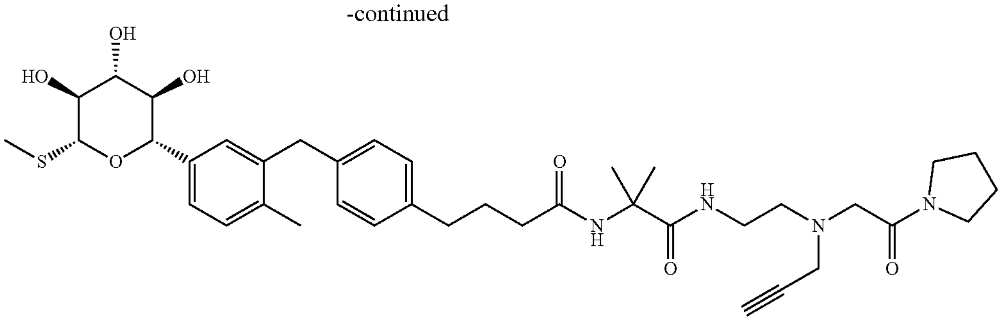

4-(4-(2-methyl-5-((2S,3R,4R,5S,6R)-3,4,5-trihydroxy-6-(methylthio)tetrahydro-2H-pyran-2-yl)benzyl)phenyl)butyric acid (89 mg), N,N-dimethylformamide (5 ml), N,N-diisopropylethylamine (52 mg), 2-amino-2-methyl-N-(2-((2-oxo-2-(pyrrolidine-1-yl)ethyl(prop-2-yn-1-yl)amino) ethyl)propionamide (65 mg), and 2-(7-benzotriazole oxide)-N,N,N',N'-tetramethylurea hexafluorophosphate (84 mg) were added into a 25 ml reaction flask, and stirred at room temperature for 2 h. The reaction solution was diluted with dichloromethane, and washed with water. The aqueous phase was extracted with dichloromethane for three times, and the organic phases were combined, washed with saturated salt solution, dried with anhydrous sodium sulfate, and filtered. The filtrate was concentrated to dryness, and purified by column chromatography to obtain 120 mg of white solid. $^1$H NMR (400 MHz, DMSO-d6): δ 7.81 (s, 1H), 7.52 (t, J=5.0 Hz, 1H), 7.12-7.04 (m, 7H), 5.23 (d, J=5.6 Hz, 1H), 5.13 (d, J=4.6 Hz, 1H), 4.88 (d, J=5.5 Hz, 1H), 4.33 (d, J=9.4 Hz, 1H), 4.05 (d, J=9.1 Hz, 1H), 3.91 (s, 2H), 3.41-3.34 (m, 3H), 3.30-3.16 (m, 7H), 3.12 (br s, 1H), 3.09-3.04 (m, 2H), 2.54-2.48 (m, 2H), 2.18 (s, 3H), 2.10 (t, J=7.4 Hz, 2H), 2.04 (s, 3H), 1.87-1.79 (m, 2H), 1.75-1.70 (m, 4H), 1.30 (s, 6H). $^{13}$C NMR (100 MHz, DMSO-d6): δ 174.5, 172.0, 168.3, 139.8, 138.8, 138.0, 137.8, 135.8, 130.1, 129.7, 128.9, 128.7, 126.0, 85.8, 81.8, 79.8, 78.6, 76.2, 74.8, 72.7, 56.1, 55.4, 52.5, 45.9, 45.7, 42.6, 38.8, 37.6, 35.5, 34.8, 27.4, 26.2, 25.7, 24.1, 19.5, 11.5. MS: m/z 723.4, [M+H]$^+$.

Example 10

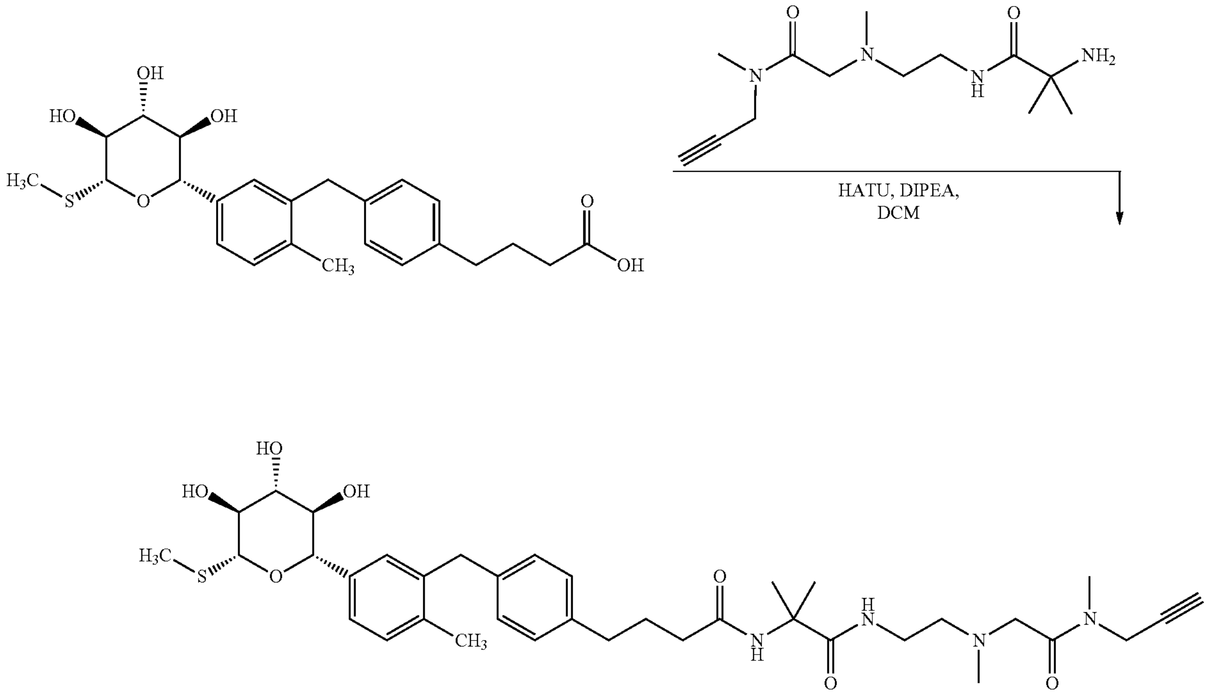

4-(4-(2-Methyl-5-((2S,3R,4R,5S,6R)-3,4,5-trihydroxy-6-(methylthio)tetrahydro-2H-pyran-2-yl)benzyl)phenyl)butyric acid (prepared by the method of Reference Journal of Medicinal Chemistry 2017, 60, 710-721) (89 mg), N,N-dimethylformamide (5 ml), N,N-diisopropylethylamine (52 mg), 2-amino-2-methyl-N-(2-((2-oxo-2-(pyrrolidine-1-yl)ethyl(prop-2-yn-1-yl)amino)ethyl)propionamide (59 mg), and 2-(7-benzotriazole oxide)-N,N,N',N'-tetramethylurea hexafluorophosphate (84 mg) were added into a 25 ml reaction flask, and stirred at room temperature for 2 h. The reaction solution was diluted with dichloromethane, and washed with water. The aqueous phase was extracted with dichloromethane for three times, and the organic phases were combined, washed with saturated salt solution, dried with anhydrous sodium sulfate, and filtered. The filtrate was concentrated to dryness, and purified by column chromatography to obtain white solid (53 mg). $^1$H NMR (400 MHz, $CDCl_3$): δ ppm 7.85-7.72 (m, 1H), 7.20-7.02 (m, 7H), 6.89-6.65 (m, 1H), 4.41-4.38 (d, J=9.5 Hz, 1H), 4.20 (d, J=2.3 Hz, 1H), 4.17-4.14 (d, J=9.4 Hz, 1H), 3.94 (s, 2H), 3.67-3.63 (t, J=8.8 Hz, 1H), 3.55-3.47 (m, 2H), 3.32-3.24 (m, 4H), 3.03-2.97 (m, 3H), 2.63-2.59 (t, J=7.2 Hz, 2H), 2.56-2.53 (t, J=5.3 Hz, 2H), 2.32 (s, 3H), 2.27 (s, 3H), 2.25-2.24 (t, J=2.4 Hz, 1H), 2.20-2.10 (m, 6H), 1.96-1.89 (m, 2H), 1.57 (s, 6H). $^{13}$C NMR (100 MHz, $CDCl_3$): δ ppm 175.3, 172.7, 170.3, 139.5, 139.2, 137.8, 136.8, 135.6, 130.3, 129.0, 128.8, 128.7, 125.5, 85.6, 81.9, 77.9, 74.8, 72.3, 72.1, 58.7, 56.9, 55.7, 42.8, 38.8, 38.1, 36.5, 36.1, 34.6, 33.5, 29.7, 27.1, 25.0, 19.5, 11.7; MS: m/z 697.4, $[M+H]^+$.

Example 11

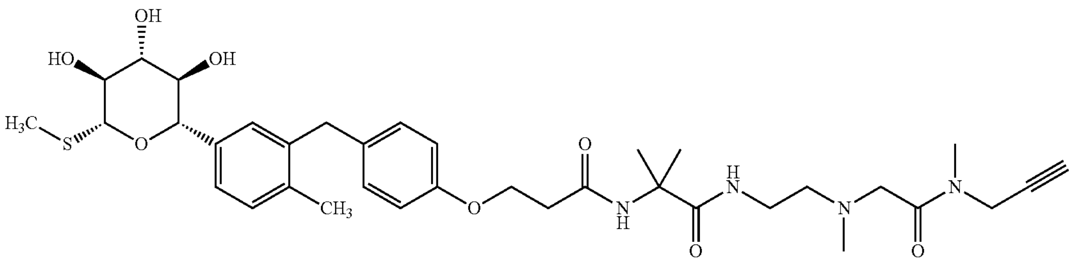 [SMILES: C#CCN(C)C(=O)CN(C)CCNC(=O)C(C)(C)NC(=O)CCOc1ccc(Cc2cc([C@@H]3O[C@H](SC)[C@@H](O)[C@H](O)[C@H]3O)ccc2C)cc1]

The compound was obtained by referring to the similar preparation scheme in Example 1. ESI-MS: 699.1 $[M+H]^+$. The specific preparation method was as follows:

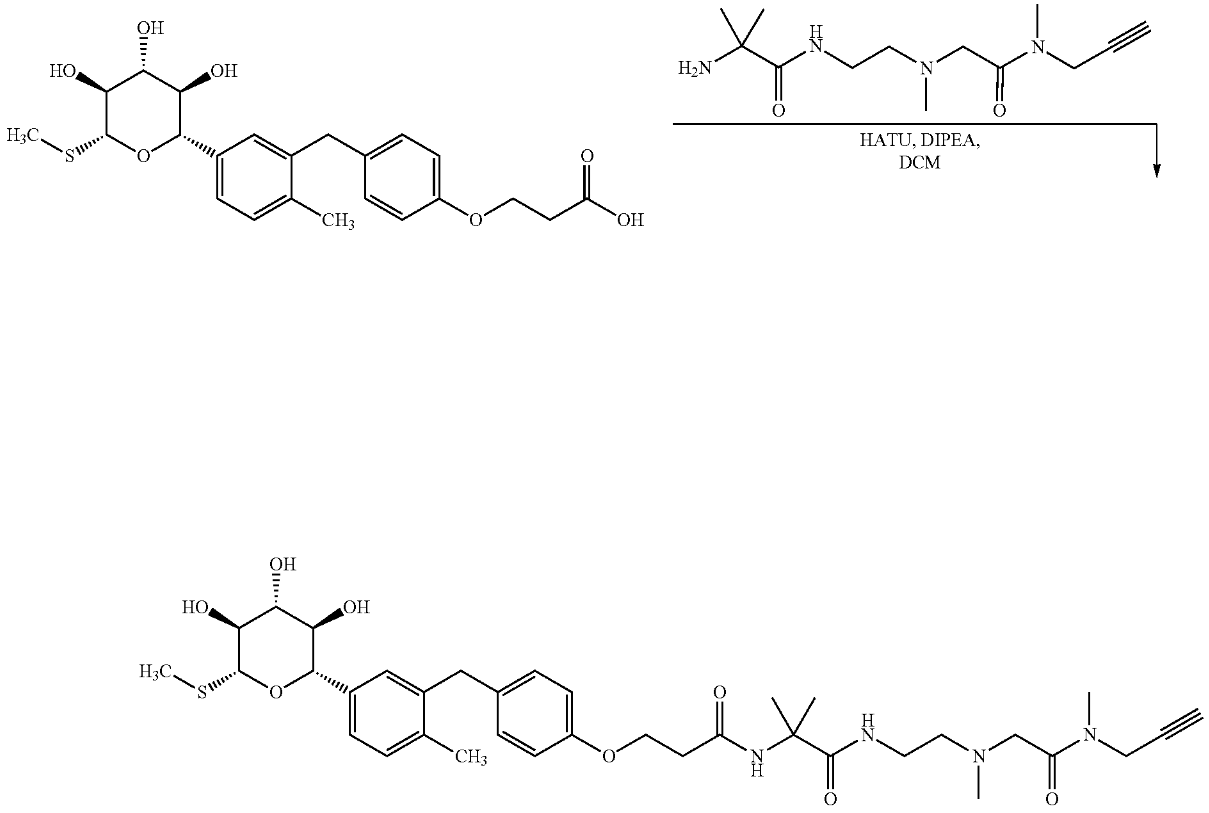

3-(4-(2-Methyl-5-((2S,3R,4R,5S,6R)-3,4,5-trihydroxy-6-(methylthio)tetrahydro-2H-pyran-2-yl)benzyl)phenyloxy) propionic acid (70 mg), N,N-dimethylformamide (5 ml), N,N-diisopropylethylamine (45 mg), 2-(4-(2-amino-2-methylpropionyl)piperazin-1-yl)-N-methyl-N-(prop-2-yn-1-yl) acetamide (65 mg), and 2-(7-benzotriazole oxide)-N,N,N',N'-tetramethylurea hexafluorophosphate (70 mg) were added into a 25 ml reaction flask, and stirred at room temperature for 2 h after addition. The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 40 mg of off-white solid.

Example 12

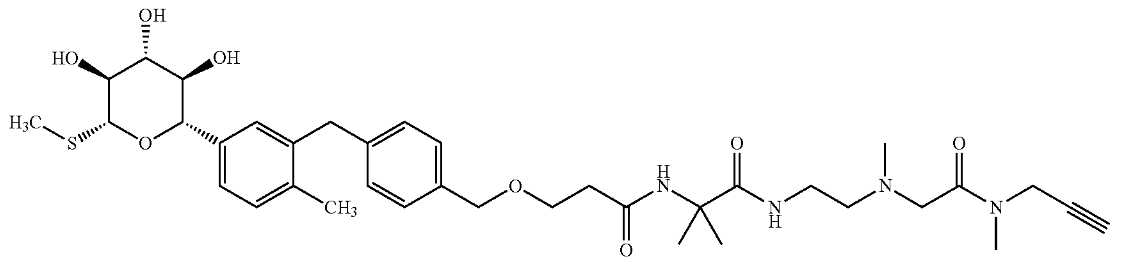 [SMILES: C#CCN(C)C(=O)CN(C)CCNC(=O)C(C)(C)NC(=O)CCOCc1ccc(Cc2cc([C@@H]3O[C@H](SC)[C@@H](O)[C@H](O)[C@H]3O)ccc2C)cc1]

The compound was obtained by referring to the similar preparation scheme in Example 1. ESI-MS: 713.3 $[M+H]^+$.

The specific preparation method was as follows:

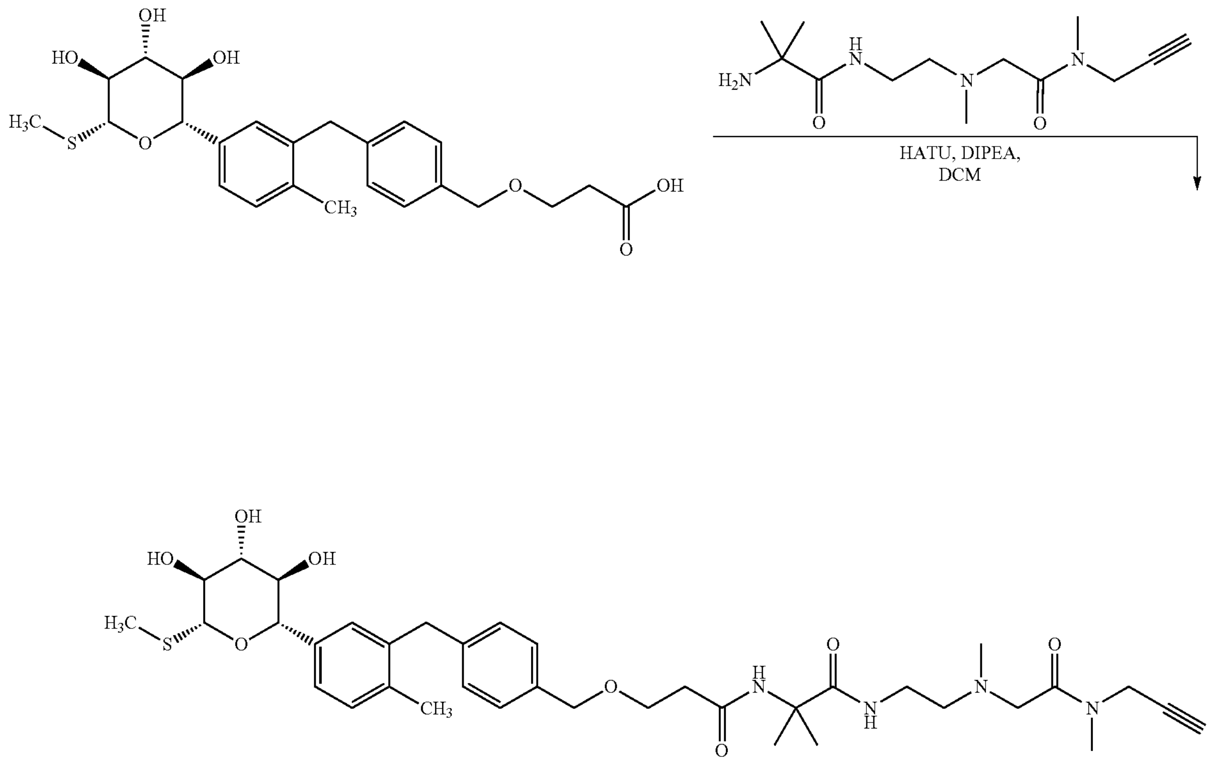

3-(4-(2-Methyl-5-((2S,3R,4R,5S,6R)-3,4,5-trihydroxy-6-(methylthio)tetrahydro-2H-pyran-2-yl)benzyl)benzyl)oxy) propionic acid (85 mg), N,N-dimethylformamide (5 ml), N,N-diisopropylethylamine (50 mg), 2-(4-(2-amino-2-methylpropionyl)piperazin-1-yl)-N-methyl-N-(prop-2-yn-1-yl) acetamide (55 mg), and 2-(7-benzotriazole oxide)-N,N,N',N'-tetramethylurea hexafluorophosphate (80 mg) were added into a 25 ml reaction flask, and stirred at room temperature for 2 h after the addition. The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 42 mg of white solid.

Example 13

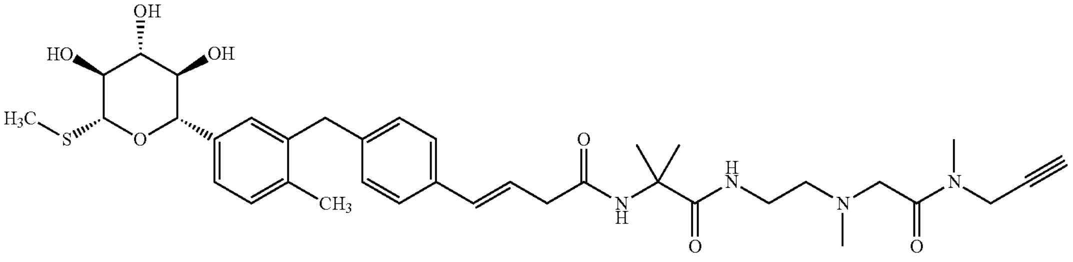 [SMILES: C#CCN(C)C(=O)CN(C)CCNC(=O)C(C)(C)NC(=O)C/C=C/c1ccc(Cc2cc([C@@H]3O[C@H](SC)[C@@H](O)[C@H](O)[C@H]3O)ccc2C)cc1]

The compound was obtained by referring to the similar preparation scheme in Example 1. ESI-MS: 695.5 $[M+H]^+$.

The specific preparation method was as follows:

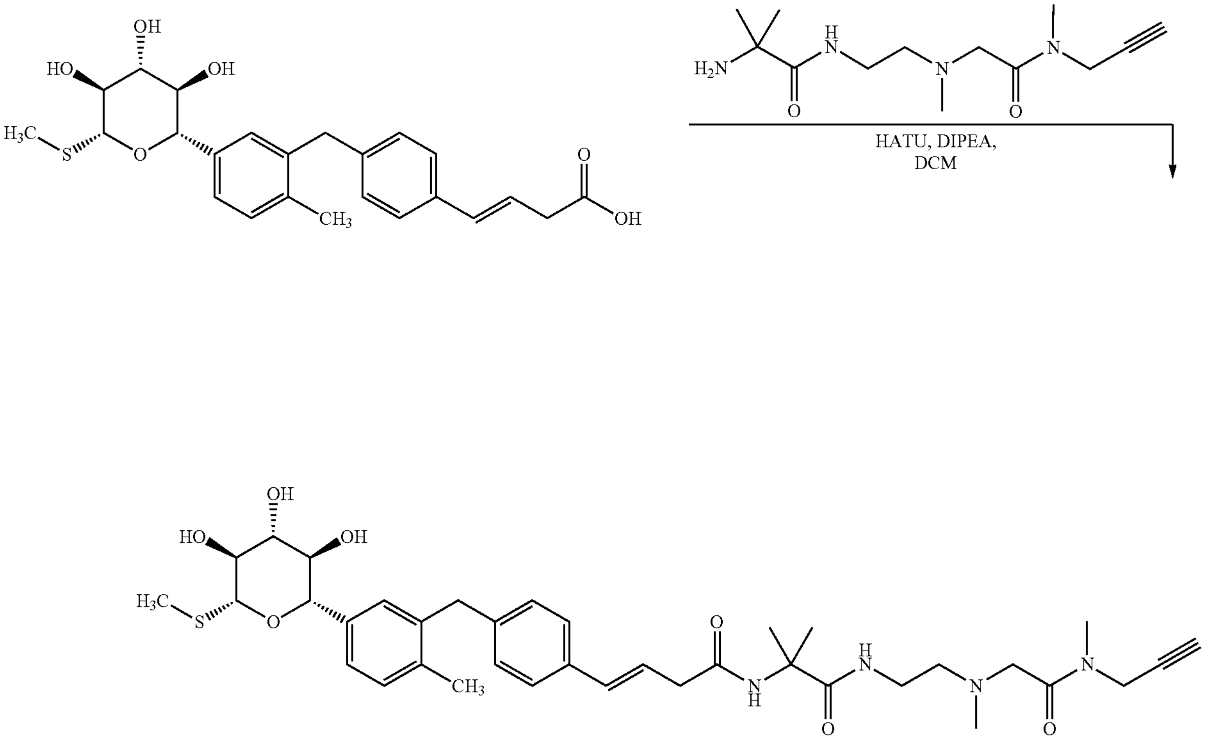

(E)-4-(4-(2-Methyl-5-((2S,3R,4R,5S,6R)-3,4,5-trihydroxy-6-(methylthio)tetrahydro-2H-pyran-2-yl)benzyl)phenyl)vinylacetic acid (70 mg), N,N-dimethylformamide (5 ml), N,N-diisopropylethylamine (45 mg), 2-(4-(2-amino-2-methylpropionyl)piperazin-1-yl)-N-methyl-N-(prop-2-yn-1-yl)acetamide (48 mg), and 2-(7-benzotriazole oxide)-N,N,N',N'-tetramethylurea hexafluorophosphate (70 mg) were added into a 25 ml reaction flask, and stirred at room temperature for 2 h after the addition. The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 38 mg of white solid.

Example 14

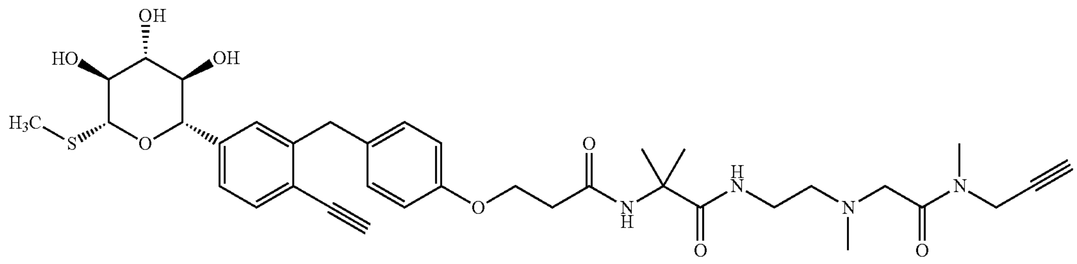 [SMILES: C#CCN(C)C(=O)CN(C)CCNC(=O)C(C)(C)NC(=O)CCOc1ccc(Cc2cc([C@@H]3O[C@H](SC)[C@@H](O)[C@H](O)[C@H]3O)ccc2C#C)cc1]

The compound was obtained by referring to the similar preparation scheme in Example 1. ESI-MS: 709.2 $[M+H]^+$.

The specific preparation method was as follows:

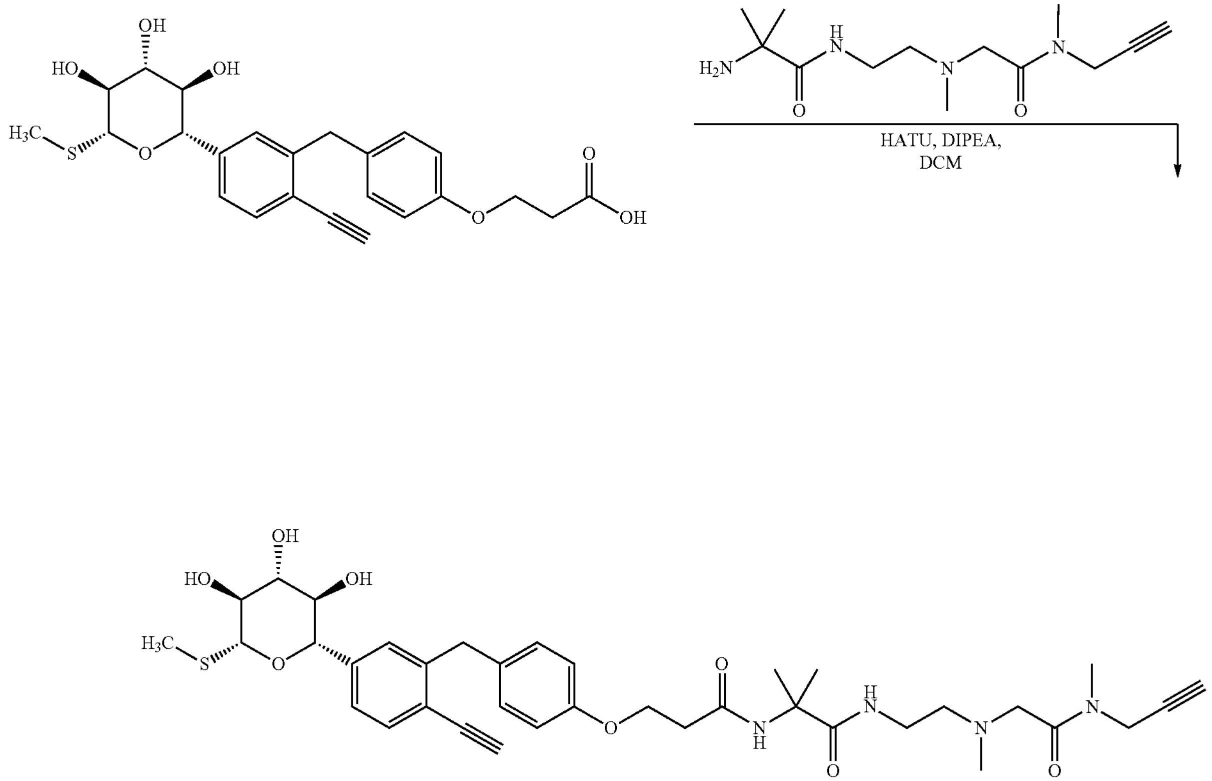

3-(4-(2-Ethynyl-5-((2S,3R,4R,5S,6R)-3,4,5-trihydroxy-6-(methylthio)tetrahydro-2H-pyran-2-yl)benzyl)phenyloxy) propionic acid (60 mg), N,N-dimethylformamide (5 ml), N,N-diisopropylethylamine (40 mg), 2-(4-(2-amino-2-methylpropionyl)piperazin-1-yl)-N-methyl-N-(prop-2-yn-1-yl) acetamide (40 mg), and 2-(7-benzotriazole oxide)-N,N,N',N'-tetramethylurea hexafluorophosphate (60 mg) were added into a 25 ml reaction flask, and stirred at room temperature for 2 h after the addition. The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 28 mg of pale yellow solid.

Example 15

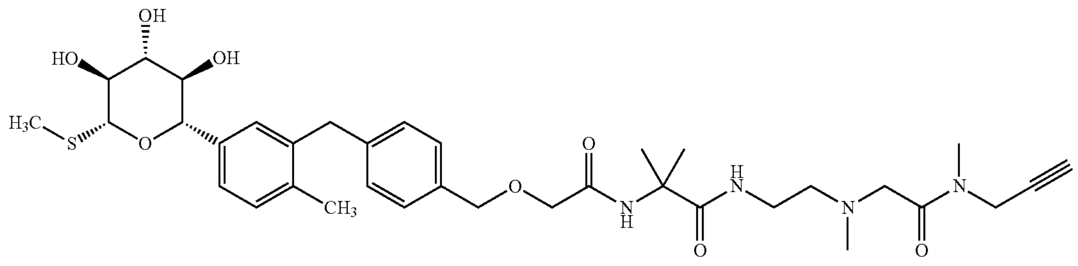 [SMILES: C#CCN(C)C(=O)CN(C)CCNC(=O)C(C)(C)NC(=O)COCc1ccc(Cc2cc([C@@H]3O[C@H](SC)[C@@H](O)[C@H](O)[C@H]3O)ccc2C)cc1]

The compound 6 was obtained by referring to the similar preparation scheme in Example 1. ESI-MS: 699.1 $[M+H]^+$.

The specific preparation method was as follows:

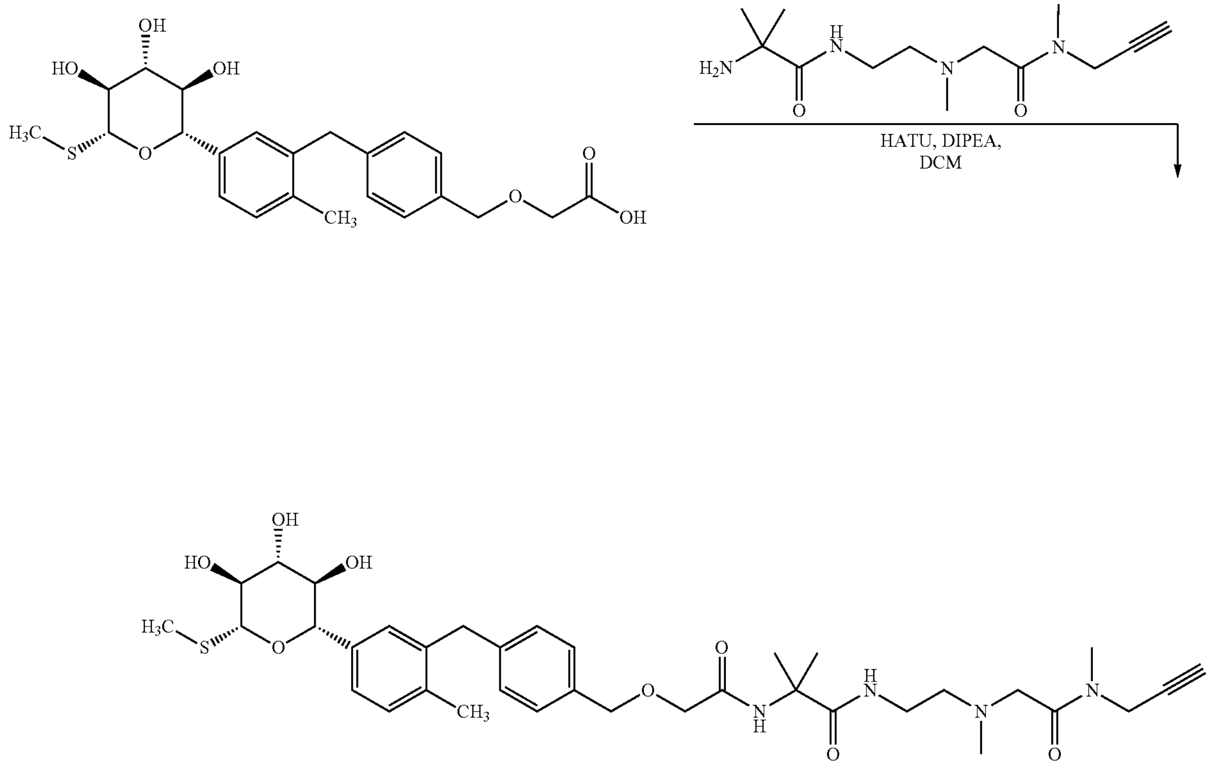

2-((4-(2-Methyl-5-((2S,3R,4R,5S,6R)-3,4,5-trihydroxy-6-(methylthio)tetrahydro-2H-pyran-2-yl) benzyl) benzyl) oxy)acetic acid (65 mg), N,N-dimethylformamide (5 ml), N,N-diisopropylethylamine (40 mg), 2-(4-(2-amino-2-methylpropionyl)piperazin-1-yl)-N-methyl-N-(prop-2-yn-1-yl) acetamide (42 mg), and 2-(7-benzotriazole oxide)-N,N,N',N'-tetramethylurea hexafluorophosphate (60 mg) were added into a 25 ml reaction flask, and stirred at room temperature for 2 h after addition. The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 29 mg of white solid.

Example 16

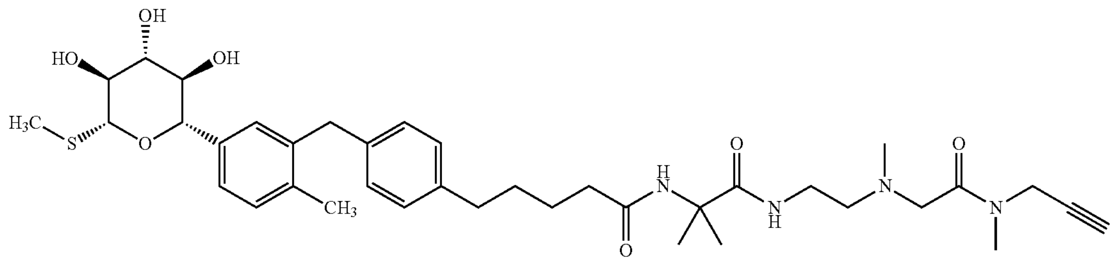 [SMILES: C#CCN(C)C(=O)CN(C)CCNC(=O)C(C)(C)NC(=O)CCCCc1ccc(Cc2cc([C@@H]3O[C@H](SC)[C@@H](O)[C@H](O)[C@H]3O)ccc2C)cc1]

The compound was obtained by referring to the similar preparation scheme in Example 1. ESI-MS: 711.2 $[M+H]^+$.

The specific preparation method was as follows:

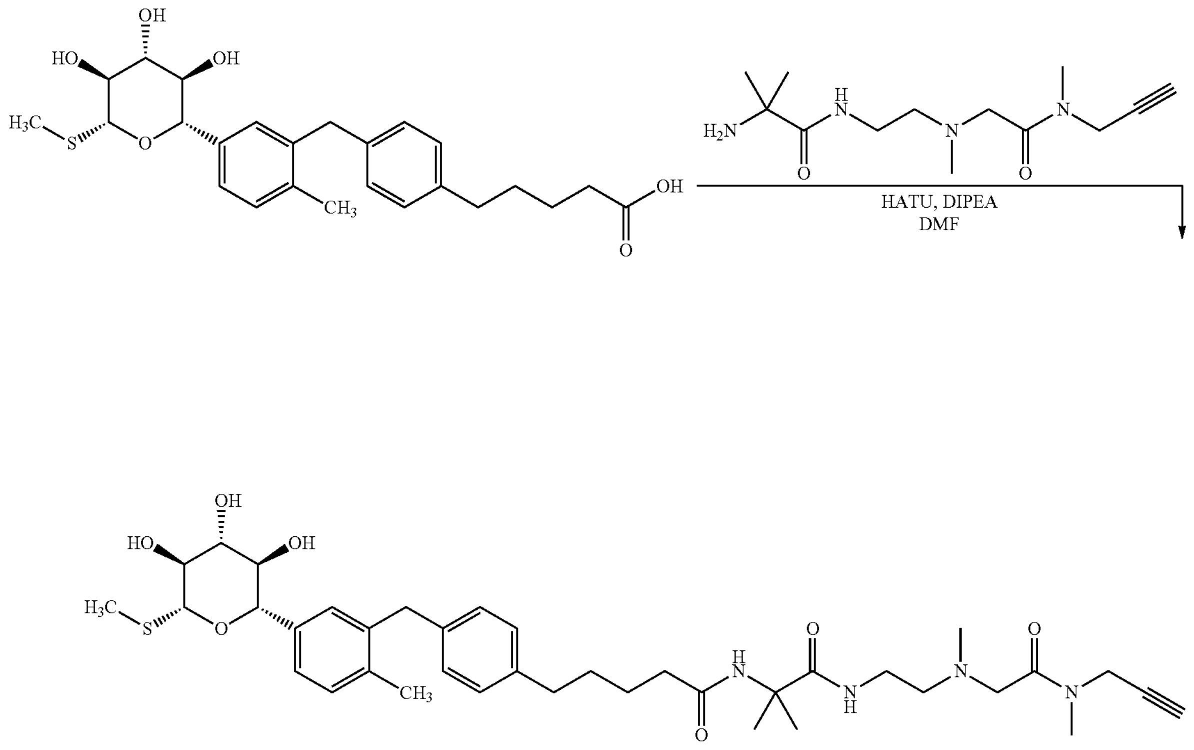

5-(4-(2-Methyl-5-((2S,3R,4R,5S,6R)-3,4,5-trihydroxy-6-(methylthio)tetrahydro-2H-pyran-2-yl)benzyl)pheny)valeric acid (70 mg), N,N-dimethylformamide (5 ml), N,N-diisopropylethylamine (40 mg), 2-(4-(2-amino-2-methylpropionyl)piperazin-1-yl)-N-methyl-N-(prop-2-yn-1-yl)acetamide (43 mg), and 2-(7-benzotriazole oxide)-N,N,N',N'-tetramethylurea hexafluorophosphate (60 mg) were added into a 25 ml reaction flask, and stirred at room temperature for 2 h after the addition. The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 36 mg of white solid.

Example 17

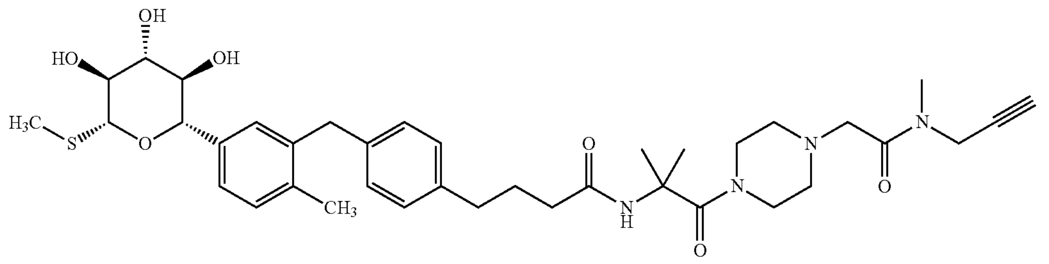 [SMILES: C#CCN(C)C(=O)CN1CCN(C(=O)C(C)(C)NC(=O)CCCc2ccc(Cc3cc([C@@H]4O[C@H](SC)[C@@H](O)[C@H](O)[C@H]4O)ccc3C)cc2)CC1]

The compound was obtained by referring to the similar preparation scheme in Example 1. ESI-MS: 709.5 $[M+H]^+$.

The specific preparation method was as follows:

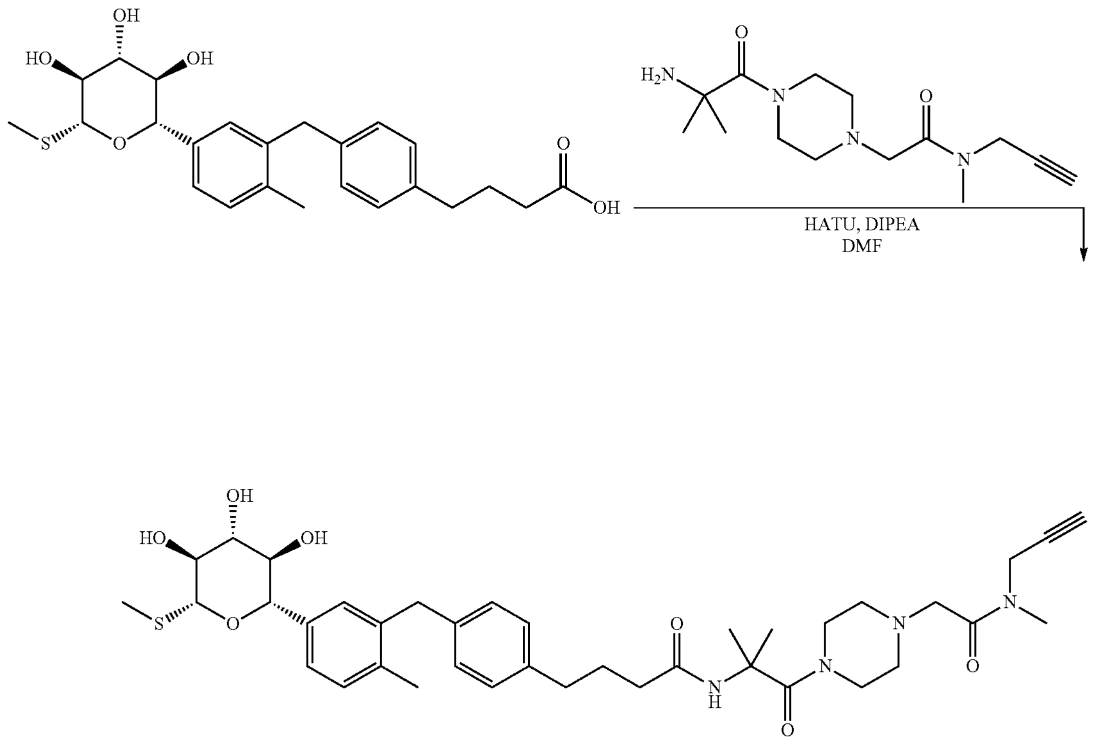

4-(4-(2-methyl-5-(2S,3R,4R,5S,6R)-3,4,5-trihydroxy-6-(methylthio)tetrahydro-2H-pyran-2-yl)benzyl)phenyl)butyric acid (89 mg), N,N-dimethylformamide (5 ml), N,N-diisopropylethylamine (52 mg), 2-(4-(2-amino-2-methylpropionyl)piperazin-1-yl)-N-methyl-N-(prop-2-yn-1-yl)acetamide (62 mg, 0.22 mmol), and 2-(7-benzotriazole oxide)-N,N,N',N'-tetramethylurea hexafluorophosphate (84 mg) were added into a 25 ml reaction flask, and stirred at room temperature for 2 h. The reaction solution was diluted with dichloromethane, and washed with water. The aqueous phase was extracted with dichloromethane for three times, and the organic phases were combined, washed with saturated salt solution, dried with anhydrous sodium sulfate, and filtered. The filtrate was concentrated to dryness, and purified by column chromatography to obtain 105 mg of white solid. $^1$H NMR (400 MHz, DMSO-d6): δ 8.07 (s, 1H), 7.13-7.05 (m, 7H), 5.20 (d, J=5.6 Hz, 1H), 5.10 (d, J=4.6 Hz, 1H), 4.85 (d, J=5.5 Hz, 1H), 4.33 (d, J=9.4 Hz, 1H), 4.29 (s, 1H), 4.12-4.08 (m, 2H), 4.06 (d, J=9.1 Hz, 1H), 3.91 (s, 2H), 3.49 (br s, 4H), 3.28-3.22 (m, 2H), 3.17-3.15 (m, 2H), 3.02 (s, 2H), 2.83 (s, 1H), 2.35-2.32 (m, 4H), 2.18 (s, 3H), 2.08-2.04 (m, 5H), 1.80-1.73 (m, 2H), 1.30 (s, 6H). $^{13}$C NMR (100 MHz, DMSO-d6): δ 171.1, 169.1, 169.0, 139.6, 138.9, 138.1, 137.8, 135.8, 130.1, 129.7, 129.0, 128.7, 126.0, 85.8, 81.8, 80.1, 78.6, 74.8, 74.4, 72.7, 55.9, 52.9, 49.1, 39.0, 38.8, 36.1, 35.0, 34.7, 34.4, 33.1, 27.3, 26.5, 19.5, 11.5. MS: m/z 709.3656, $[M+H]^+$.

Example 18

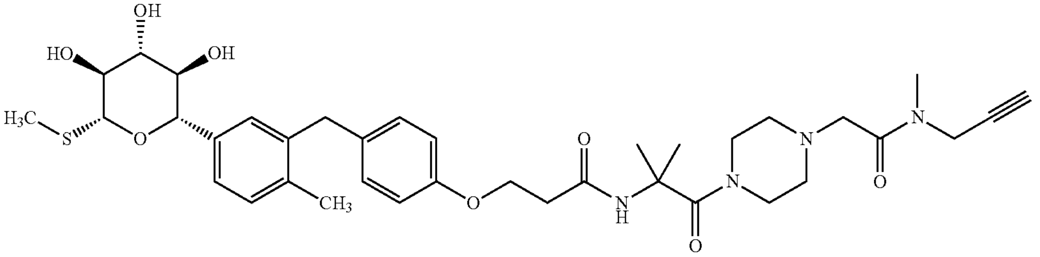 [SMILES: C#CCN(C)C(=O)CN1CCN(C(=O)C(C)(C)NC(=O)CCOc2ccc(Cc3cc([C@@H]4O[C@H](SC)[C@@H](O)[C@H](O)[C@H]4O)ccc3C)cc2)CC1]

The compound was obtained by referring to the similar preparation scheme in Example 1. ESI-MS: 711.3 $[M+H]^+$.

The specific preparation method was as follows:

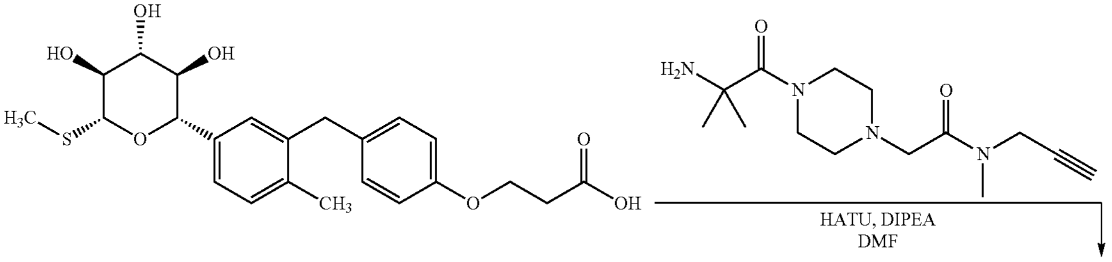

-continued

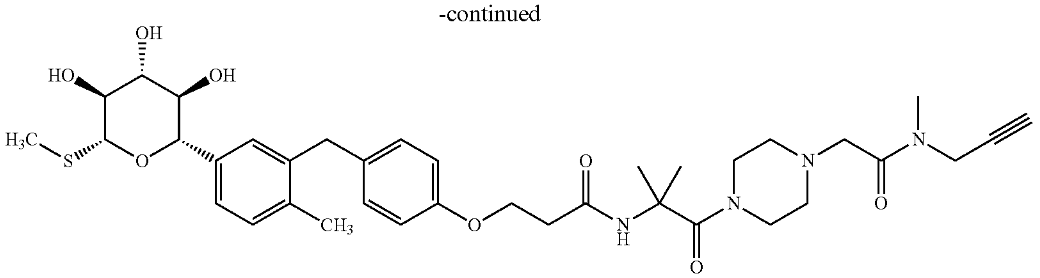

3-(4-(2-Methyl-5-((2S,3R,4R,5S,6R)-3,4,5-trihydroxy-6-(methylthio)tetrahydro-2H-pyran-2-yl)benzyl)phenyloxy) propionic acid (50 mg), N,N-dimethylformamide (5 ml), N,N-diisopropylethylamine (30 mg), 2-(4-(2-amino-2-methylpropionyl)piperazin-1-yl)-N-methyl-N-(prop-2-yn-1-yl) acetamide (40 mg), and 2-(7-benzotriazole oxide)-N,N,N',N'-tetramethylurea hexafluorophosphate (50 mg) were added into a 25 ml reaction flask, and stirred at room temperature for 2 h. The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 51 mg of white solid.

Example 19

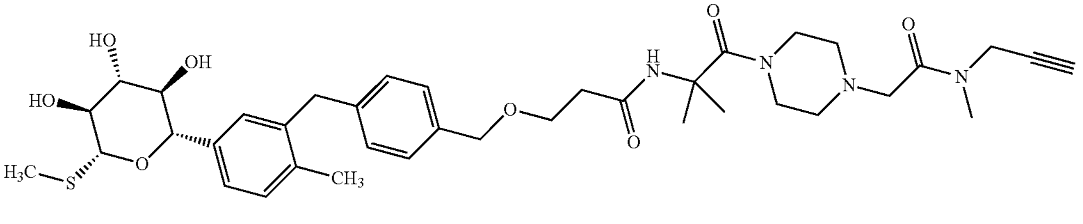 [SMILES: C#CCN(C)C(=O)CN1CCN(C(=O)C(C)(C)NC(=O)CCOCc2ccc(Cc3cc([C@@H]4O[C@H](SC)[C@@H](O)[C@H](O)[C@H]4O)ccc3C)cc2)CC1]

The compound was obtained by referring to the similar preparation scheme in Example 1. ESI-MS: 725.1 $[M+H]^+$.

The specific preparation method was as follows:

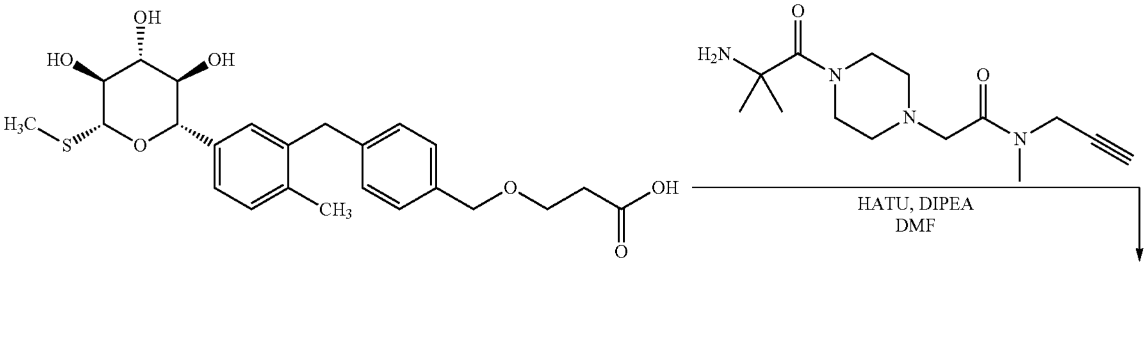

-continued

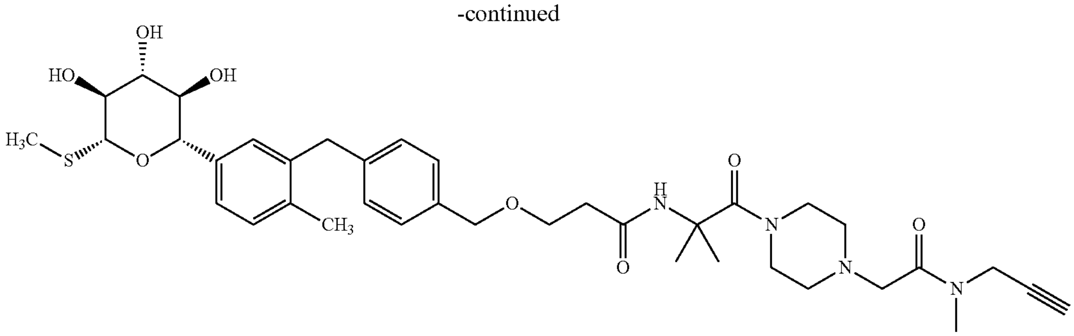

3-((4-(2-methyl-5-((2S,3R,4R,5S,6R)-3,4,5-trihydroxy-6-(methylthio)tetrahydro-2H-pyran-2-yl)benzyl)benzyl)oxy)propionic acid (55 mg), N,N-dimethylformamide (5 ml), N,N-diisopropylethylamine (30 mg), 2-(4-(2-amino-2-methylpropionyl)piperazin-1-yl)-N-methyl-N-(prop-2-yn-1-yl)acetamide (40 mg), and 2-(7-benzotriazole oxide)-N,N,N',N'-tetramethylurea hexafluorophosphate (55 mg) were added into a 25 ml reaction flask, and stirred at room temperature for 2 h. The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 54 mg of white solid.

Example 20

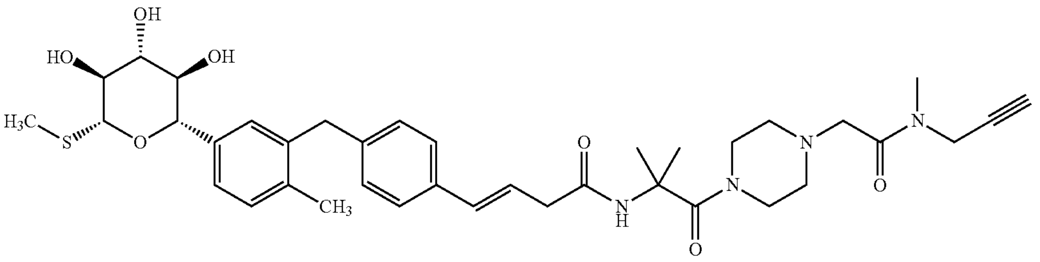 [SMILES: C#CCN(C)C(=O)CN1CCN(C(=O)C(C)(C)NC(=O)C/C=C/c2ccc(Cc3cc([C@@H]4O[C@H](SC)[C@@H](O)[C@H](O)[C@H]4O)ccc3C)cc2)CC1]

The compound was obtained by referring to the similar preparation scheme in Example 1. ESI-MS: 707.5 $[M+H]^+$.

The specific preparation method was as follows:

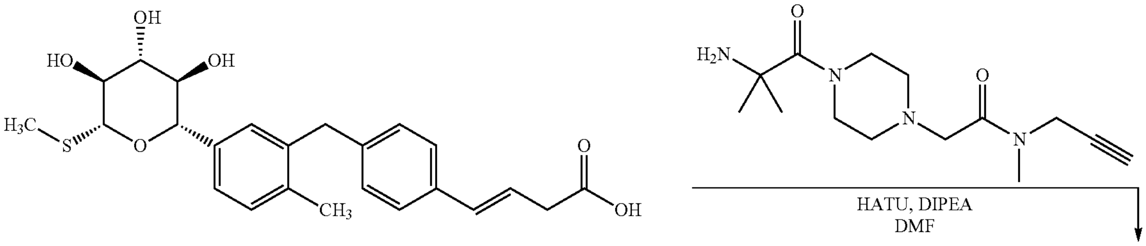

-continued

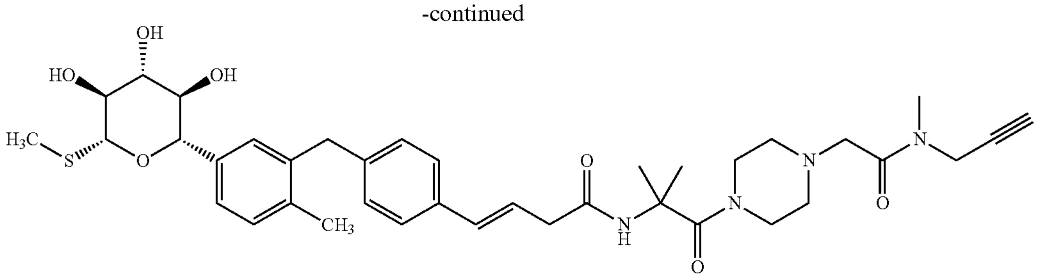

(E)-4-(4-(2-Methyl-5-((2S,3R,4R,5S,6R)-3,4,5-trihydroxy-6-(methylthio)tetrahydro-2H-pyran-2-yl)benzyl)phenyl)vinylacetic acid (65 mg), N,N-dimethylformamide (5 ml), N,N-diisopropylethylamine (41 mg), 2-(4-(2-amino-2-methylpropionyl)piperazin-1-yl)-N-methyl-N-(prop-2-yn-1-yl)acetamide (45 mg), and 2-(7-benzotriazole oxide)-N,N,N',N'-tetramethylurea hexafluorophosphate (65 mg) were added into a 25 ml reaction flask, and stirred at room temperature for 2 h. The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 63 mg of white solid.

Example 21

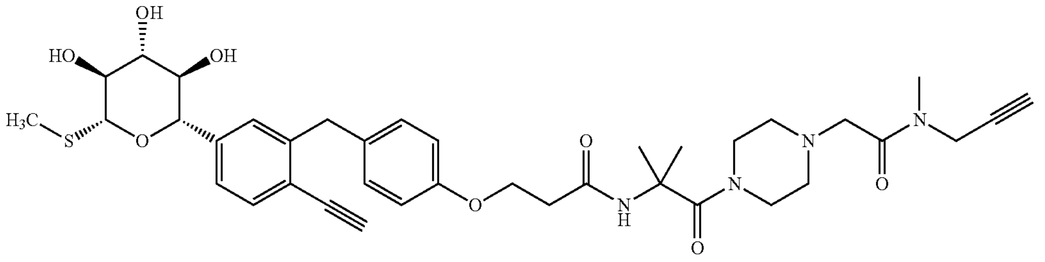 [SMILES: C#CCN(C)C(=O)CN1CCN(C(=O)C(C)(C)NC(=O)CCOc2ccc(Cc3cc([C@@H]4O[C@H](SC)[C@@H](O)[C@H](O)[C@H]4O)ccc3C#C)cc2)CC1]

The compound was obtained by referring to the similar preparation scheme in Example 1. ESI-MS: 721.4 $[M+H]^+$.

The specific preparation method was as follows:

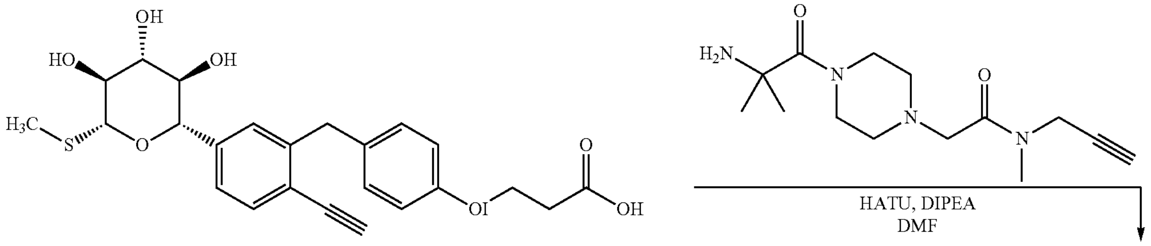

-continued

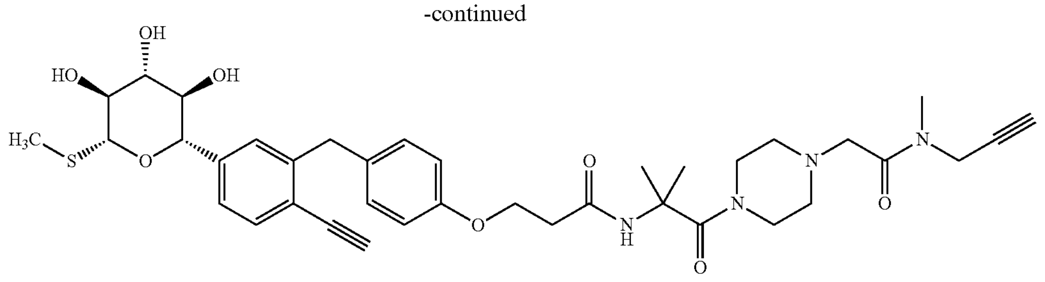

3-(4-(2-Ethynyl-5-((2S,3R,4R,5S,6R)-3,4,5-trihydroxy-6-(methylthio)tetrahydro-2H-pyran-2-yl)benzyl)phenyloxy) propionic acid (70 mg), N,N-dimethylformamide (5 ml), N,N-diisopropylethylamine (41 mg), 2-(4-(2-amino-2-methylpropionyl)piperazin-1-yl)-N-methyl-N-(prop-2-yn-1-yl) acetamide (45 mg), and 2-(7-benzotriazole oxide)-N,N,N',N'-tetramethylurea hexafluorophosphate (65 mg) were added into a 25 ml reaction flask, and stirred at room temperature for 2 h. The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 81 mg of white solid.

Example 22

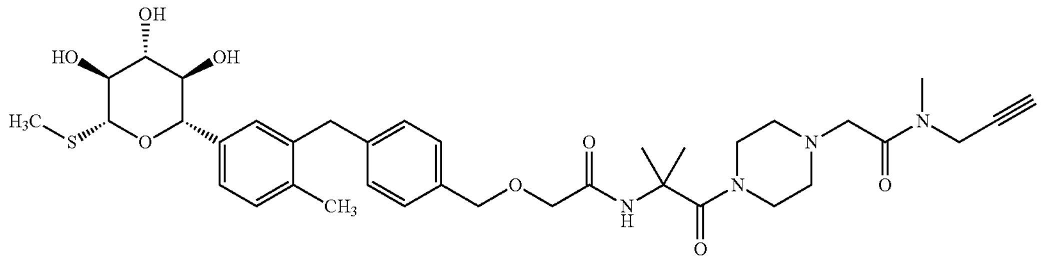 [SMILES: C#CCN(C)C(=O)CN1CCN(C(=O)C(C)(C)NC(=O)COCc2ccc(Cc3cc([C@@H]4O[C@H](SC)[C@@H](O)[C@H](O)[C@H]4O)ccc3C)cc2)CC1]

The compound was obtained by referring to the similar preparation scheme in Example 1. ESI-MS: 711.1 $[M+H]^+$.

The specific preparation method was as follows:

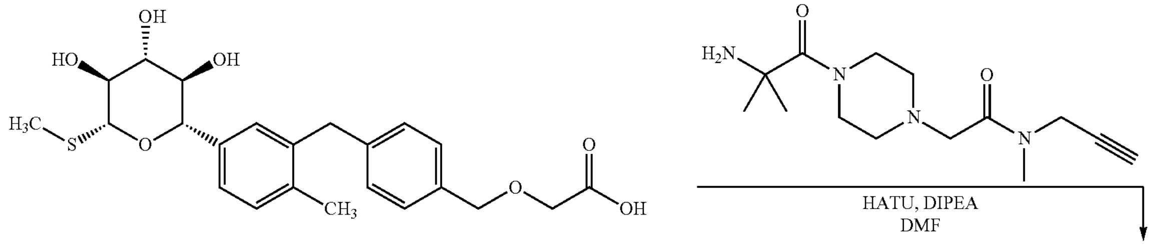

-continued

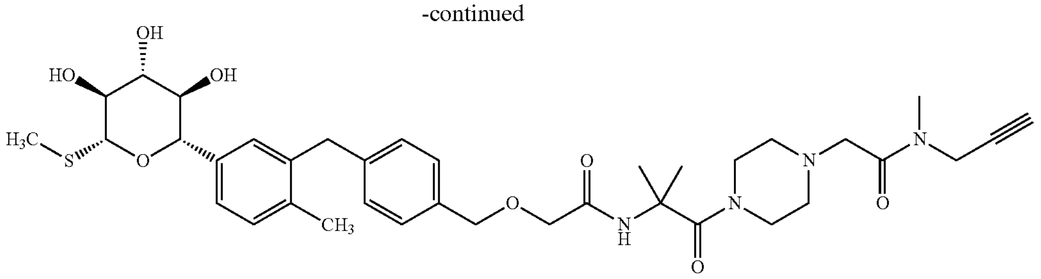

2-((4-(2-Methyl-5-((2S,3R,4R,5S,6R)-3,4,5-trihydroxy-6-(methylthio)tetrahydro-2H-pyran-2-yl) benzyl) benzyl) oxy)acetic acid (65 mg), N,N-dimethylformamide (5 ml), N,N-diisopropylethylamine (40 mg), 2-(4-(2-amino-2-methylpropionyl)piperazin-1-yl)-N-methyl-N-(prop-2-yn-1-yl) acetamide (45 mg), and 2-(7-benzotriazole oxide)-N,N,N',N'-tetramethylurea hexafluorophosphate (65 mg) were added into a 25 ml reaction flask, and stirred at room temperature for 2 h. <0 The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 73 mg of white solid.

Example 23

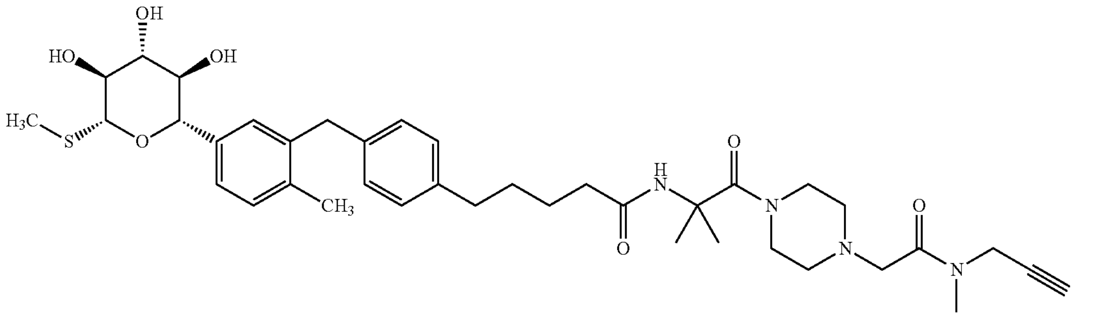 [SMILES: C#CCN(C)C(=O)CN1CCN(C(=O)C(C)(C)NC(=O)CCCCc2ccc(Cc3cc([C@@H]4O[C@H](SC)[C@@H](O)[C@H](O)[C@H]4O)ccc3C)cc2)CC1]

The compound was obtained by referring to the similar preparation scheme in Example 1. ESI-MS: 723.3 $[M+H]^+$.

The specific preparation method was as follows:

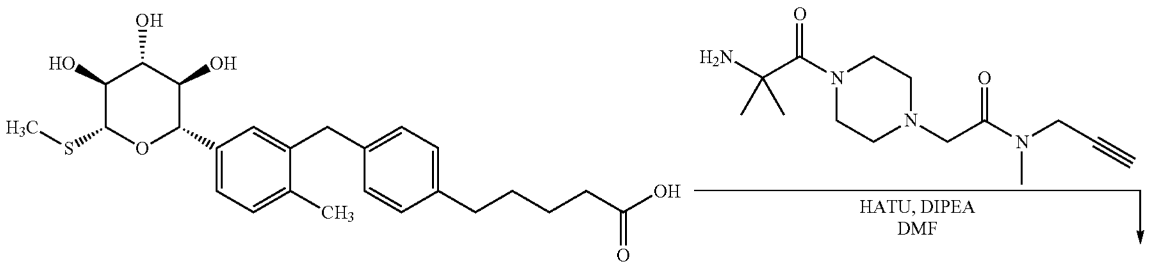

-continued

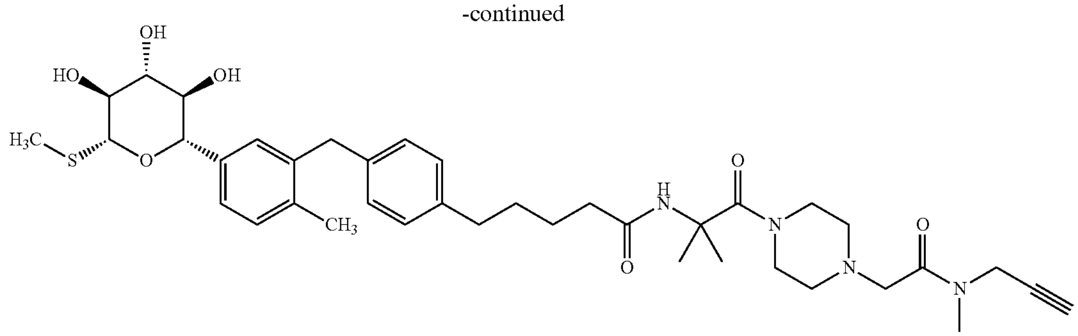

5-(4-(2-Methyl-5-((2S,3R,4R,5S,6R)-3,4,5-trihydroxy-6-(methylthio)tetrahydro-2H-pyran-2-yl)benzyl)pheny)valeric acid (60 mg), N,N-dimethylformamide (5 ml), N,N-diisopropylethylamine (35 mg), 2-(4-(2-amino-2-methylpropionyl)piperazin-1-yl)-N-methyl-N-(prop-2-yn-1-yl)acetamide (42 mg), and 2-(7-benzotriazole oxide)-N,N,N',N'-tetramethylurea hexafluorophosphate (57 mg) were successively added into a 25 ml reaction flask, and stirred at room temperature for 2 h. The reaction solution was diluted with dichloromethane, and washed with water. The aqueous phase was extracted with dichloromethane for three times, and the organic phases were combined, washed once with saturated salt solution, dried with anhydrous sodium sulfate, and filtered. The filtrate was concentrated to dryness, and purified by column chromatography to obtain 58 mg of white solid.

The introduction of an "alkyne" functional group into some compounds of the present invention has two advantages:

on one hand, the "alkynyl" functional group can use "Click chemistry" to connect bioluminescent markers, which is beneficial to accurately determine the distribution of the compound in the body. For example, "click chemistry" occurs between the compounds of present invention and "azide" compounds with fluorescent chromophores, under the catalysis of copper salts, to generate fluorescent compounds with "triazole structure". The compounds of the present invention can also be linked with other biological compounds with biomarker functions to form new chemical substances that are easy to detect, which is of great significance to fully study the effectiveness and safety of such compounds.

On the other hand, the "alkynyl" functional group connects with other pharmacophore groups through "Click chemistry", which is conducive to finding candidate compounds with better comprehensive properties. Examples were as follows:

Exploratory Research Using "Click Chemistry":

(1) Preparation of Labeled Compounds with Luminescent Properties

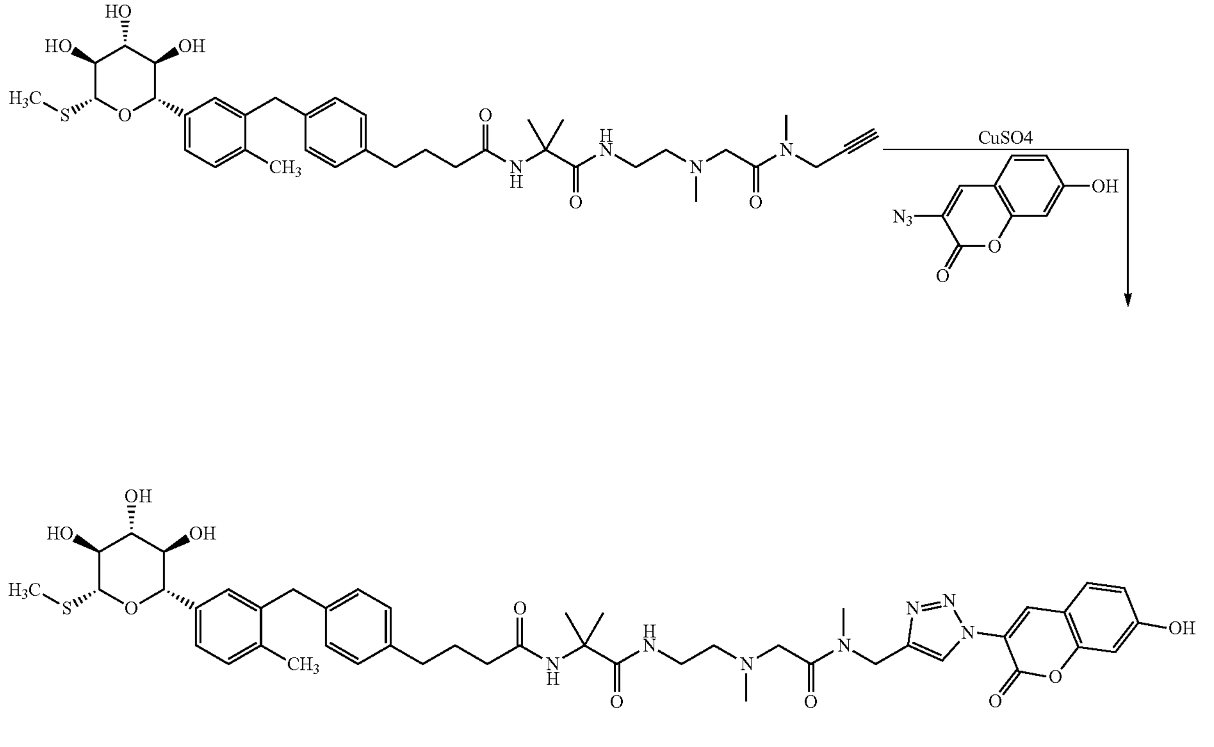

The compound of Example 10, copper sulfate, and 7-hydroxy-3-azidocoumarin (refer to Journal of the American Chemical Society (2014), 136(20), 7205-7208; Chemistry—A European Journal (2011), 17(12), 3326-3331, S3326/1-S3326/21; Journal of Fluorescence (2013), 23(1), 181-186; Journal of Organic Chemistry (2011), 76(12), 4964-4972; Angewandte Chemie, International Edition (2019), 58(21), 6987-6992) were stirred and reacted at room temperature to obtain a product. Rf: 0.10 (dichloromethane: methanol=10:1).

(2) Preparation of Candidate Compounds with Better Comprehensive Properties

In the mouse glucose tolerance test, the compounds of the present invention have the effect of improving the blood glucose level of the test animals.

The compounds of the present invention help to reduce body weight, and in in vivo pharmacodynamic studies, the compounds of the present invention reduced the body weight of experimental animals.

The compounds of the present invention have very low or no absorption in vivo, and pharmacokinetic studies have shown that the compounds of the present invention are hardly detected in experimental animals, and have almost no side effects on other organs in the body.

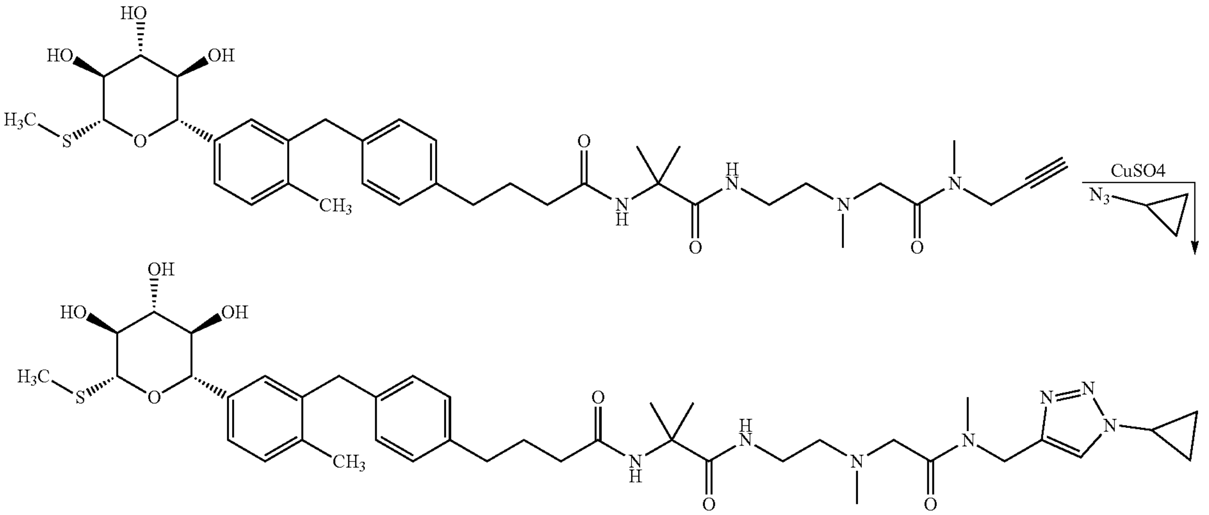

The compound of Example 10, copper sulfate, and a cyclopropyl azide compound (refer to Chemische Berichte (1985), 118(4), 1564-1574; Science of Synthesis (2010), 41, 543-612; Nature (London, United Kingdom) (2019), 574 (7776), 86-89) were stirred and reacted at room temperature, and after the reaction was completed, target compounds could be prepared by silica gel column chromatography. Rf: 0.12 (dichloromethane:methanol=10:1). The compound has similar biological activity to that of Example 10, and has better lipid solubility and water solubility than the compound of Example 5.

Biological Test

1. SGLT1 Inhibitor Activity Experiment 1

The inhibitory activity of SGLT1 was tested with reference to the method described in document (Journal of Medicinal Chemistry 2017, 60, 710-721, Discovery of LX2761, a Sodium-Dependent Glucose Cotransporter 1 (SGLT1) Inhibitor Restricted to the Intestinal Lumen, for the Treatment of Diabetes).

Test Results:

| Compound Number | SGLT1 Activity |
|---|---|
| 1 (Example 10) | A |
| 2 (Example 11) | A |
| 3 (Example 12) | A |
| 4 (Example 17) | A |

The experimental results show that the compounds of the present invention have significant activity of inhibiting SGLT1.

2. hSGLT1 Inhibitor Activity Experiment 2

Inhibitory activity testing was performed with reference to a similar method described in document [Acta Pharmaceutica *Sinica* 2017, 52 (6): 897-903; Nature Protocols (2007), 2(3), 753-762; Journal of Biochemical and Biophysical Methods (2005), 64(3), 207-215; Diabetes Technology & Therapeutics (2011), 13(7), 743-775].

In this experiment, the in vitro activity assay was evaluated using the uptake of 2-NBDG (2-Deoxy-2-[(7-nitro-2,1,3-benzoxadiazol-4-yl)amino]-D-glucose, CAS NO: 186689-07-6) by human embryonic kidney epithelial cells (HEK293, stably expressing human SGLT1), and the SGLT1 inhibitory activity of the target compound was determined by measuring its half-maximal inhibitory concentration ($IC_{50}$).

HEK293 cells that can stably express human SGLT1 gene were inoculated into a 96-well clear-bottom black plate containing DMEM medium. The cells were incubated at 37° C., 5% $CO_2$ in a cell incubator. The medium in the 96-well plate was aspirated, and the plate was treated with low-glucose serum-free DMEM medium, and washed once with non-specific uptake buffer and once with $Na^+$-dependent uptake buffer. Uptake buffer containing test compound was added to each well of cells, followed by uptake buffer containing 2-NBDG for glucose uptake, and the cell plate was incubated at 37° C., 5% $CO_2$. The compounds were gradiently diluted. The uptake reaction was stopped by removing the culture medium, and after washing the cells with ice-cold uptake buffer, the washing solution was removed. The cells were lysed by adding NaOH, and the content of 2-NBDG in the cells was detected by a fluorescence microplate reader. The protein concentration of the lysate was measured by BCA method, the uptake of 2-NBDG was quantified by fluorescence intensity/protein content, and the obtained data were analyzed using GraphPad Prism to determine the median inhibitory concentration ($IC_{50}$) of the compound to be tested.

The comparative compound 18 is the compound numbered "18" in the document (Journal of Medicinal Chemistry 2017, 60, 710-721, Discovery of LX2761, a Sodium-Dependent Glucose Cotransporter 1 (SGLT1) Inhibitor Restricted to the Intestinal Lumen, for the Treatment of Diabetes). It was prepared and identified according to the synthetic method described in the document.

Test Results:

| Compound Number | SGLT1 Inhibitory Activity (nM) |
|---|---|
| Example 1 | 0.78 |
| Example 2 | 1.12 |
| Example 3 | 0.93 |
| Example 4 | 0.87 |
| Example 9 | 0.53 |
| Example 10 | 0.37 |
| Example 17 | 0.49 |
| Comparative compound 18 | 8.16 |

The experimental results show that the compounds of the examples of the present invention, for example, Example 1, Example 2, Example 3, Example 4, Example 9, Example 10, and Example 17, have significant activity of inhibiting SGLT1.

3. Oral Glucose Tolerance Test (OGTT) after Continuous Administration in Rats for 14 Days Experimental animals: SPF male SD rats;

Compound preparation: an appropriate amount of the compounds of Example 1, Example 2, Example 9, Example 10, and Example 17 were weighed, and uniformly suspended with an appropriate amount of 0.5% CMC-Na solution;

Preparation of glucose solution: an appropriate amount of glucose powder was weighed and dissolved with an appropriate amount of pure water;

Dosage and method of administration: 0.009 mg/kg, oral gavage.

Experimental process: the animals were fed a normal diet with consecutive administration for 14 days, and the glucose tolerance test was performed on day 15, blood glucose was detected before administration (−30 min), before giving glucose (0 min), and 10, 30, 60, and 120 min after giving glucose solution, and the defecation of animals was observed.

Experimental results: The results in FIG. 1, FIG. 2, FIG. 3, FIG. 4 and FIG. 5 show that the compounds of Example 1, Example 2, Example 9, Example 10, and Example 17 can significantly reduce the blood sugar level of rats, and no loose stools were observed in the experimental animals within 48 hours before and after the experiment.

4. Oral Glucose Tolerance Test (OGTT) after Consecutive Administration in Mice

Experimental animals: SPF male SD mice;

Compound preparation: an appropriate amount of the compound of Example 10 was weighed, and uniformly suspended with an appropriate amount of 0.5% CMC-Na solution;

Preparation of glucose solution: an appropriate amount of glucose powder was weighed and dissolved with an appropriate amount of pure water;

Administration and dosage: oral gavage; blank vehicle group, high-dose group (1.5 mg/kg), low-dose group (0.1 mg/kg).

Experimental Process:

(1) The mice were fed a high-sugar diet for 6 days, and then grouped (10 mice in each group) to enter the administration stage;

(2) Example compound 10 was administered at 5:00 pm every day from day 1 to day 5, once a day, and then the animals were fed a high-sugar free diet, and the defecation of the animals was observed.

(3) On day 6, oral glucose tolerance test was performed, and glucose solution (2 g/kg) was orally administered. Blood glucose was detected before (0 min) and 10, 30, and 60 min after giving glucose solution, respectively.

Experimental Results:

(1) From day 1 to day 5, the observation of animal defecation after continuous administration is summarized as follows:

| Statistics of loose stools in animals | Day 1 | Day 2 | Day 3 | Day 4 | Day 5 |
|---|---|---|---|---|---|
| High-dose group (1.5 mg/kg) | 1/10 | 0/10 | 0/10 | 0/10 | 0/10 |
| Low-dose group (0.1 mg/kg) | 0/10 | 0/10 | 0/10 | 0/10 | 0/10 |

Figure 6:
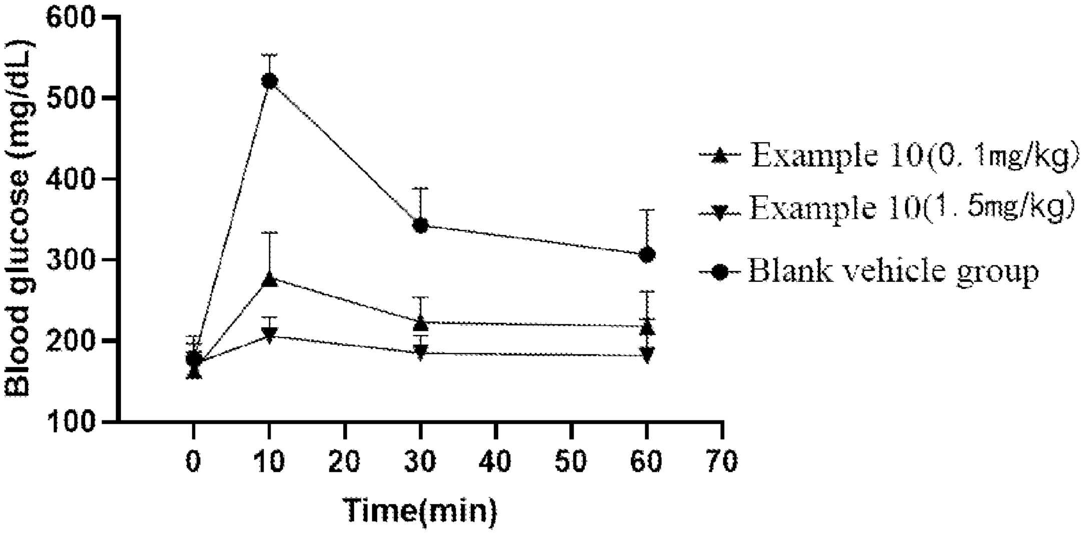
FIG. 6 shows results of oral glucose tolerance test (OGTT) on day 6 after 5 days of continuous administration in mice.

(2) The results of oral glucose tolerance test (OGTT) on day 6 are shown in FIG. 6.

Experimental summary: (1) From day 1 to day 5, the example compound 10 was continuously administered, in the high-dose group (1.5 mg/kg), only one animal had loose stools on day 1, and the animals did not have loose stools on day 2 to day 5; in the low-dose group (0.1 mg/kg), the animals did not have loose stools after continuous administration for 5 days.

(2) On day 6, in the oral glucose tolerance test (OGTT), the results in FIG. 6 show that both the high and low dose groups of the compound of Example 10 can significantly reduce the blood glucose level of mice.

5. Pharmacokinetic Study in Rats

Experimental animals: SPF male SD rats;

Dosage and method of administration: 10 mg/kg, oral gavage.

Research compound: Dapagliflozin, the compound of Example 9, the compound of Example 10, the compound of Example 17, and the comparative compound 6;

Test method: Before administration (0), and 1, 4, 8, and 24 hours after administration, 0.2 ml of blood was collected from orbital venous plexus, anticoagulated with heparin, plasma was collected, and the blood drug concentration was determined.

Note: The comparative compound 6 is the compound numbered "6" in the document (Journal of Medicinal Chemistry 2017, 60, 710-721, Discovery of LX2761, a Sodium-Dependent Glucose Cotransporter 1 (SGLT1) Inhibitor Restricted to the Intestinal Lumen, for the Treatment of Diabetes). It was prepared and identified according to the synthetic method described in the document.

Pharmacokinetic Absolute Bioavailability Data of Rats:

| Compound | Absolute Bioavailability (F %) |
|---|---|
| Example 9 | N/A |
| Example 10 | N/A |
| Example 17 | N/A |
| Dapagliflozin | 73% |
| Comparative compound 6 | 23% |

Figure 7:
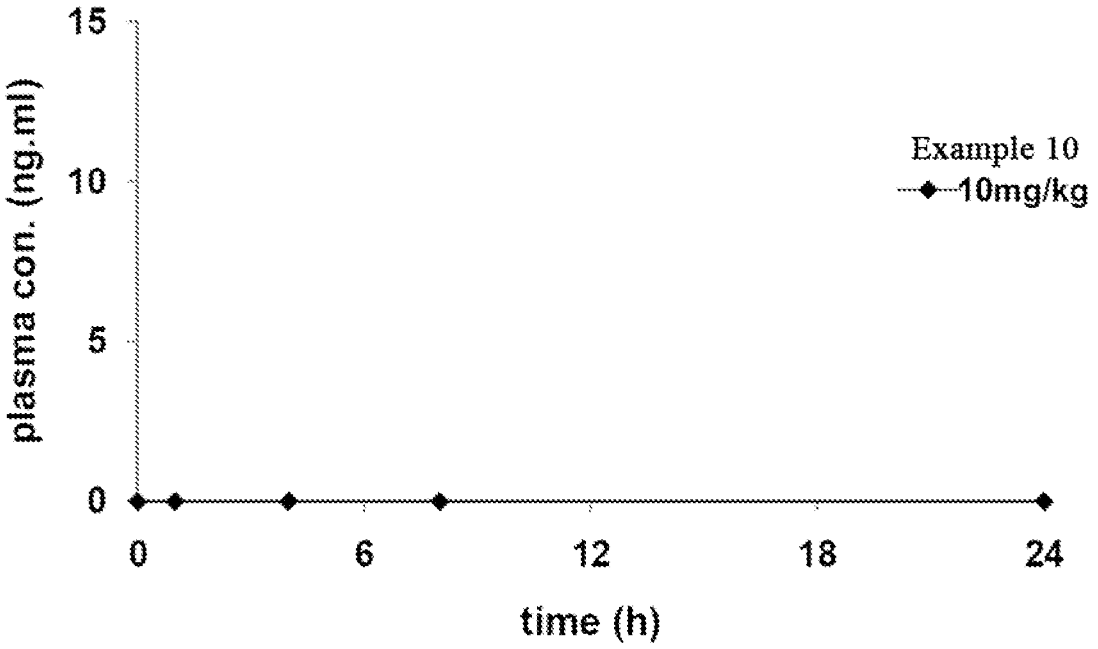
FIG. 7 shows plasma drug concentration-time curve in rats.

The experimental results show that: when the compounds of Example 9, Example 10 and Example 17 were subjected to in vivo detection, the drug concentration in plasma did not reach the detection limit, so that it was impossible to quantitatively detect the amounts of the compounds of Example 9, Example 10 and Example 17 entering the body (as shown in FIG. 7), indicating that the compounds of Example 9, Example 10 and Example 17 almost no absorption; while the absolute bioavailability of the comparative compound 6 was 23%, and the absolute bioavailability of dapagliflozin was 73%. Therefore, the comparative compound 6 and dapagliflozin were both absorbed into the blood after oral administration, and their exposure to organs in the body (e.g., brain, heart and other organs) may lead to potential and unpredictable toxicity.

In addition to being expressed in the kidney, SGLT1 also exists in intestinal epithelial cells and organs such as the heart and the brain. Compared with the comparative compound 6 and dapagliflozin, the compounds of Example 9, Example 10 and Example 17 of the present invention were hardly detected in vivo after oral administration. Therefore, according to preliminary experimental evidence, it is inferred that the compounds of Example 9, Example 10 and Example 17 of the present invention have no side effects on various organs such as the heart and brain.

6. In Vivo Hypoglycemic Efficacy Experiment Combined with Sitagliptin

Model establishment: SPF grade Balb/C male mice were used in this experiment, and the establishment of the type 2 diabetes mouse model was induced by intraperitoneal injection of streptozotocin (STZ) supplemented by high-fat and high-sugar diet.

Group: 10 per group

Administration: normal group, model group, low-dose combined administration group (0.01 mg/kg of the compound of Example 10+20 mg/kg of sitagliptin), medium-dose combined administration group (0.05 mg/kg of the compound of Example 10+20 mg/kg of sitagliptin), high-dose combined administration group (0.1 mg/kg of the compound of Example 10+20 mg/kg of sitagliptin), sitagliptin group (20 mg/kg). The normal group and the model group were given the solvent by gavage.

The experimental results show that the combination of the compound of Example 10 and sitagliptin can significantly reduce the blood glucose level of diabetic model animals, and there is a dose-effect relationship.

7. Study on Intestinal Microbial Metabolic Stability of the Compounds

Methods: The collected rat feces were processed, and the feces suspension was obtained for the determination of metabolic stability. The mixed reaction system consisting of the rat feces suspension and the compound of Example 5 was incubated at 37° C. for 3 h, 6 h, 12 h and 24 h. The compound of Example 10 in the incubation system was analyzed to determine the total amount of remaining compound. Wherein, "+" represents the remaining percentage being: <50%; "++" represents the remaining percentage being: 50% to 70%; "+++" represents the remaining percentage being: 70% to 90%; "++++" means the remaining percentage being: >90%.

Experimental Results:

| Incubation time | 3 h | 6 h | 12 h | 24 h |
|---|---|---|---|---|
| Percentage of remaining compound of Example 10 | ++++ | +++ | +++ | +++ |

The test results showed that after the compound of Example 10 was incubated with microorganisms in rat feces for about 24 hours, the remaining compound of Example 10 was still relatively abundant (>70%). It was illustrated that the compound of Example 10 could still maintain high stability under the metabolism of intestinal microorganisms.

8. The Compound of the Present Invention has Anti-Tumor Effect.

In the anti-tumor experiment of Hep3B xenograft tumor model, it is found that the compound of the present invention can inhibit the growth of tumor; the test on the animal model induced by high-fat diet suggests that the compounds of the present invention are beneficial to the remission of non-alcoholic fatty liver disease and non-alcoholic steatohepatitis, as well as the treatment of liver and kidney diseases related to energy absorption and metabolism.

The invention claimed is:

1. A compound of formula (XA-1), or a stereoisomer, tautomer or pharmaceutically acceptable salt thereof, (XA-1)

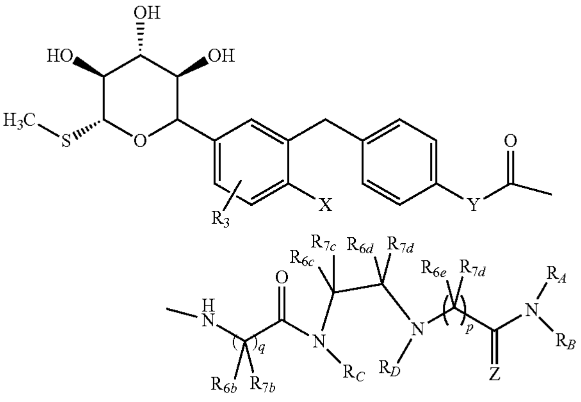

wherein, X, $R_C$ and $R_D$ are each independently hydrogen, deuterium, halogen, C1-C6 alkyl, C3-C6 cycloalkyl, C2-C6 alkenyl, or C2-C6 alkynyl;

$R_{6b}$, $R_{7b}$, $R_{6c}$, $R_{7c}$, $R_{6d}$, $R_{7d}$, $R_{6e}$ and $R_{7e}$ are each independently hydrogen, deuterium, halogen, C1-C6 alkyl or acyl; or $R_{6b}$ and $R_{7b}$, $R_{6c}$ and $R_{7c}$, $R_{6a}$ and $R_{7d}$, or $R_{6e}$ and $R_{7e}$ together with the carbon atoms attached therewith form a 3- to 8-membered carbocycle optionally substituted by hydrogen, halogen, C1-C6 alkyl, or halogenated C1-C6 alkyl;

$R_A$ and $R_B$ are each independently hydrogen, deuterium, alkyl, deuterated alkyl, haloalkyl, alkoxy, haloalkoxy, halogen, amino, mercapto, nitro, hydroxyl, cyano, oxo, C2-C8 alkenyl, C2-C8 alkynyl, cycloalkyl, heterocyclyl, aryl, heteroaryl, $-(CH_2)_{n1}R_{aa}$, $-(CH_2)_{n1}OR_{aa}$, $-SR_{aa}$, $-(CH_2)_{n1}C(O)R_{aa}$, $-SR_{aa}$, $-C(O)OR_{aa}$, —C(O)$R_{aa}$, —S(O)$_{m1}R_{aa}$, —$(CH_2)_{n1}$S(O)$_{m1}R_{aa}$, —N$R_{aa}R_{bb}$, —C(O)N$R_{aa}R_{bb}$, —N$R_{aa}$C(O)$R_{bb}$, or N$R_{aa}$S(O)$_{m1}R_{bb}$;

$R_{aa}$ and $R_{bb}$ are each independently hydrogen, deuterium, alkyl, deuterated alkyl, haloalkyl, alkoxy, hydroxyalkyl, haloalkoxy, halogen, cyano, nitro, hydroxy, amino, alkenyl, alkynyl, deuterated alkenyl, deuterated alkynyl, cycloalkyl, heterocyclyl, aryl, or heteroaryl, wherein each of the alkyl, deuterated alkyl, haloalkyl, alkoxy, hydroxyalkyl, haloalkoxy, alkenyl, alkynyl, deuterated alkenyl, deuterated alkynyl, cycloalkyl, heterocyclyl, aryl, or heteroaryl is optionally further substituted by one or more substituents of hydrogen, deuterium, silyl, alkylsilyl, substituted or unsubstituted alkyl, halogen, hydroxy, substituted or unsubstituted amino, oxo, nitro, cyano, substituted or unsubstituted alkenyl, substituted or unsubstituted alkynyl, substituted or unsubstituted alkoxy, substituted or unsubstituted hydroxyalkyl, substituted or unsubstituted cycloalkyl, substituted or unsubstituted heterocyclyl, substituted or unsubstituted aryl, or substituted or unsubstituted heteroaryl;

$R_3$ is H;

Z is O;

n1=0, 1, 2, 3, or 4;

m1=0, 1, 2, 3, or 4;

p=0, 1, 2, or 3;

q=0, 1, 2, or 3;

or

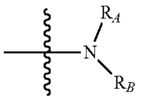

is represented by any one of the following structures:

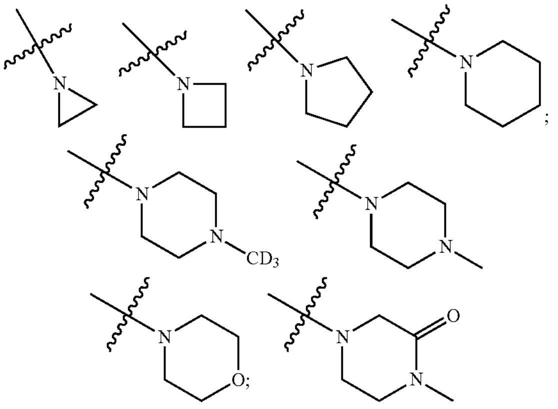

-continued

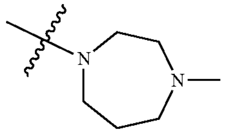

or

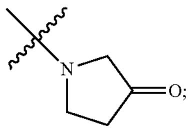

and

Y is a linking group represented by any one of the following structures:

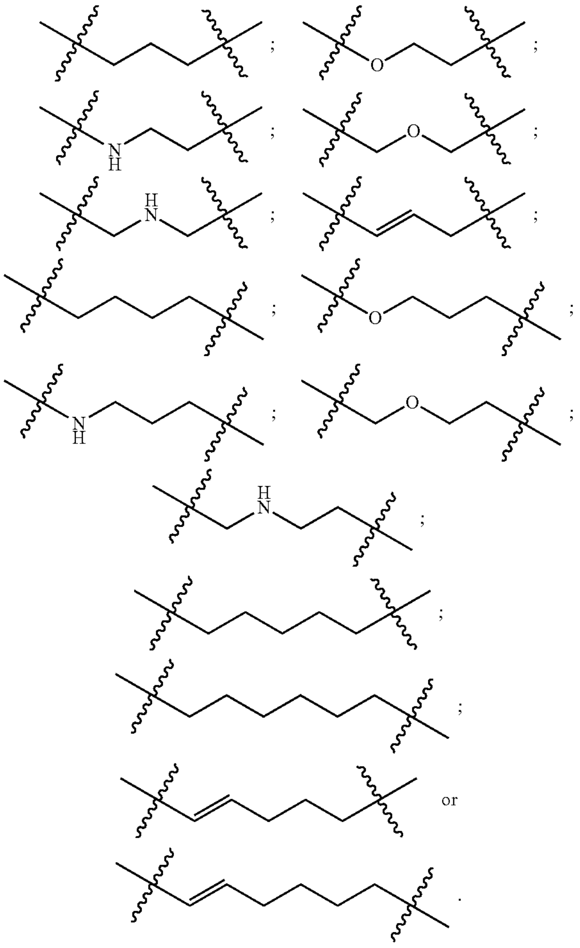

2. The compound, or the stereoisomer, tautomer or pharmaceutically acceptable salt thereof according to claim 1, wherein the compound is represented by any one of the following structures:

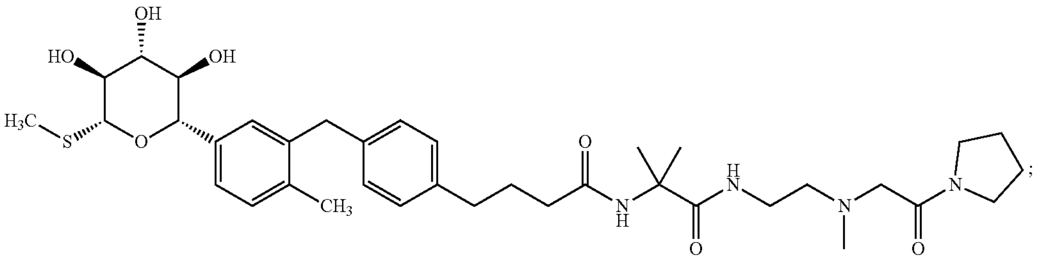

-continued
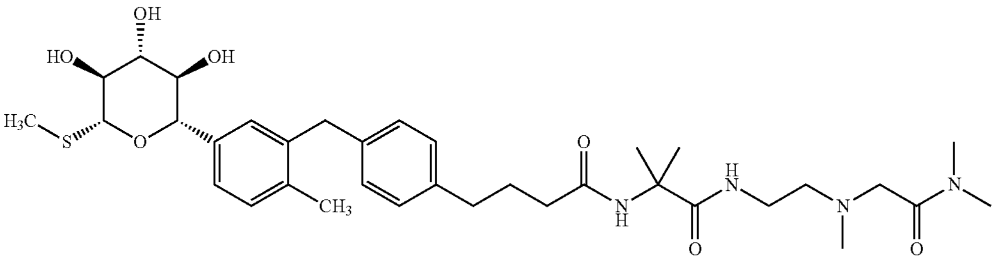
;
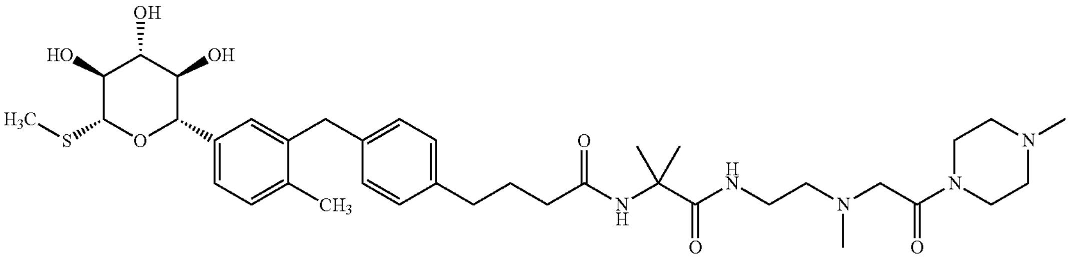
;
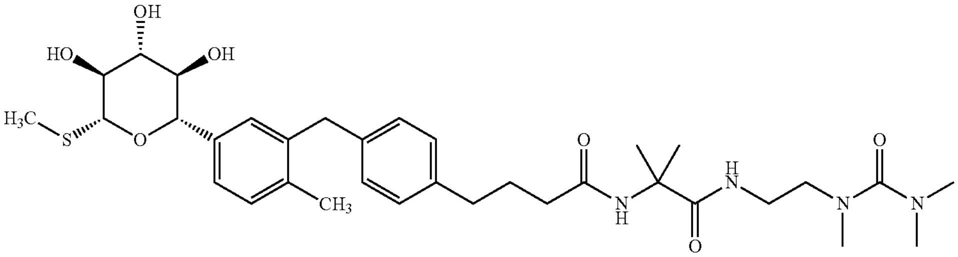
;
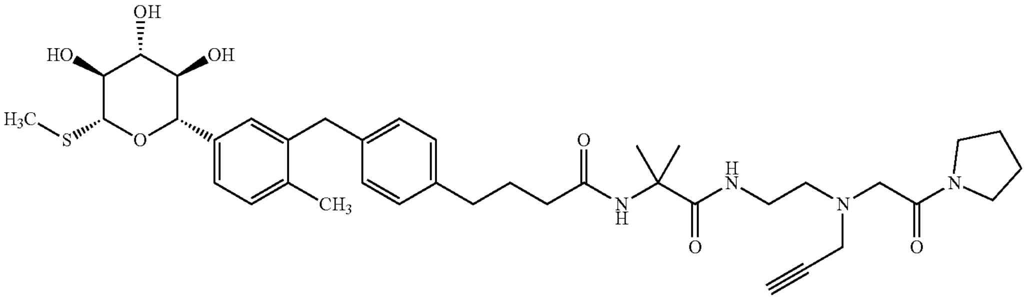
;
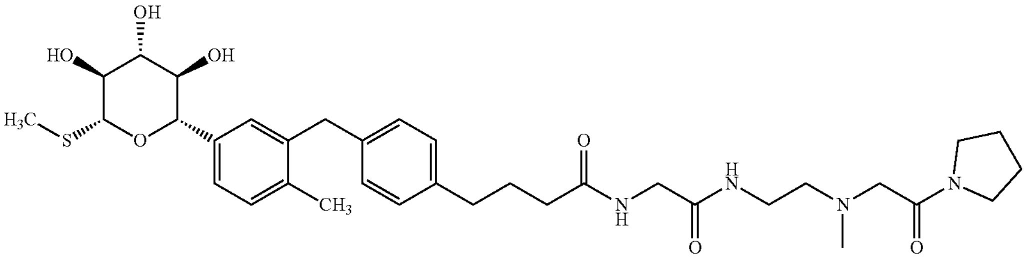
;
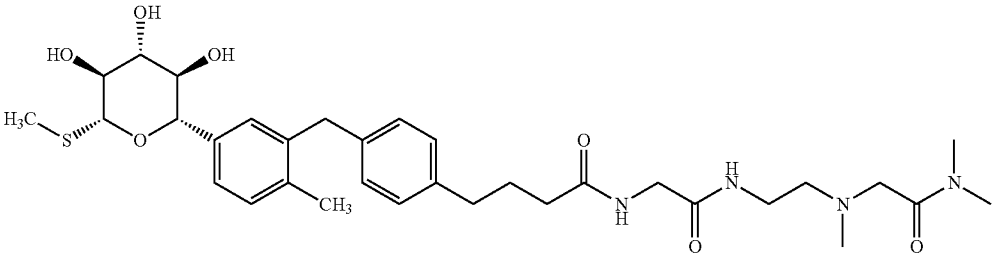
;

-continued

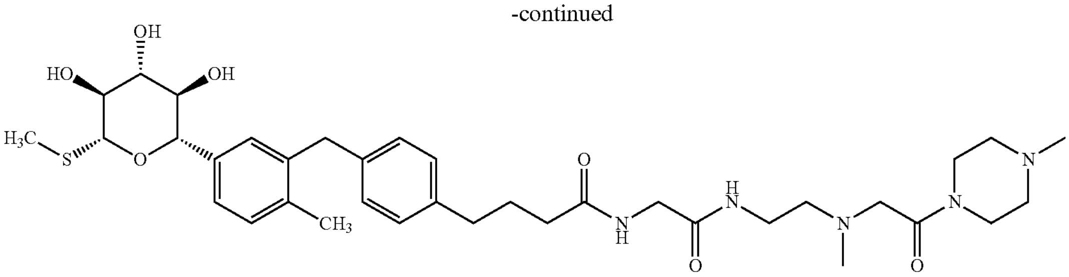

; or

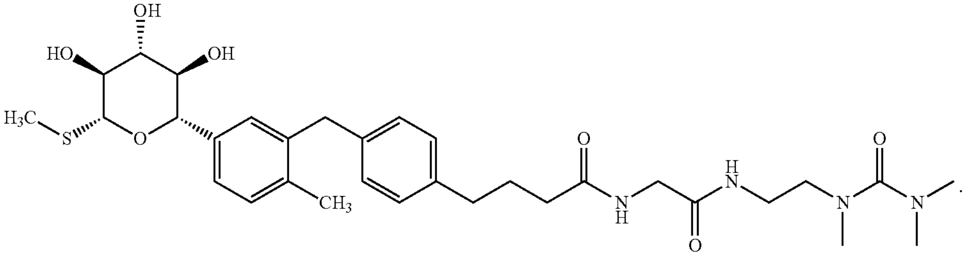

.

3. A compound of formula (I-1), or a stereoisomer, tautomer or pharmaceutically acceptable salt thereof, (I-1)

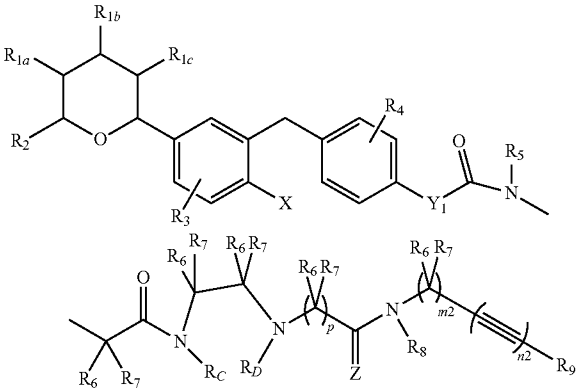

wherein, $R_{1a}$, $R_{1b}$ and $R_{1c}$ are each independently F, —$OR_{1A}$, or —$NHR_{1A}$, wherein each $R_{1A}$ is independently hydrogen, C1-C6 alkyl, or acyl;

$R_C$ and $R_D$ are each independently hydrogen, deuterium, halogen, C1-C6 alkyl, C3-C6 cycloalkyl, C2-C6 alkenyl, or C2-C6 alkynyl;

or $R_C$ and $R_D$ together with the nitrogen atoms attached therewith form a 3- to 8-membered heterocycle containing one or more carbon, nitrogen, oxygen or sulfur atoms, and optionally being further substituted by halogen, alkyl, cycloalkyl, aryl, alkoxy, alkenyl, alkynyl, or oxo;

$R_2$ is —$S(O)_m$—$R_{1A}$, and m=0, 1, or 2;

$R_3$, $R_4$, $R_5$, $R_6$, $R_7$, $R_8$ and $R_9$ are each independently hydrogen, deuterium, halogen, C1-C6 alkyl, cycloalkyl, cycloalkylalkyl, acyl, or C2-C8 alkynyl;

m2=0, 1, 2, or 3;

n2=0, 1, 2, or 3;

p=0, 1, 2, 3, 4, or 5;

X is hydrogen, deuterium, halogen, C1-C6 alkyl, C3-C6 cycloalkyl, C2-C6 alkenyl, or C2-C6 alkynyl;

Z is oxygen or sulfur;

$Y_1$ is a linking group represented by any one of the following structures:

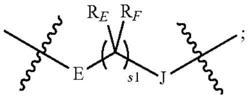

;

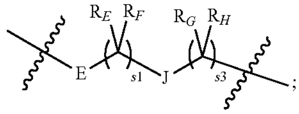

; or

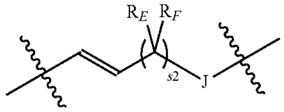

, wherein, $R_E$, $R_F$, $R_G$ and $R_H$ are each independently hydrogen, deuterium, halogen, C1-C6 alkyl, or acyl;

E and J are independently a single bond, —$CH_2$—, oxygen, or —NH—;

s1=0, 1, 2, 3, 4, or 5;

s2=0, 1, 2, 3, 4, or 5; and s3=0, 1, 2, 3, 4, or 5.

4. The compound, or the stereoisomer, tautomer or pharmaceutically acceptable salt thereof according to claim 3, wherein the compound is represented by any one of formulas (II-1) or (III-1), (II-1)

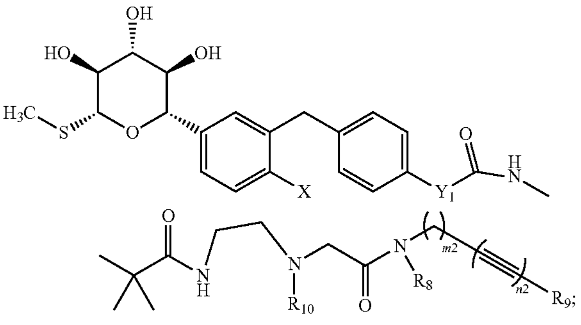

;

-continued (III-1)

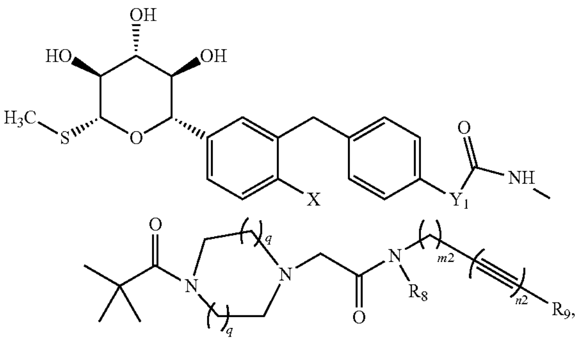

wherein, X is hydrogen, deuterium, halogen, C1-C6 alkyl, C3-C6 cycloalkyl, C2-C6 alkenyl, or C2-C6 alkynyl;

$R_8$ and $R_9$ are each independently hydrogen, deuterium, halogen, C1-C6 alkyl, cycloalkyl, cycloalkylalkyl, acyl, or C2-C8 alkynyl;

$R_{10}$ is hydrogen, deuterium, halogen, C1-C6 alkyl, C3-C6 cycloalkyl, C2-C6 alkenyl, or C2-C6 alkynyl;

m2=0, 1, 2, or 3;

n2=0 or 1;

q=0, 1, 2, or 3;

$Y_1$ is a linking group represented by any one of the following structures:

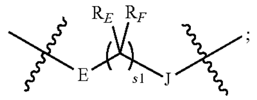
;
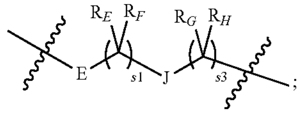
; or
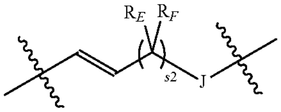
, wherein, $R_E$, $R_F$, $R_G$ and $R_H$ are each independently hydrogen, deuterium, halogen, C1-C6 alkyl, or acyl;

E and J are each independently a single bond, —$CH_2$—, oxygen, or —NH—;

s1=0, 1, 2, 3, 4, or 5;

s2=0, 1, 2, 3, 4, or 5; and s3=0, 1, 2, 3, 4, or 5.

5. The compound, or the stereoisomer, tautomer or pharmaceutically acceptable salt thereof according to claim 3, wherein the compound is represented by any one of formulas (VI) or (V), (VI)

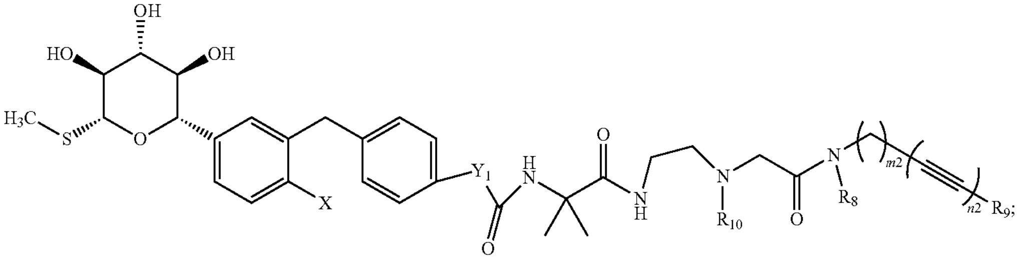

(V)

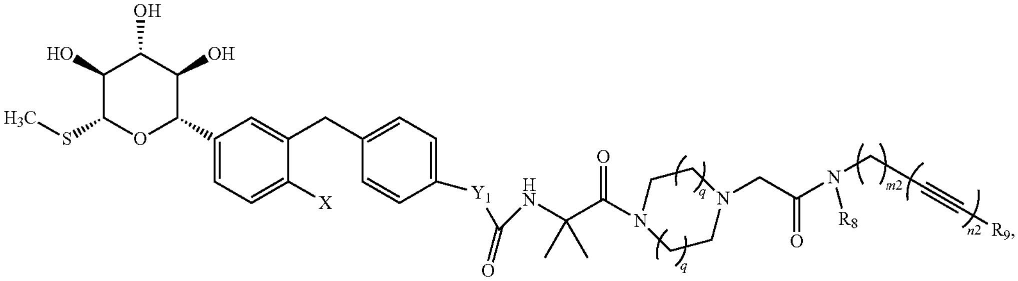

wherein, X is hydrogen, deuterium, halogen, C1-C6 alkyl, C3-C6 cycloalkyl, C2-C6 alkenyl, or C2-C6 alkynyl;

$R_8$ and $R_9$ are each independently hydrogen, deuterium, halogen, C1-C6 alkyl, or acyl;

$R_{10}$ is hydrogen, deuterium, halogen, C1-C6 alkyl, C3-C6 cycloalkyl, C2-C6 alkenyl, or C2-C6 alkynyl;

m2=0, 1, 2, or 3;

n2=0 or 1;

q=0, 1, 2, or 3; and $Y_1$ is a linking group represented by any one of the following structures:

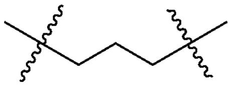
;
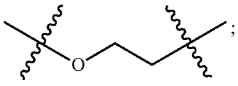
;
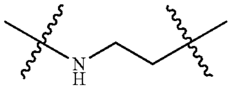
;
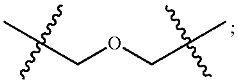
;
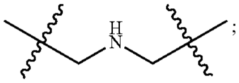
;
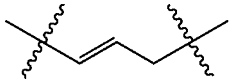
;

-continued

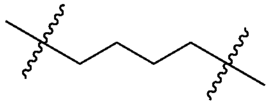
;
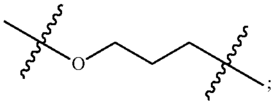
;
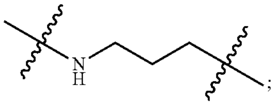
;
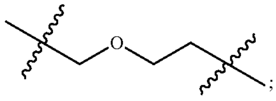
;
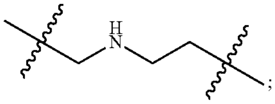
;
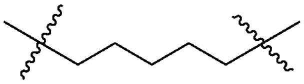
;
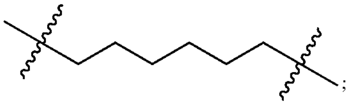
;

-continued

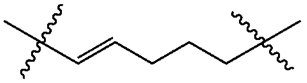
or
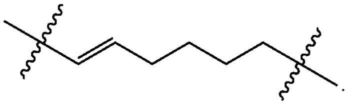
.

6. The compound, or the stereoisomer, tautomer or pharmaceutically acceptable salt thereof according to claim 4, wherein in formula (II-1), wherein X is hydrogen, deuterium, fluorine, bromine, iodine, methyl, ethyl, vinyl, or ethynyl; and $R_9$ is hydrogen, deuterium, fluorine, bromine, iodine, methyl, ethyl, C3~C8 cycloalkyl, or ethynyl.

7. The compound, or the stereoisomer, tautomer or pharmaceutically acceptable salt thereof according to claim 5, wherein the compound is represented by any one of the following structures:

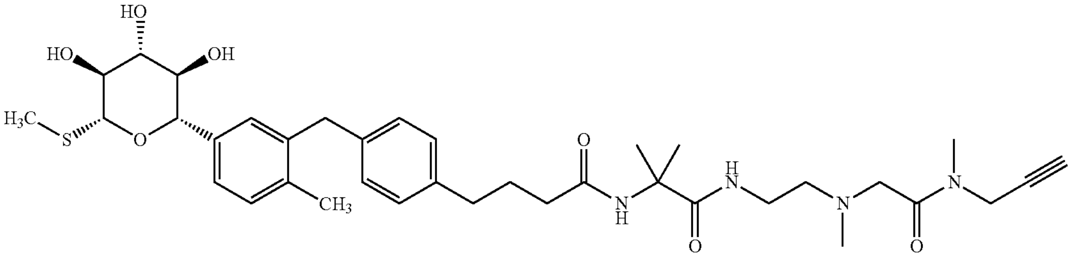
;
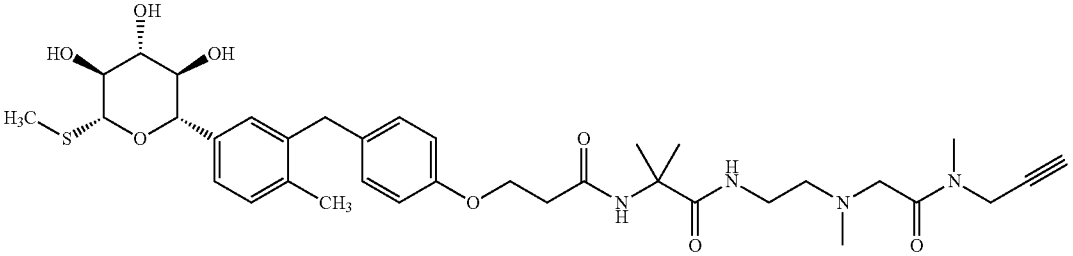
;
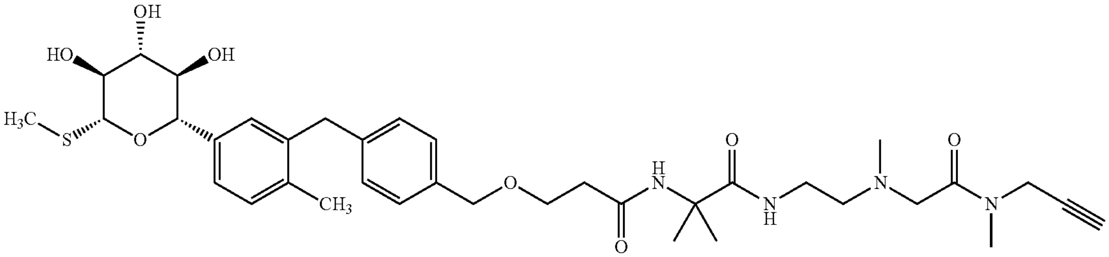
;
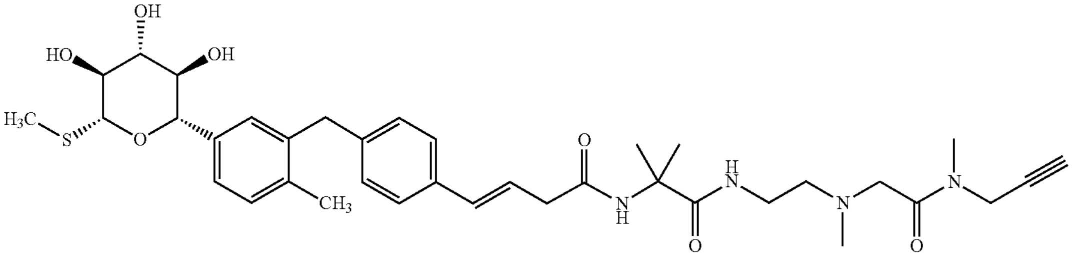
;

-continued
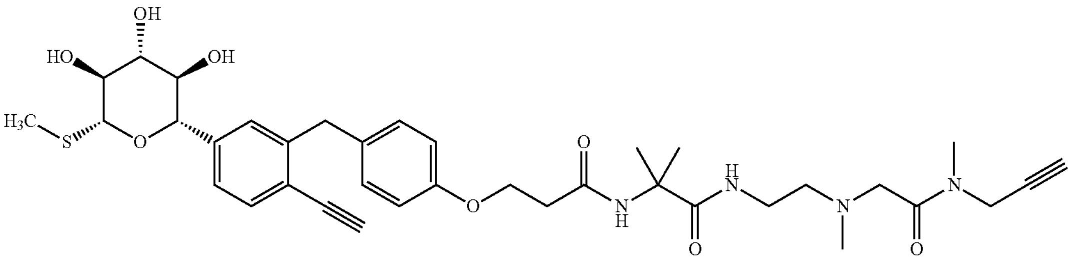
;
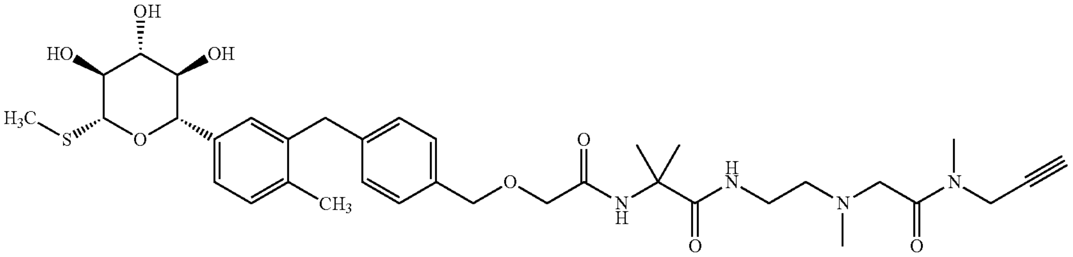
;
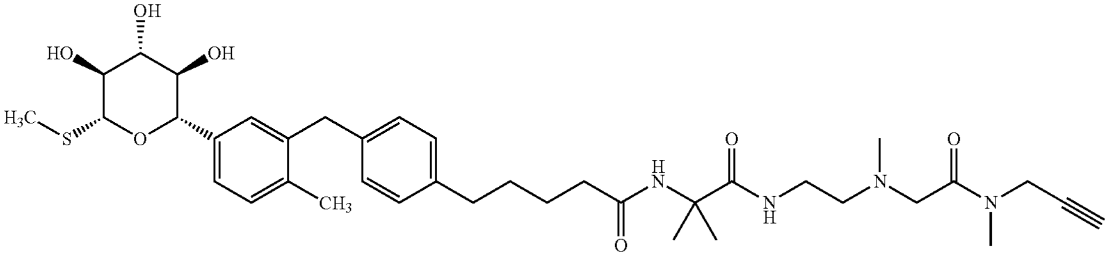
;
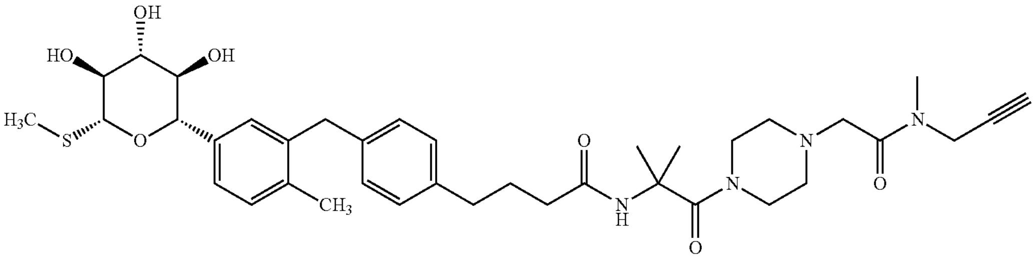
;
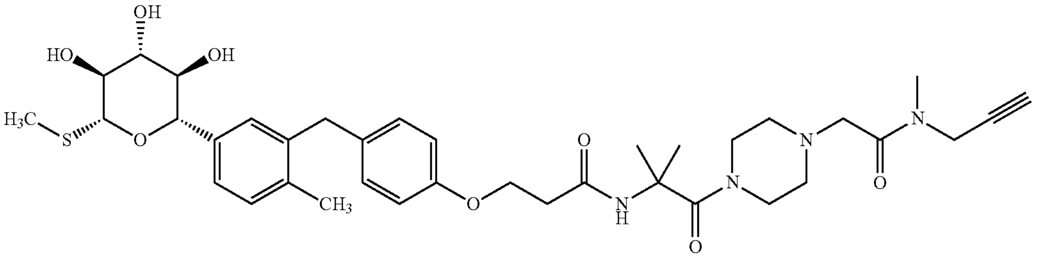
;
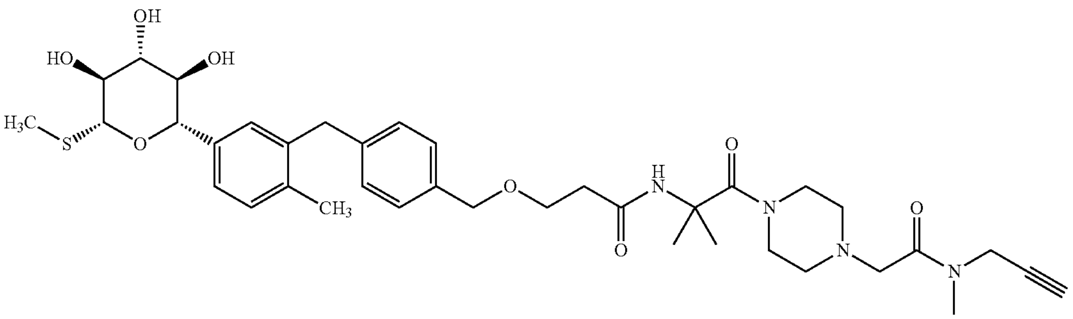
;

-continued

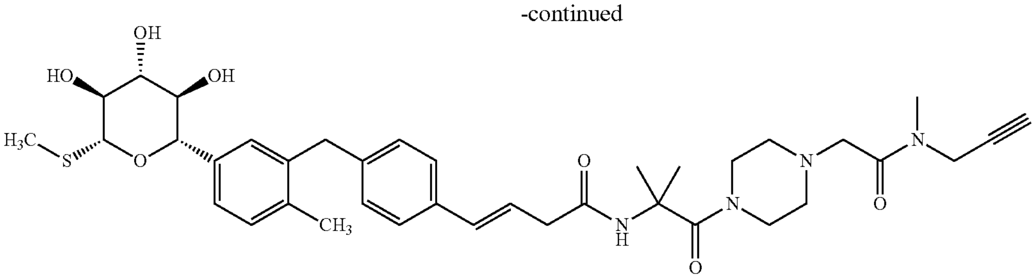

;

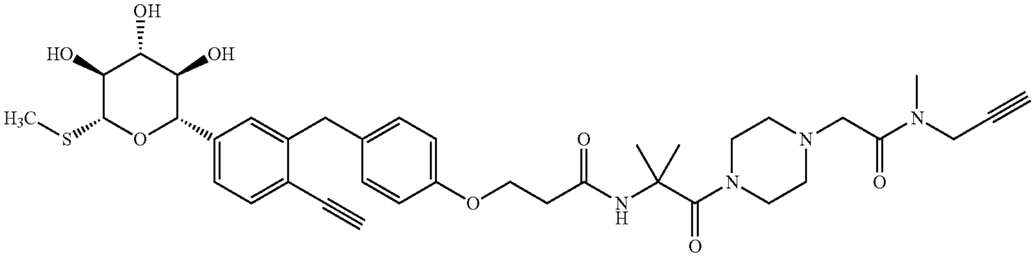

;

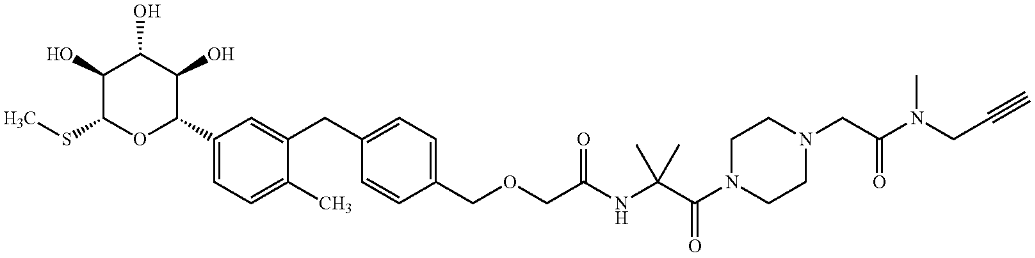

; or

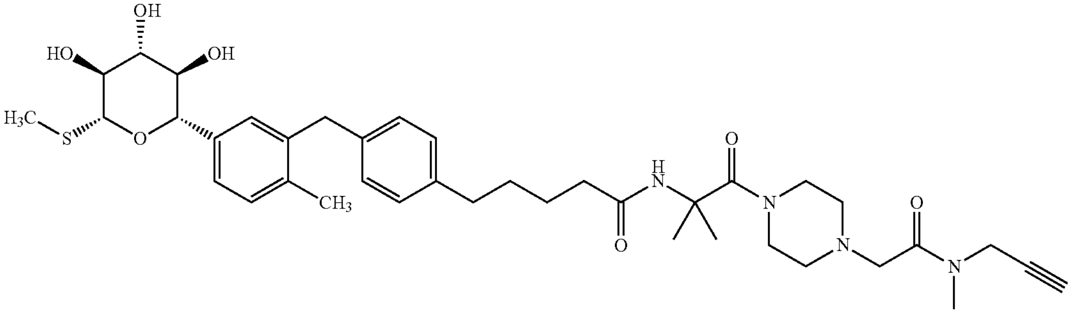

.

8. A pharmaceutical composition, comprising a therapeutically effective dose of the compound or the stereoisomer, the tautomer or the pharmaceutically acceptable salt thereof according to claim 1, and a pharmaceutically acceptable carrier.

9. A method for treating and improving diabetes, cardiovascular and cerebrovascular diseases, weight loss, fatty liver, constipation, metabolism-related diseases and for treating tumors, comprising administering a therapeutically effective amount of the compound or the stereoisomer, the tautomer or the pharmaceutically acceptable salt thereof according to claim 1 or a pharmaceutical composition comprising the compound of claim 3 to a subject in need thereof.

10. A method for inhibiting SGLT1/SGLT2 or for treating diseases related to SGLT1/SGLT2 function, comprising administering a therapeutically effective amount of the compound or the stereoisomer, the tautomer or the pharmaceutically acceptable salt thereof according to claim 1 or a pharmaceutical composition comprising the compound of claim 3 to a subject in need thereof.

11. The method according to claim 9, wherein other therapeutic drugs already taken or currently taken by patients comprise hypotensive drugs, hypolipidemic drugs, antidiabetic drugs, hypoglycemic drugs, weight-loss drugs, or appetite suppressants.

12. A pharmaceutical composition, comprising a therapeutically effective dose of the compound or the stereoisomer, the tautomer or the pharmaceutically acceptable salt thereof according to claim 3, and a pharmaceutically acceptable carrier.

13. A method for treating and improving diabetes, cardiovascular and cerebrovascular diseases, weight loss, fatty liver, constipation, metabolism-related diseases and for treating tumors, comprising administering a therapeutically effective amount of the compound or the stereoisomer, the tautomer or the pharmaceutically acceptable salt thereof according to claim 3 or a pharmaceutical composition comprising the compound of claim 8 to a subject in need thereof.

14. A method for inhibiting SGLT1/SGLT2 or for treating diseases related to SGLT1/SGLT2 function, comprising administering a therapeutically effective amount of the compound or the stereoisomer, the tautomer or the pharmaceutically acceptable salt thereof according to claim 3 or a pharmaceutical composition comprising the compound of claim 8 to a subject in need thereof.

* * * * *